(12) United States Patent
Slack

(10) Patent No.: US 7,964,376 B2
(45) Date of Patent: Jun. 21, 2011

(54) CHIMERIC PROTEINS AND THEIR USE IN METHODS TO SCREEN FOR SWEET TASTE MODULATORS

(75) Inventor: Jay Patrick Slack, Loveland, OH (US)

(73) Assignee: Givaudan SA (CH)

( * ) Notice: Subject to any disclaimer, the term of this patent is extended or adjusted under 35 U.S.C. 154(b) by 0 days.

(21) Appl. No.: 12/305,605

(22) PCT Filed: Jun. 15, 2007

(86) PCT No.: PCT/CH2007/000297
§ 371 (c)(1),
(2), (4) Date: Dec. 18, 2008

(87) PCT Pub. No.: WO2007/147275
PCT Pub. Date: Dec. 27, 2007

(65) Prior Publication Data
US 2009/0286262 A1    Nov. 19, 2009

Related U.S. Application Data

(60) Provisional application No. 60/814,866, filed on Jun. 19, 2006, provisional application No. 60/881,402, filed on Jan. 19, 2007.

(51) Int. Cl.
C07K 14/705    (2006.01)
C07K 19/00     (2006.01)
C12N 15/62     (2006.01)
G01N 33/566    (2006.01)

(52) U.S. Cl. .................. 435/69.7; 435/7.2; 435/252.3; 435/320.1; 530/350; 536/23.4

(58) Field of Classification Search .................. None
See application file for complete search history.

(56) References Cited

U.S. PATENT DOCUMENTS
2003/0166137 A1    9/2003  Zuker

FOREIGN PATENT DOCUMENTS
WO    WO 03/004992 A2    1/2003
WO    WO 2005/015158 A2   2/2005

*Primary Examiner* — John D Ulm
(74) *Attorney, Agent, or Firm* — Curatolo Sidoti Co., LPA; Joseph G. Curatolo; Salvatore A. Sidoti

(57) ABSTRACT

Novel chimeric proteins functional to screen for sweet taste modulators, the corresponding nucleic acid sequences, expression vectors, transfected host cells, and screening methods for modulators and enhancers of the sweet taste response employing the aforementioned are provided.

26 Claims, No Drawings

SEQUENCE LISTING

<160> NUMBER OF SEQ ID NOS: 25

<210> SEQ ID NO 1
<211> LENGTH: 2661
<212> TYPE: DNA
<213> ORGANISM: artificial
<220> FEATURE:
<223> OTHER INFORMATION: fusion product of human DNA sequence fragments
<220> FEATURE:
<221> NAME/KEY: CDS
<222> LOCATION: (1)..(2661)

<400> SEQUENCE: 1

```
atg gca ttt tat agc tgc tgc tgg gtc ctc ttg gca ctc acc tgg cac      48
Met Ala Phe Tyr Ser Cys Cys Trp Val Leu Leu Ala Leu Thr Trp His
1               5                   10                  15 acc tct gcc tac ggg cca gac cag cga gcc caa aag aag ggg gac att      96
Thr Ser Ala Tyr Gly Pro Asp Gln Arg Ala Gln Lys Lys Gly Asp Ile
            20                  25                  30 atc ctt ggg ggg ctc ttt cct att cat ttt gga gta gca gct aaa gat     144
Ile Leu Gly Gly Leu Phe Pro Ile His Phe Gly Val Ala Ala Lys Asp
        35                  40                  45 caa gat ctc aaa tca agg ccg gag tct gtg gaa tgt atc agg tat aat     192
Gln Asp Leu Lys Ser Arg Pro Glu Ser Val Glu Cys Ile Arg Tyr Asn
    50                  55                  60 ttc cgt ggg ttt cgc tgg tta cag gct atg ata ttt gcc ata gag gag     240
Phe Arg Gly Phe Arg Trp Leu Gln Ala Met Ile Phe Ala Ile Glu Glu
65                  70                  75                  80 ata aac agc agc cca gcc ctt ctt ccc aac ttg acg ctg gga tac agg     288
Ile Asn Ser Ser Pro Ala Leu Leu Pro Asn Leu Thr Leu Gly Tyr Arg
                85                  90                  95 ata ttt gac act tgc aac acc gtt tct aag gcc ttg gaa gcc acc ctg     336
Ile Phe Asp Thr Cys Asn Thr Val Ser Lys Ala Leu Glu Ala Thr Leu
            100                 105                 110 agt ttt gtt gct caa aac aaa att gat tct ttg aac ctt gat gag ttc     384
Ser Phe Val Ala Gln Asn Lys Ile Asp Ser Leu Asn Leu Asp Glu Phe
        115                 120                 125 tgc aac tgc tca gag cac att ccc tct acg att gct gtg gtg gga gca     432
Cys Asn Cys Ser Glu His Ile Pro Ser Thr Ile Ala Val Val Gly Ala
    130                 135                 140 act ggc tca ggc gtc tcc acg gca gtg gca aat ctg ctg ggg ctc ttc     480
Thr Gly Ser Gly Val Ser Thr Ala Val Ala Asn Leu Leu Gly Leu Phe
145                 150                 155                 160 tac att ccc cag gtc agt tat gcc tcc tcc agc aga ctc ctc agc aac     528
Tyr Ile Pro Gln Val Ser Tyr Ala Ser Ser Ser Arg Leu Leu Ser Asn
                165                 170                 175 aag aat caa ttc aag tct ttc ctc cga acc atc ccc aat gat gag cac     576
Lys Asn Gln Phe Lys Ser Phe Leu Arg Thr Ile Pro Asn Asp Glu His
            180                 185                 190 cag gcc act gcc atg gca gac atc atc gag tat ttc cgc tgg aac tgg     624
Gln Ala Thr Ala Met Ala Asp Ile Ile Glu Tyr Phe Arg Trp Asn Trp
        195                 200                 205 gtg ggc aca att gca gct gat gac gac tat ggg cgg ccg ggg att gag     672
Val Gly Thr Ile Ala Ala Asp Asp Asp Tyr Gly Arg Pro Gly Ile Glu
    210                 215                 220 aaa ttc cga gag gaa gct gag gaa agg gat atc tgc atc gac ttc agt     720
Lys Phe Arg Glu Glu Ala Glu Glu Arg Asp Ile Cys Ile Asp Phe Ser
225                 230                 235                 240 gaa ctc atc tcc cag tac tct gat gag gaa gag atc cag cat gtg gta     768
Glu Leu Ile Ser Gln Tyr Ser Asp Glu Glu Glu Ile Gln His Val Val
                245                 250                 255
```

| | |
|---|---|
| gag gtg att caa aat tcc acg gcc aaa gtc atc gtg gtt ttc tcc agt<br>Glu Val Ile Gln Asn Ser Thr Ala Lys Val Ile Val Val Phe Ser Ser<br>260 265 270 | 816 |
| ggc cca gat ctt gag ccc ctc atc aag gag att gtc cgg cgc aat atc<br>Gly Pro Asp Leu Glu Pro Leu Ile Lys Glu Ile Val Arg Arg Asn Ile<br>275 280 285 | 864 |
| acg ggc aag atc tgg ctg gcc agc gag gcc tgg gcc agc tcc tcc ctg<br>Thr Gly Lys Ile Trp Leu Ala Ser Glu Ala Trp Ala Ser Ser Ser Leu<br>290 295 300 | 912 |
| atc gcc atg cct cag tac ttc cac gtg gtt ggc ggc acc att gga ttc<br>Ile Ala Met Pro Gln Tyr Phe His Val Val Gly Gly Thr Ile Gly Phe<br>305 310 315 320 | 960 |
| gct ctg aag gct ggg cag atc cca ggc ttc cgg gaa ttc ctg aag aag<br>Ala Leu Lys Ala Gly Gln Ile Pro Gly Phe Arg Glu Phe Leu Lys Lys<br>325 330 335 | 1008 |
| gtc cat ccc agg aag tct gtc cac aat ggt ttt gcc aag gag ttt tgg<br>Val His Pro Arg Lys Ser Val His Asn Gly Phe Ala Lys Glu Phe Trp<br>340 345 350 | 1056 |
| gaa gaa aca ttt aac tgc cac ctc caa gaa ggt gca aaa gga cct tta<br>Glu Glu Thr Phe Asn Cys His Leu Gln Glu Gly Ala Lys Gly Pro Leu<br>355 360 365 | 1104 |
| cct gtg gac acc ttt ctg aga ggt cac gaa gaa agt ggc gac agg ttt<br>Pro Val Asp Thr Phe Leu Arg Gly His Glu Glu Ser Gly Asp Arg Phe<br>370 375 380 | 1152 |
| agc aac agc tcg aca gcc ttc cga ccc ctc tgt aca ggg gat gag aac<br>Ser Asn Ser Ser Thr Ala Phe Arg Pro Leu Cys Thr Gly Asp Glu Asn<br>385 390 395 400 | 1200 |
| atc agc agt gtc gag acc cct tac ata gat tac acg cat tta cgg ata<br>Ile Ser Ser Val Glu Thr Pro Tyr Ile Asp Tyr Thr His Leu Arg Ile<br>405 410 415 | 1248 |
| tcc tac aat gtg tac tta gca gtc tac tcc att gcc cac gcc ttg caa<br>Ser Tyr Asn Val Tyr Leu Ala Val Tyr Ser Ile Ala His Ala Leu Gln<br>420 425 430 | 1296 |
| gat ata tat acc tgc tta cct ggg aga ggg ctc ttc acc aat ggc tcc<br>Asp Ile Tyr Thr Cys Leu Pro Gly Arg Gly Leu Phe Thr Asn Gly Ser<br>435 440 445 | 1344 |
| tgt gca gac atc aag aaa gtt gag gcg tgg cag gtc ctg aag cac cta<br>Cys Ala Asp Ile Lys Lys Val Glu Ala Trp Gln Val Leu Lys His Leu<br>450 455 460 | 1392 |
| cgg cat cta aac ttt aca aac aat atg ggg gag cag gtg acc ttt gat<br>Arg His Leu Asn Phe Thr Asn Asn Met Gly Glu Gln Val Thr Phe Asp<br>465 470 475 480 | 1440 |
| gag tgt ggt gac ctg gtg ggg aac tat tcc atc atc aac tgg cac ctc<br>Glu Cys Gly Asp Leu Val Gly Asn Tyr Ser Ile Ile Asn Trp His Leu<br>485 490 495 | 1488 |
| tcc cca gag gat ggc tcc atc gtg ttt aag gaa gtc ggg tat tac aac<br>Ser Pro Glu Asp Gly Ser Ile Val Phe Lys Glu Val Gly Tyr Tyr Asn<br>500 505 510 | 1536 |
| gtc tat gcc aag aag gga gaa aga ctc ttc atc aac gag gag aaa atc<br>Val Tyr Ala Lys Lys Gly Glu Arg Leu Phe Ile Asn Glu Glu Lys Ile<br>515 520 525 | 1584 |
| ctg tgg agt ggg ttc tcc agg gag gtg ccg cgg tcc atg tgt tcc aag<br>Leu Trp Ser Gly Phe Ser Arg Glu Val Pro Arg Ser Met Cys Ser Lys<br>530 535 540 | 1632 |
| agg tgc cag tca ggg caa aag aag aag cct gtg ggc atc cac gtc tgc<br>Arg Cys Gln Ser Gly Gln Lys Lys Lys Pro Val Gly Ile His Val Cys<br>545 550 555 560 | 1680 |
| tgc ttc gag tgc atc gac tgc ctt ccc ggc acc ttc ctc aac cac act<br>Cys Phe Glu Cys Ile Asp Cys Leu Pro Gly Thr Phe Leu Asn His Thr<br>565 570 575 | 1728 |

```
gaa gat gaa tat gaa tgc cag gcc tgc ccg aat aac gag tgg tcc tac     1776
Glu Asp Glu Tyr Glu Cys Gln Ala Cys Pro Asn Asn Glu Trp Ser Tyr
            580                 585                 590 cag agt gag acc tcc tgc ttc aag cgg cag ctg gtc ttc ctg gaa tgg     1824
Gln Ser Glu Thr Ser Cys Phe Lys Arg Gln Leu Val Phe Leu Glu Trp
        595                 600                 605 cat gag gca ccc acc atc gct gtg gcc ctg ctg gcc gcc ctg ggc ttc     1872
His Glu Ala Pro Thr Ile Ala Val Ala Leu Leu Ala Ala Leu Gly Phe
    610                 615                 620 ctc agc acc ctg gcc atc ctg gtg ata ttc tgg agg cac ttc cag aca     1920
Leu Ser Thr Leu Ala Ile Leu Val Ile Phe Trp Arg His Phe Gln Thr
625                 630                 635                 640 ccc ata gtt cgc tcg gct ggg ggc ccc atg tgc ttc ctg atg ctg aca     1968
Pro Ile Val Arg Ser Ala Gly Gly Pro Met Cys Phe Leu Met Leu Thr
                645                 650                 655 ctg ctg ctg gtg gca tac atg gtg gtc ccg gtg tac gtg ggg ccg ccc     2016
Leu Leu Leu Val Ala Tyr Met Val Val Pro Val Tyr Val Gly Pro Pro
            660                 665                 670 aag gtc tcc acc tgc ctc tgc cgc cag gcc ctc ttt ccc ctc tgc ttc     2064
Lys Val Ser Thr Cys Leu Cys Arg Gln Ala Leu Phe Pro Leu Cys Phe
        675                 680                 685 aca atc tgc atc tcc tgt atc gcc gtg cgt tct ttc cag atc gtc tgc     2112
Thr Ile Cys Ile Ser Cys Ile Ala Val Arg Ser Phe Gln Ile Val Cys
    690                 695                 700 gcc ttc aag atg gcc agc cgc ttc cca cgc gcc tac agc tac tgg gtc     2160
Ala Phe Lys Met Ala Ser Arg Phe Pro Arg Ala Tyr Ser Tyr Trp Val
705                 710                 715                 720 cgc tac cag ggg ccc tac gtc tct atg gca ttt atc acg gta ctc aaa     2208
Arg Tyr Gln Gly Pro Tyr Val Ser Met Ala Phe Ile Thr Val Leu Lys
                725                 730                 735 atg gtc att gtg gta att ggc atg ctg gcc acg ggc ctc agt ccc acc     2256
Met Val Ile Val Ile Gly Met Leu Ala Thr Gly Leu Ser Pro Thr
            740                 745                 750 acc cgt act gac ccc gat gac ccc aag atc aca att gtc tcc tgt aac     2304
Thr Arg Thr Asp Pro Asp Asp Pro Lys Ile Thr Ile Val Ser Cys Asn
        755                 760                 765 ccc aac tac cgc aac agc ctg ctg ttc aac acc agc ctg gac ctg ctg     2352
Pro Asn Tyr Arg Asn Ser Leu Leu Phe Asn Thr Ser Leu Asp Leu Leu
    770                 775                 780 ctc tca gtg gtg ggt ttc agc ttc gcc tac atg ggc aaa gag ctg ccc     2400
Leu Ser Val Val Gly Phe Ser Phe Ala Tyr Met Gly Lys Glu Leu Pro
785                 790                 795                 800 acc aac tac aac gag gcc aag ttc atc acc ctc agc atg acc ttc tat     2448
Thr Asn Tyr Asn Glu Ala Lys Phe Ile Thr Leu Ser Met Thr Phe Tyr
                805                 810                 815 ttc acc tca tct gtc tcc ctc tgc acc ttc atg tct gcc tac agc ggg     2496
Phe Thr Ser Ser Val Ser Leu Cys Thr Phe Met Ser Ala Tyr Ser Gly
            820                 825                 830 gtg ctg gtc acc atc gtg gac ctc ttg gtc act gtg ctc aac ctc ctg     2544
Val Leu Val Thr Ile Val Asp Leu Leu Val Thr Val Leu Asn Leu Leu
        835                 840                 845 gcc atc agc ctg ggc tac ttc ggc ccc aag tgc tac atg atc ctc ttc     2592
Ala Ile Ser Leu Gly Tyr Phe Gly Pro Lys Cys Tyr Met Ile Leu Phe
    850                 855                 860 tac ccg gag cgc aac acg ccc gcc tac ttc aac agc atg atc cag ggc     2640
Tyr Pro Glu Arg Asn Thr Pro Ala Tyr Phe Asn Ser Met Ile Gln Gly
865                 870                 875                 880 tac acc atg agg agg gac tga                                         2661
Tyr Thr Met Arg Arg Asp
                885
```

<210> SEQ ID NO 2
<211> LENGTH: 886
<212> TYPE: PRT
<213> ORGANISM: artificial
<220> FEATURE:
<223> OTHER INFORMATION: Synthetic Construct

<400> SEQUENCE: 2

```
Met Ala Phe Tyr Ser Cys Cys Trp Val Leu Leu Ala Leu Thr Trp His
1               5                   10                  15

Thr Ser Ala Tyr Gly Pro Asp Gln Arg Ala Gln Lys Lys Gly Asp Ile
            20                  25                  30

Ile Leu Gly Gly Leu Phe Pro Ile His Phe Gly Val Ala Ala Lys Asp
        35                  40                  45

Gln Asp Leu Lys Ser Arg Pro Glu Ser Val Glu Cys Ile Arg Tyr Asn
    50                  55                  60

Phe Arg Gly Phe Arg Trp Leu Gln Ala Met Ile Phe Ala Ile Glu Glu
65                  70                  75                  80

Ile Asn Ser Ser Pro Ala Leu Leu Pro Asn Leu Thr Leu Gly Tyr Arg
                85                  90                  95

Ile Phe Asp Thr Cys Asn Thr Val Ser Lys Ala Leu Glu Ala Thr Leu
            100                 105                 110

Ser Phe Val Ala Gln Asn Lys Ile Asp Ser Leu Asn Leu Asp Glu Phe
        115                 120                 125

Cys Asn Cys Ser Glu His Ile Pro Ser Thr Ile Ala Val Val Gly Ala
    130                 135                 140

Thr Gly Ser Gly Val Ser Thr Ala Val Ala Asn Leu Leu Gly Leu Phe
145                 150                 155                 160

Tyr Ile Pro Gln Val Ser Tyr Ala Ser Ser Arg Leu Leu Ser Asn
                165                 170                 175

Lys Asn Gln Phe Lys Ser Phe Leu Arg Thr Ile Pro Asn Asp Glu His
            180                 185                 190

Gln Ala Thr Ala Met Ala Asp Ile Ile Glu Tyr Phe Arg Trp Asn Trp
        195                 200                 205

Val Gly Thr Ile Ala Ala Asp Asp Asp Tyr Gly Arg Pro Gly Ile Glu
    210                 215                 220

Lys Phe Arg Glu Glu Ala Glu Glu Arg Asp Ile Cys Ile Asp Phe Ser
225                 230                 235                 240

Glu Leu Ile Ser Gln Tyr Ser Asp Glu Glu Ile Gln His Val Val
                245                 250                 255

Glu Val Ile Gln Asn Ser Thr Ala Lys Val Ile Val Val Phe Ser Ser
            260                 265                 270

Gly Pro Asp Leu Glu Pro Leu Ile Lys Glu Ile Val Arg Arg Asn Ile
        275                 280                 285

Thr Gly Lys Ile Trp Leu Ala Ser Glu Ala Trp Ala Ser Ser Ser Leu
    290                 295                 300

Ile Ala Met Pro Gln Tyr Phe His Val Val Gly Gly Thr Ile Gly Phe
305                 310                 315                 320

Ala Leu Lys Ala Gly Gln Ile Pro Gly Phe Arg Glu Phe Leu Lys Lys
                325                 330                 335

Val His Pro Arg Lys Ser Val His Asn Gly Phe Ala Lys Glu Phe Trp
            340                 345                 350

Glu Glu Thr Phe Asn Cys His Leu Gln Glu Gly Ala Lys Gly Pro Leu
        355                 360                 365
```

-continued

Pro Val Asp Thr Phe Leu Arg Gly His Glu Glu Ser Gly Asp Arg Phe
370                     375                     380

Ser Asn Ser Ser Thr Ala Phe Arg Pro Leu Cys Thr Gly Asp Glu Asn
385                     390                     395                     400

Ile Ser Ser Val Glu Thr Pro Tyr Ile Asp Tyr Thr His Leu Arg Ile
            405                     410                     415

Ser Tyr Asn Val Tyr Leu Ala Val Tyr Ser Ile Ala His Ala Leu Gln
            420                     425                     430

Asp Ile Tyr Thr Cys Leu Pro Gly Arg Gly Leu Phe Thr Asn Gly Ser
            435                     440                     445

Cys Ala Asp Ile Lys Lys Val Glu Ala Trp Gln Val Leu Lys His Leu
450                     455                     460

Arg His Leu Asn Phe Thr Asn Asn Met Gly Glu Gln Val Thr Phe Asp
465                     470                     475                     480

Glu Cys Gly Asp Leu Val Gly Asn Tyr Ser Ile Ile Asn Trp His Leu
                485                     490                     495

Ser Pro Glu Asp Gly Ser Ile Val Phe Lys Glu Val Gly Tyr Tyr Asn
            500                     505                     510

Val Tyr Ala Lys Lys Gly Glu Arg Leu Phe Ile Asn Glu Glu Lys Ile
            515                     520                     525

Leu Trp Ser Gly Phe Ser Arg Glu Val Pro Arg Ser Met Cys Ser Lys
530                     535                     540

Arg Cys Gln Ser Gly Gln Lys Lys Lys Pro Val Gly Ile His Val Cys
545                     550                     555                     560

Cys Phe Glu Cys Ile Asp Cys Leu Pro Gly Thr Phe Leu Asn His Thr
                565                     570                     575

Glu Asp Glu Tyr Glu Cys Gln Ala Cys Pro Asn Asn Glu Trp Ser Tyr
            580                     585                     590

Gln Ser Glu Thr Ser Cys Phe Lys Arg Gln Leu Val Phe Leu Glu Trp
            595                     600                     605

His Glu Ala Pro Thr Ile Ala Val Ala Leu Leu Ala Ala Leu Gly Phe
610                     615                     620

Leu Ser Thr Leu Ala Ile Leu Val Ile Phe Trp Arg His Phe Gln Thr
625                     630                     635                     640

Pro Ile Val Arg Ser Ala Gly Gly Pro Met Cys Phe Leu Met Leu Thr
                645                     650                     655

Leu Leu Leu Val Ala Tyr Met Val Val Pro Val Tyr Val Gly Pro Pro
            660                     665                     670

Lys Val Ser Thr Cys Leu Cys Arg Gln Ala Leu Phe Pro Leu Cys Phe
            675                     680                     685

Thr Ile Cys Ile Ser Cys Ile Ala Val Arg Ser Phe Gln Ile Val Cys
690                     695                     700

Ala Phe Lys Met Ala Ser Arg Phe Pro Arg Ala Tyr Ser Tyr Trp Val
705                     710                     715                     720

Arg Tyr Gln Gly Pro Tyr Val Ser Met Ala Phe Ile Thr Val Leu Lys
                725                     730                     735

Met Val Ile Val Val Ile Gly Met Leu Ala Thr Gly Leu Ser Pro Thr
            740                     745                     750

Thr Arg Thr Asp Pro Asp Asp Pro Lys Ile Thr Ile Val Ser Cys Asn
            755                     760                     765

Pro Asn Tyr Arg Asn Ser Leu Leu Phe Asn Thr Ser Leu Asp Leu Leu
            770                     775                     780

Leu Ser Val Val Gly Phe Ser Phe Ala Tyr Met Gly Lys Glu Leu Pro
785                     790                     795                     800

```
Thr Asn Tyr Asn Glu Ala Lys Phe Ile Thr Leu Ser Met Thr Phe Tyr
                805                 810                 815

Phe Thr Ser Ser Val Ser Leu Cys Thr Phe Met Ser Ala Tyr Ser Gly
            820                 825                 830

Val Leu Val Thr Ile Val Asp Leu Val Thr Val Leu Asn Leu Leu
                835                 840                 845

Ala Ile Ser Leu Gly Tyr Phe Gly Pro Lys Cys Tyr Met Ile Leu Phe
        850                 855                 860

Tyr Pro Glu Arg Asn Thr Pro Ala Tyr Phe Asn Ser Met Ile Gln Gly
865                 870                 875                 880

Tyr Thr Met Arg Arg Asp
                885

<210> SEQ ID NO 3
<211> LENGTH: 2688
<212> TYPE: DNA
<213> ORGANISM: artificial
<220> FEATURE:
<223> OTHER INFORMATION: fusion product of human DNA sequence fragments
<220> FEATURE:
<221> NAME/KEY: CDS
<222> LOCATION: (1)..(2688)

<400> SEQUENCE: 3 atg gca ttt tat agc tgc tgc tgg gtc ctc ttg gca ctc acc tgg cac      48
Met Ala Phe Tyr Ser Cys Cys Trp Val Leu Leu Ala Leu Thr Trp His
1               5                   10                  15 acc tct gcc tac ggg cca gac cag cga gcc caa aag aag ggg gac att      96
Thr Ser Ala Tyr Gly Pro Asp Gln Arg Ala Gln Lys Lys Gly Asp Ile
                20                  25                  30 atc ctt ggg ggg ctc ttt cct att cat ttt gga gta gca gct aaa gat     144
Ile Leu Gly Gly Leu Phe Pro Ile His Phe Gly Val Ala Ala Lys Asp
            35                  40                  45 caa gat ctc aaa tca agg ccg gag tct gtg gaa tgt atc agg tat aat     192
Gln Asp Leu Lys Ser Arg Pro Glu Ser Val Glu Cys Ile Arg Tyr Asn
        50                  55                  60 ttc cgt ggg ttt cgc tgg tta cag gct atg ata ttt gcc ata gag gag     240
Phe Arg Gly Phe Arg Trp Leu Gln Ala Met Ile Phe Ala Ile Glu Glu
65                  70                  75                  80 ata aac agc agc cca gcc ctt ctt ccc aac ttg acg ctg gga tac agg     288
Ile Asn Ser Ser Pro Ala Leu Leu Pro Asn Leu Thr Leu Gly Tyr Arg
                85                  90                  95 ata ttt gac act tgc aac acc gtt tct aag gcc ttg gaa gcc acc ctg     336
Ile Phe Asp Thr Cys Asn Thr Val Ser Lys Ala Leu Glu Ala Thr Leu
                100                 105                 110 agt ttt gtt gct caa aac aaa att gat tct ttg aac ctt gat gag ttc     384
Ser Phe Val Ala Gln Asn Lys Ile Asp Ser Leu Asn Leu Asp Glu Phe
            115                 120                 125 tgc aac tgc tca gag cac att ccc tct acg att gct gtg gtg gga gca     432
Cys Asn Cys Ser Glu His Ile Pro Ser Thr Ile Ala Val Val Gly Ala
        130                 135                 140 act ggc tca ggc gtc tcc acg gca gtg gca aat ctg ctg ggg ctc ttc     480
Thr Gly Ser Gly Val Ser Thr Ala Val Ala Asn Leu Leu Gly Leu Phe
145                 150                 155                 160 tac att ccc cag gtc agt tat gcc tcc tcc agc aga ctc ctc agc aac     528
Tyr Ile Pro Gln Val Ser Tyr Ala Ser Ser Ser Arg Leu Leu Ser Asn
                165                 170                 175 aag aat caa ttc aag tct ttc ctc cga acc atc ccc aat gat gag cac     576
Lys Asn Gln Phe Lys Ser Phe Leu Arg Thr Ile Pro Asn Asp Glu His
                180                 185                 190
```

```
cag gcc act gcc atg gca gac atc atc gag tat ttc cgc tgg aac tgg      624
Gln Ala Thr Ala Met Ala Asp Ile Ile Glu Tyr Phe Arg Trp Asn Trp
        195                 200                 205 gtg ggc aca att gca gct gat gac gac tat ggg cgg ccg ggg att gag      672
Val Gly Thr Ile Ala Ala Asp Asp Asp Tyr Gly Arg Pro Gly Ile Glu
    210                 215                 220 aaa ttc cga gag gaa gct gag gaa agg gat atc tgc atc gac ttc agt      720
Lys Phe Arg Glu Glu Ala Glu Glu Arg Asp Ile Cys Ile Asp Phe Ser
225                 230                 235                 240 gaa ctc atc tcc cag tac tct gat gag gaa gag atc cag cat gtg gta      768
Glu Leu Ile Ser Gln Tyr Ser Asp Glu Glu Glu Ile Gln His Val Val
                245                 250                 255 gag gtg att caa aat tcc acg gcc aaa gtc atc gtg gtt ttc tcc agt      816
Glu Val Ile Gln Asn Ser Thr Ala Lys Val Ile Val Val Phe Ser Ser
            260                 265                 270 ggc cca gat ctt gag ccc ctc atc aag gag att gtc cgg cgc aat atc      864
Gly Pro Asp Leu Glu Pro Leu Ile Lys Glu Ile Val Arg Arg Asn Ile
        275                 280                 285 acg ggc aag atc tgg ctg gcc agc gag gcc tgg gcc agc tcc tcc ctg      912
Thr Gly Lys Ile Trp Leu Ala Ser Glu Ala Trp Ala Ser Ser Ser Leu
    290                 295                 300 atc gcc atg cct cag tac ttc cac gtg gtt ggc ggc acc att gga ttc      960
Ile Ala Met Pro Gln Tyr Phe His Val Val Gly Gly Thr Ile Gly Phe
305                 310                 315                 320 gct ctg aag gct ggg cag atc cca ggc ttc cgg gaa ttc ctg aag aag     1008
Ala Leu Lys Ala Gly Gln Ile Pro Gly Phe Arg Glu Phe Leu Lys Lys
                325                 330                 335 gtc cat ccc agg aag tct gtc cac aat ggt ttt gcc aag gag ttt tgg     1056
Val His Pro Arg Lys Ser Val His Asn Gly Phe Ala Lys Glu Phe Trp
            340                 345                 350 gaa gaa aca ttt aac tgc cac ctc caa gaa ggt gca aaa gga cct tta     1104
Glu Glu Thr Phe Asn Cys His Leu Gln Glu Gly Ala Lys Gly Pro Leu
        355                 360                 365 cct gtg gac acc ttt ctg aga ggt cac gaa gaa agt ggc gac agg ttt     1152
Pro Val Asp Thr Phe Leu Arg Gly His Glu Glu Ser Gly Asp Arg Phe
    370                 375                 380 agc aac agc tcg aca gcc ttc cga ccc ctc tgt aca ggg gat gag aac     1200
Ser Asn Ser Ser Thr Ala Phe Arg Pro Leu Cys Thr Gly Asp Glu Asn
385                 390                 395                 400 atc agc agt gtc gag acc cct tac ata gat tac acg cat tta cgg ata     1248
Ile Ser Ser Val Glu Thr Pro Tyr Ile Asp Tyr Thr His Leu Arg Ile
                405                 410                 415 tcc tac aat gtg tac tta gca gtc tac tcc att gcc cac gcc ttg caa     1296
Ser Tyr Asn Val Tyr Leu Ala Val Tyr Ser Ile Ala His Ala Leu Gln
            420                 425                 430 gat ata tat acc tgc tta cct ggg aga ggg ctc ttc acc aat ggc tcc     1344
Asp Ile Tyr Thr Cys Leu Pro Gly Arg Gly Leu Phe Thr Asn Gly Ser
        435                 440                 445 tgt gca gac atc aag aaa gtt gag gcg tgg cag gtc ctg aag cac cta     1392
Cys Ala Asp Ile Lys Lys Val Glu Ala Trp Gln Val Leu Lys His Leu
    450                 455                 460 cgg cat cta aac ttt aca aac aat atg ggg gag cag gtg acc ttt gat     1440
Arg His Leu Asn Phe Thr Asn Asn Met Gly Glu Gln Val Thr Phe Asp
465                 470                 475                 480 gag tgt ggt gac ctg gtg ggg aac tat tcc atc atc aac tgg cac ctc     1488
Glu Cys Gly Asp Leu Val Gly Asn Tyr Ser Ile Ile Asn Trp His Leu
                485                 490                 495 tcc cca gag gat ggc tcc atc gtg ttt aag gaa gtc ggg tat tac aac     1536
Ser Pro Glu Asp Gly Ser Ile Val Phe Lys Glu Val Gly Tyr Tyr Asn
            500                 505                 510
```

```
gtc tat gcc aag aag gga gaa aga ctc ttc atc aac gag gag aaa atc      1584
Val Tyr Ala Lys Lys Gly Glu Arg Leu Phe Ile Asn Glu Glu Lys Ile
        515                 520                 525 ctg tgg agt ggg ttc tcc agg gag gtg ccg cgg tcc cgg tgc tcg cgg      1632
Leu Trp Ser Gly Phe Ser Arg Glu Val Pro Arg Ser Arg Cys Ser Arg
530                 535                 540 cag tgc cag gag ggc cag gtg cgc cgg gtc aag ggg ttc cac tcc tgc      1680
Gln Cys Gln Glu Gly Gln Val Arg Arg Val Lys Gly Phe His Ser Cys
545                 550                 555                 560 tgc tac gac tgt gtg gac tgc gag gcg ggc agc tac cgg caa aac cca      1728
Cys Tyr Asp Cys Val Asp Cys Glu Ala Gly Ser Tyr Arg Gln Asn Pro
                565                 570                 575 gac gac atc gcc tgc acc ttt tgt ggc cag gat gag tgg tcc ccg gag      1776
Asp Asp Ile Ala Cys Thr Phe Cys Gly Gln Asp Glu Trp Ser Pro Glu
            580                 585                 590 cga agc aca cgc tgc ttc cgc cgc agg tct cgg ttc ctg gca tgg ggc      1824
Arg Ser Thr Arg Cys Phe Arg Arg Arg Ser Arg Phe Leu Ala Trp Gly
        595                 600                 605 gag ccg gct gtg ctg ctg ctc ctg ctg agc ctg gcg ctg ggc              1872
Glu Pro Ala Val Leu Leu Leu Leu Leu Leu Ser Leu Ala Leu Gly
610                 615                 620 ctt gtg ctg gct gct ttg ggg ctg ttc gtt cac cat cgg gac agc cca      1920
Leu Val Leu Ala Ala Leu Gly Leu Phe Val His His Arg Asp Ser Pro
625                 630                 635                 640 ctg gtt cag gcc tcg ggg ggg ccc ctg gcc tgc ttt ggc ctg gtg tgc      1968
Leu Val Gln Ala Ser Gly Gly Pro Leu Ala Cys Phe Gly Leu Val Cys
                645                 650                 655 ctg ggc ctg gtc tgc ctc agc gtc ctc ctg ttc cct ggc cag ccc agc      2016
Leu Gly Leu Val Cys Leu Ser Val Leu Leu Phe Pro Gly Gln Pro Ser
            660                 665                 670 cct gcc cga tgc ctg gcc cag cag ccc ttg tcc cac ctc ccg ctc acg      2064
Pro Ala Arg Cys Leu Ala Gln Gln Pro Leu Ser His Leu Pro Leu Thr
        675                 680                 685 ggc tgc ctg agc aca ctc ttc ctg cag gcg gcc gag atc ttc gtg gag      2112
Gly Cys Leu Ser Thr Leu Phe Leu Gln Ala Ala Glu Ile Phe Val Glu
690                 695                 700 tca gaa ctg cct ctg agc tgg gca gac cgg ctg agt ggc tgc ctg cgg      2160
Ser Glu Leu Pro Leu Ser Trp Ala Asp Arg Leu Ser Gly Cys Leu Arg
705                 710                 715                 720 ggg ccc tgg gcc tgg ctg gtg gtg ctg ctg gcc atg ctg gtg gag gtc      2208
Gly Pro Trp Ala Trp Leu Val Val Leu Leu Ala Met Leu Val Glu Val
                725                 730                 735 gca ctg tgc acc tgg tac ctg gtg gcc ttc ccg ccg gag gtg gtg acg      2256
Ala Leu Cys Thr Trp Tyr Leu Val Ala Phe Pro Pro Glu Val Val Thr
            740                 745                 750 gac tgg cac atg ctg ccc acg gag gcg ctg gtg cac tgc cgc aca cgc      2304
Asp Trp His Met Leu Pro Thr Glu Ala Leu Val His Cys Arg Thr Arg
        755                 760                 765 tcc tgg gtc agc ttc ggc cta gcg cac gcc acc aat gcc acg ctg gcc      2352
Ser Trp Val Ser Phe Gly Leu Ala His Ala Thr Asn Ala Thr Leu Ala
770                 775                 780 ttt ctc tgc ttc ctg ggc act ttc ctg gtg cgg agc cag ccg ggc cgc      2400
Phe Leu Cys Phe Leu Gly Thr Phe Leu Val Arg Ser Gln Pro Gly Arg
785                 790                 795                 800 tac aac cgt gcc cgt ggc ctc acc ttt gcc atg ctg gcc tac ttc atc      2448
Tyr Asn Arg Ala Arg Gly Leu Thr Phe Ala Met Leu Ala Tyr Phe Ile
                805                 810                 815 acc tgg gtc tcc ttt gtg ccc ctc ctg gcc aat gtg cag gtg gtc ctc      2496
Thr Trp Val Ser Phe Val Pro Leu Leu Ala Asn Val Gln Val Val Leu
            820                 825                 830
```

```
agg ccc gcc gtg cag atg ggc gcc ctc ctg ctc tgt gtc ctg ggc atc    2544
Arg Pro Ala Val Gln Met Gly Ala Leu Leu Leu Cys Val Leu Gly Ile
    835                 840                 845 ctg gct gcc ttc cac ctg ccc agg tgt tac ctg ctc atg cgg cag cca    2592
Leu Ala Ala Phe His Leu Pro Arg Cys Tyr Leu Leu Met Arg Gln Pro
850                 855                 860 ggg ctc aac acc ccc gag ttc ttc ctg gga ggg cct ggg gat gcc        2640
Gly Leu Asn Thr Pro Glu Phe Phe Leu Gly Gly Pro Gly Asp Ala
865                 870                 875                 880 caa ggc cag aat gac ggg aac aca gga aat cag ggg aaa cat gag tga    2688
Gln Gly Gln Asn Asp Gly Asn Thr Gly Asn Gln Gly Lys His Glu
                885                 890                 895
```

<210> SEQ ID NO 4
<211> LENGTH: 895
<212> TYPE: PRT
<213> ORGANISM: artificial
<220> FEATURE:
<223> OTHER INFORMATION: Synthetic Construct

<400> SEQUENCE: 4

```
Met Ala Phe Tyr Ser Cys Cys Trp Val Leu Leu Ala Leu Thr Trp His
1               5                   10                  15

Thr Ser Ala Tyr Gly Pro Asp Gln Arg Ala Gln Lys Lys Gly Asp Ile
                20                  25                  30

Ile Leu Gly Gly Leu Phe Pro Ile His Phe Gly Val Ala Ala Lys Asp
            35                  40                  45

Gln Asp Leu Lys Ser Arg Pro Glu Ser Val Glu Cys Ile Arg Tyr Asn
        50                  55                  60

Phe Arg Gly Phe Arg Trp Leu Gln Ala Met Ile Phe Ala Ile Glu Glu
65                  70                  75                  80

Ile Asn Ser Ser Pro Ala Leu Leu Pro Asn Leu Thr Leu Gly Tyr Arg
                85                  90                  95

Ile Phe Asp Thr Cys Asn Thr Val Ser Lys Ala Leu Glu Ala Thr Leu
            100                 105                 110

Ser Phe Val Ala Gln Asn Lys Ile Asp Ser Leu Asn Leu Asp Glu Phe
        115                 120                 125

Cys Asn Cys Ser Glu His Ile Pro Ser Thr Ile Ala Val Val Gly Ala
    130                 135                 140

Thr Gly Ser Gly Val Ser Thr Ala Val Ala Asn Leu Leu Gly Leu Phe
145                 150                 155                 160

Tyr Ile Pro Gln Val Ser Tyr Ala Ser Ser Arg Leu Leu Ser Asn
                165                 170                 175

Lys Asn Gln Phe Lys Ser Phe Leu Arg Thr Ile Pro Asn Asp Glu His
            180                 185                 190

Gln Ala Thr Ala Met Ala Asp Ile Ile Glu Tyr Phe Arg Trp Asn Trp
        195                 200                 205

Val Gly Thr Ile Ala Ala Asp Asp Tyr Gly Arg Pro Gly Ile Glu
    210                 215                 220

Lys Phe Arg Glu Glu Ala Glu Glu Arg Asp Ile Cys Ile Asp Phe Ser
225                 230                 235                 240

Glu Leu Ile Ser Gln Tyr Ser Asp Glu Glu Ile Gln His Val Val
                245                 250                 255

Glu Val Ile Gln Asn Ser Thr Ala Lys Val Ile Val Phe Ser Ser
            260                 265                 270

Gly Pro Asp Leu Glu Pro Leu Ile Lys Glu Ile Val Arg Arg Asn Ile
        275                 280                 285
```

```
Thr Gly Lys Ile Trp Leu Ala Ser Glu Ala Trp Ala Ser Ser Ser Leu
        290                 295                 300

Ile Ala Met Pro Gln Tyr Phe His Val Val Gly Thr Ile Gly Phe
305                 310                 315                 320

Ala Leu Lys Ala Gly Gln Ile Pro Gly Phe Arg Glu Phe Leu Lys Lys
                325                 330                 335

Val His Pro Arg Lys Ser Val His Asn Gly Phe Ala Lys Glu Phe Trp
            340                 345                 350

Glu Glu Thr Phe Asn Cys His Leu Gln Gly Ala Lys Gly Pro Leu
        355                 360                 365

Pro Val Asp Thr Phe Leu Arg Gly His Glu Glu Ser Gly Asp Arg Phe
370                 375                 380

Ser Asn Ser Ser Thr Ala Phe Arg Pro Leu Cys Thr Gly Asp Glu Asn
385                 390                 395                 400

Ile Ser Ser Val Glu Thr Pro Tyr Ile Asp Tyr Thr His Leu Arg Ile
                405                 410                 415

Ser Tyr Asn Val Tyr Leu Ala Val Tyr Ser Ile Ala His Ala Leu Gln
            420                 425                 430

Asp Ile Tyr Thr Cys Leu Pro Gly Arg Gly Leu Phe Thr Asn Gly Ser
        435                 440                 445

Cys Ala Asp Ile Lys Lys Val Glu Ala Trp Gln Val Leu Lys His Leu
450                 455                 460

Arg His Leu Asn Phe Thr Asn Asn Met Gly Glu Gln Val Thr Phe Asp
465                 470                 475                 480

Glu Cys Gly Asp Leu Val Gly Asn Tyr Ser Ile Ile Asn Trp His Leu
                485                 490                 495

Ser Pro Glu Asp Gly Ser Ile Val Phe Lys Glu Val Gly Tyr Tyr Asn
            500                 505                 510

Val Tyr Ala Lys Lys Gly Glu Arg Leu Phe Ile Asn Glu Glu Lys Ile
        515                 520                 525

Leu Trp Ser Gly Phe Ser Arg Glu Val Pro Arg Ser Arg Cys Ser Arg
530                 535                 540

Gln Cys Gln Glu Gly Gln Val Arg Arg Val Lys Gly Phe His Ser Cys
545                 550                 555                 560

Cys Tyr Asp Cys Val Asp Cys Glu Ala Gly Ser Tyr Arg Gln Asn Pro
                565                 570                 575

Asp Asp Ile Ala Cys Thr Phe Cys Gly Gln Asp Glu Trp Ser Pro Glu
            580                 585                 590

Arg Ser Thr Arg Cys Phe Arg Arg Ser Arg Phe Leu Ala Trp Gly
        595                 600                 605

Glu Pro Ala Val Leu Leu Leu Leu Leu Leu Ser Leu Ala Leu Gly
610                 615                 620

Leu Val Leu Ala Ala Leu Gly Leu Phe Val His His Arg Asp Ser Pro
625                 630                 635                 640

Leu Val Gln Ala Ser Gly Gly Pro Leu Ala Cys Phe Gly Leu Val Cys
                645                 650                 655

Leu Gly Leu Val Cys Leu Ser Val Leu Leu Phe Pro Gly Gln Pro Ser
            660                 665                 670

Pro Ala Arg Cys Leu Ala Gln Gln Pro Leu Ser His Leu Pro Leu Thr
        675                 680                 685

Gly Cys Leu Ser Thr Leu Phe Leu Gln Ala Ala Glu Ile Phe Val Glu
690                 695                 700

Ser Glu Leu Pro Leu Ser Trp Ala Asp Arg Leu Ser Gly Cys Leu Arg
705                 710                 715                 720
```

```
Gly Pro Trp Ala Trp Leu Val Leu Leu Ala Met Leu Val Glu Val
            725                 730                 735

Ala Leu Cys Thr Trp Tyr Leu Val Ala Phe Pro Pro Glu Val Val Thr
            740                 745                 750

Asp Trp His Met Leu Pro Thr Glu Ala Leu Val His Cys Arg Thr Arg
            755                 760                 765

Ser Trp Val Ser Phe Gly Leu Ala His Ala Thr Asn Ala Thr Leu Ala
            770                 775                 780

Phe Leu Cys Phe Leu Gly Thr Phe Leu Val Arg Ser Gln Pro Gly Arg
785                 790                 795                 800

Tyr Asn Arg Ala Arg Gly Leu Thr Phe Ala Met Leu Ala Tyr Phe Ile
                805                 810                 815

Thr Trp Val Ser Phe Val Pro Leu Leu Ala Asn Val Gln Val Val Leu
                820                 825                 830

Arg Pro Ala Val Gln Met Gly Ala Leu Leu Leu Cys Val Leu Gly Ile
                835                 840                 845

Leu Ala Ala Phe His Leu Pro Arg Cys Tyr Leu Leu Met Arg Gln Pro
    850                 855                 860

Gly Leu Asn Thr Pro Glu Phe Phe Leu Gly Gly Pro Gly Asp Ala
865                 870                 875                 880

Gln Gly Gln Asn Asp Gly Asn Thr Gly Asn Gln Gly Lys His Glu
                885                 890                 895

<210> SEQ ID NO 5
<211> LENGTH: 45
<212> TYPE: DNA
<213> ORGANISM: herpes simplex virus
<220> FEATURE:
<221> NAME/KEY: CDS
<222> LOCATION: (1)..(45)

<400> SEQUENCE: 5 tgc ggc cgc cag cct gaa ctc gct cct gaa gac ccg gaa gat taa        45
Cys Gly Arg Gln Pro Glu Leu Ala Pro Glu Asp Pro Glu Asp
1               5                   10

<210> SEQ ID NO 6
<211> LENGTH: 14
<212> TYPE: PRT
<213> ORGANISM: herpes simplex virus

<400> SEQUENCE: 6

Cys Gly Arg Gln Pro Glu Leu Ala Pro Glu Asp Pro Glu Asp
1               5                   10

<210> SEQ ID NO 7
<211> LENGTH: 2520
<212> TYPE: DNA
<213> ORGANISM: human
<220> FEATURE:
<221> NAME/KEY: CDS
<222> LOCATION: (1)..(2520)

<400> SEQUENCE: 7 atg ggg ccc agg gca aag acc atc tcc tcc ctg ttc ttc ctc cta tgg    48
Met Gly Pro Arg Ala Lys Thr Ile Ser Ser Leu Phe Phe Leu Leu Trp
1               5                   10                  15 gtc ctg gct gag ccg gct gag aac tcg gac ttc tac ctg cct ggg gat   96
Val Leu Ala Glu Pro Ala Glu Asn Ser Asp Phe Tyr Leu Pro Gly Asp
            20                  25                  30 tac ctc ctg ggt ggc ctc ttc tcc ctc cat gcc aac atg aag ggc att  144
```

|       |       |       |       |       |       |       |       |       |       |       |       |       |       |       |       |      |
|-------|-------|-------|-------|-------|-------|-------|-------|-------|-------|-------|-------|-------|-------|-------|-------|------|
| Tyr   | Leu   | Leu   | Gly   | Gly   | Leu   | Phe   | Ser   | Leu   | His   | Ala   | Asn   | Met   | Lys   | Gly   | Ile   |      |
|       |       | 35    |       |       |       |       | 40    |       |       |       |       | 45    |       |       |       |      |

```
gtt cac ctt aac ttc ctg cag gtg ccc atg tgc aag gag tat gaa gtg       192
Val His Leu Asn Phe Leu Gln Val Pro Met Cys Lys Glu Tyr Glu Val
    50                  55                  60 aag gtg ata ggc tac aac ctc atg cag gcc atg cgc ttt gcg gtg gag       240
Lys Val Ile Gly Tyr Asn Leu Met Gln Ala Met Arg Phe Ala Val Glu
65                  70                  75                  80 gag atc aac aat gac agc agc ctg ctg cct ggt gtg ctg ctg ggc tat       288
Glu Ile Asn Asn Asp Ser Ser Leu Leu Pro Gly Val Leu Leu Gly Tyr
                85                  90                  95 gag atc gtg gat gtg tgc tac atc tcc aac aat gtc cag ccg gtg ctc       336
Glu Ile Val Asp Val Cys Tyr Ile Ser Asn Asn Val Gln Pro Val Leu
            100                 105                 110 tac ttc ctg gca cac gag gac aac ctc ctt ccc atc caa gag gac tac       384
Tyr Phe Leu Ala His Glu Asp Asn Leu Leu Pro Ile Gln Glu Asp Tyr
        115                 120                 125 agt aac tac att tcc cgt gtg gtg gct gtc att ggc cct gac aac tcc       432
Ser Asn Tyr Ile Ser Arg Val Val Ala Val Ile Gly Pro Asp Asn Ser
    130                 135                 140 gag tct gtc atg act gtg gcc aac ttc ctc tcc cta ttt ctc ctt cca       480
Glu Ser Val Met Thr Val Ala Asn Phe Leu Ser Leu Phe Leu Leu Pro
145                 150                 155                 160 cag atc acc tac agc gcc atc agc gat gag ctg cga gac aag gtg cgc       528
Gln Ile Thr Tyr Ser Ala Ile Ser Asp Glu Leu Arg Asp Lys Val Arg
                165                 170                 175 ttc ccg gct ttg ctg cgt acc aca ccc agc gcc gac cac cac atc gag       576
Phe Pro Ala Leu Leu Arg Thr Thr Pro Ser Ala Asp His His Ile Glu
            180                 185                 190 gcc atg gtg cag ctg atg ctg cac ttc cgc tgg aac tgg atc att gtg       624
Ala Met Val Gln Leu Met Leu His Phe Arg Trp Asn Trp Ile Ile Val
        195                 200                 205 ctg gtg agc agc gac acc tat ggc cgc gac aat ggc cag ctg ctt ggc       672
Leu Val Ser Ser Asp Thr Tyr Gly Arg Asp Asn Gly Gln Leu Leu Gly
    210                 215                 220 gag cgc gtg gcc cgg cgc gac atc tgc atc gcc ttc cag gag acg ctg       720
Glu Arg Val Ala Arg Arg Asp Ile Cys Ile Ala Phe Gln Glu Thr Leu
225                 230                 235                 240 ccc aca ctg cag ccc aac cag aac atg acg tca gag gag cgc cag cgc       768
Pro Thr Leu Gln Pro Asn Gln Asn Met Thr Ser Glu Glu Arg Gln Arg
                245                 250                 255 ctg gtg acc att gtg gac aag ctg cag cag agc aca gcg cgc gtc gtg       816
Leu Val Thr Ile Val Asp Lys Leu Gln Gln Ser Thr Ala Arg Val Val
            260                 265                 270 gtc gtg ttc tcg ccc gac ctg acc ctg tac cac ttc ttc aat gag gtg       864
Val Val Phe Ser Pro Asp Leu Thr Leu Tyr His Phe Phe Asn Glu Val
        275                 280                 285 ctg cgc cag aac ttc act ggc gcc gtg tgg atc gcc tcc gag tcc tgg       912
Leu Arg Gln Asn Phe Thr Gly Ala Val Trp Ile Ala Ser Glu Ser Trp
    290                 295                 300 gcc atc gac ccg gtc ctg cac aac ctc acg gag ctg cgc cac ttg ggc       960
Ala Ile Asp Pro Val Leu His Asn Leu Thr Glu Leu Arg His Leu Gly
305                 310                 315                 320 acc ttc ctg ggc atc acc atc cag agc gtg ccc atc ccg ggc ttc agt      1008
Thr Phe Leu Gly Ile Thr Ile Gln Ser Val Pro Ile Pro Gly Phe Ser
                325                 330                 335 gag ttc cgc gag tgg ggc cca cag gct ggg ccg cca ccc ctc agc agg      1056
Glu Phe Arg Glu Trp Gly Pro Gln Ala Gly Pro Pro Pro Leu Ser Arg
            340                 345                 350 acc agc cag agc tat acc tgc aac cag gag tgc gac aac tgc ctg aac      1104
Thr Ser Gln Ser Tyr Thr Cys Asn Gln Glu Cys Asp Asn Cys Leu Asn
```

|  |  |  |  |  |  |  |  |  |  |  |  |  |  |  |  |
|---|---|---|---|---|---|---|---|---|---|---|---|---|---|---|---|
| Thr | Ser | Gln | Ser | Tyr | Thr | Cys | Asn | Gln | Glu | Cys | Asp | Asn | Cys | Leu | Asn |
|  | 355 |  |  |  | 360 |  |  |  | 365 |  |  |  |  |  |  |

```
gcc acc ttg tcc ttc aac acc att ctc agg ctc tct ggg gag cgt gtc      1152
Ala Thr Leu Ser Phe Asn Thr Ile Leu Arg Leu Ser Gly Glu Arg Val
    370             375             380 gtc tac agc gtg tac tct gcg gtc tat gct gtg gcc cat gcc ctg cac      1200
Val Tyr Ser Val Tyr Ser Ala Val Tyr Ala Val Ala His Ala Leu His
385             390             395             400 agc ctc ctc ggc tgt gac aaa agc acc tgc acc aag agg gtg gtc tac      1248
Ser Leu Leu Gly Cys Asp Lys Ser Thr Cys Thr Lys Arg Val Val Tyr
            405             410             415 ccc tgg cag ctg ctt gag gag atc tgg aag gtc aac ttc act ctc ctg      1296
Pro Trp Gln Leu Leu Glu Glu Ile Trp Lys Val Asn Phe Thr Leu Leu
        420             425             430 gac cac caa atc ttc ttc gac ccg caa ggg gac gtg gct ctg cac ttg      1344
Asp His Gln Ile Phe Phe Asp Pro Gln Gly Asp Val Ala Leu His Leu
    435             440             445 gag att gtc cag tgg caa tgg gac cgg agc cag aat ccc ttc cag agc      1392
Glu Ile Val Gln Trp Gln Trp Asp Arg Ser Gln Asn Pro Phe Gln Ser
450             455             460 gtc gcc tcc tac tac ccc ctg cag cga cag ctg aag aac atc caa gac      1440
Val Ala Ser Tyr Tyr Pro Leu Gln Arg Gln Leu Lys Asn Ile Gln Asp
465             470             475             480 atc tcc tgg cac acc atc aac aac acg atc cct atg tcc atg tgt tcc      1488
Ile Ser Trp His Thr Ile Asn Asn Thr Ile Pro Met Ser Met Cys Ser
            485             490             495 aag agg tgc cag tca ggg caa aag aag aag cct gtg ggc atc cac gtc      1536
Lys Arg Cys Gln Ser Gly Gln Lys Lys Lys Pro Val Gly Ile His Val
        500             505             510 tgc tgc ttc gag tgc atc gac tgc ctt ccc ggc acc ttc ctc aac cac      1584
Cys Cys Phe Glu Cys Ile Asp Cys Leu Pro Gly Thr Phe Leu Asn His
    515             520             525 act gaa gat gaa tat gaa tgc cag gcc tgc ccg aat aac gag tgg tcc      1632
Thr Glu Asp Glu Tyr Glu Cys Gln Ala Cys Pro Asn Asn Glu Trp Ser
530             535             540 tac cag agt gag acc tcc tgc ttc aag cgg cag ctg gtc ttc ctg gaa      1680
Tyr Gln Ser Glu Thr Ser Cys Phe Lys Arg Gln Leu Val Phe Leu Glu
545             550             555             560 tgg cat gag gca ccc acc atc gct gtg gcc ctg ctg gcc gcc ctg ggc      1728
Trp His Glu Ala Pro Thr Ile Ala Val Ala Leu Leu Ala Ala Leu Gly
            565             570             575 ttc ctc agc acc ctg gcc atc ctg gtg ata ttc tgg agg cac ttc cag      1776
Phe Leu Ser Thr Leu Ala Ile Leu Val Ile Phe Trp Arg His Phe Gln
        580             585             590 aca ccc ata gtt cgc tcg gct ggg ggc ccc atg tgc ttc ctg atg ctg      1824
Thr Pro Ile Val Arg Ser Ala Gly Gly Pro Met Cys Phe Leu Met Leu
    595             600             605 aca ctg ctg ctg gtg gca tac atg gtg gtc ccg gtg tac gtg ggg ccg      1872
Thr Leu Leu Leu Val Ala Tyr Met Val Val Pro Val Tyr Val Gly Pro
610             615             620 ccc aag gtc tcc acc tgc ctc tgc cgc cag gcc ctc ttt ccc ctc tgc      1920
Pro Lys Val Ser Thr Cys Leu Cys Arg Gln Ala Leu Phe Pro Leu Cys
625             630             635             640 ttc aca atc tgc atc tcc tgt atc gcc gtg cgt tct ttc cag atc gtc      1968
Phe Thr Ile Cys Ile Ser Cys Ile Ala Val Arg Ser Phe Gln Ile Val
            645             650             655 tgc gcc ttc aag atg gcc agc cgc ttc cca cgc gcc tac agc tac tgg      2016
Cys Ala Phe Lys Met Ala Ser Arg Phe Pro Arg Ala Tyr Ser Tyr Trp
        660             665             670 gtc cgc tac cag ggg ccc tac gtc tct atg gca ttt atc acg gta ctc      2064
```

```
Val Arg Tyr Gln Gly Pro Tyr Val Ser Met Ala Phe Ile Thr Val Leu
            675                 680                 685 aaa atg gtc att gtg gta att ggc atg ctg gcc acg ggc ctc agt ccc        2112
Lys Met Val Ile Val Val Ile Gly Met Leu Ala Thr Gly Leu Ser Pro
        690                 695                 700 acc acc cgt act gac ccc gat gac ccc aag atc aca att gtc tcc tgt        2160
Thr Thr Arg Thr Asp Pro Asp Asp Pro Lys Ile Thr Ile Val Ser Cys
705                 710                 715                 720 aac ccc aac tac cgc aac agc ctg ctg ttc aac acc agc ctg gac ctg        2208
Asn Pro Asn Tyr Arg Asn Ser Leu Leu Phe Asn Thr Ser Leu Asp Leu
                725                 730                 735 ctg ctc tca gtg gtg ggt ttc agc ttc gcc tac atg ggc aaa gag ctg        2256
Leu Leu Ser Val Val Gly Phe Ser Phe Ala Tyr Met Gly Lys Glu Leu
            740                 745                 750 ccc acc aac tac aac gag gcc aag ttc atc acc ctc agc atg acc ttc        2304
Pro Thr Asn Tyr Asn Glu Ala Lys Phe Ile Thr Leu Ser Met Thr Phe
        755                 760                 765 tat ttc acc tca tct gtc tcc ctc tgc acc ttc atg tct gcc tac agc        2352
Tyr Phe Thr Ser Ser Val Ser Leu Cys Thr Phe Met Ser Ala Tyr Ser
770                 775                 780 ggg gtg ctg gtc acc atc gtg gac ctc ttg gtc act gtg ctc aac ctc        2400
Gly Val Leu Val Thr Ile Val Asp Leu Leu Val Thr Val Leu Asn Leu
                785                 790                 795                 800 ctg gcc atc agc ctg ggc tac ttc ggc ccc aag tgc tac atg atc ctc        2448
Leu Ala Ile Ser Leu Gly Tyr Phe Gly Pro Lys Cys Tyr Met Ile Leu
            805                 810                 815 ttc tac ccg gag cgc aac acg ccc gcc tac ttc aac agc atg atc cag        2496
Phe Tyr Pro Glu Arg Asn Thr Pro Ala Tyr Phe Asn Ser Met Ile Gln
        820                 825                 830 ggc tac acc atg agg agg gac tag                                        2520
Gly Tyr Thr Met Arg Arg Asp
                835

<210> SEQ ID NO 8
<211> LENGTH: 839
<212> TYPE: PRT
<213> ORGANISM: human

<400> SEQUENCE: 8

Met Gly Pro Arg Ala Lys Thr Ile Ser Ser Leu Phe Phe Leu Leu Trp
1               5                   10                  15

Val Leu Ala Glu Pro Ala Glu Asn Ser Asp Phe Tyr Leu Pro Gly Asp
            20                  25                  30

Tyr Leu Leu Gly Gly Leu Phe Ser Leu His Ala Asn Met Lys Gly Ile
        35                  40                  45

Val His Leu Asn Phe Leu Gln Val Pro Met Cys Lys Glu Tyr Glu Val
    50                  55                  60

Lys Val Ile Gly Tyr Asn Leu Met Gln Ala Met Arg Phe Ala Val Glu
65                  70                  75                  80

Glu Ile Asn Asn Asp Ser Ser Leu Leu Pro Gly Val Leu Leu Gly Tyr
                85                  90                  95

Glu Ile Val Asp Val Cys Tyr Ile Ser Asn Asn Val Gln Pro Val Leu
            100                 105                 110

Tyr Phe Leu Ala His Glu Asp Asn Leu Leu Pro Ile Gln Glu Asp Tyr
        115                 120                 125

Ser Asn Tyr Ile Ser Arg Val Val Ala Val Ile Gly Pro Asp Asn Ser
    130                 135                 140

Glu Ser Val Met Thr Val Ala Asn Phe Leu Ser Leu Phe Leu Leu Pro
145                 150                 155                 160
```

```
Gln Ile Thr Tyr Ser Ala Ile Ser Asp Glu Leu Arg Asp Lys Val Arg
                165                 170                 175

Phe Pro Ala Leu Leu Arg Thr Thr Pro Ser Ala Asp His His Ile Glu
            180                 185                 190

Ala Met Val Gln Leu Met Leu His Phe Arg Trp Asn Trp Ile Ile Val
                195                 200                 205

Leu Val Ser Ser Asp Thr Tyr Gly Arg Asp Asn Gly Gln Leu Leu Gly
            210                 215                 220

Glu Arg Val Ala Arg Arg Asp Ile Cys Ile Ala Phe Gln Glu Thr Leu
225                 230                 235                 240

Pro Thr Leu Gln Pro Asn Gln Asn Met Thr Ser Glu Glu Arg Gln Arg
                245                 250                 255

Leu Val Thr Ile Val Asp Lys Leu Gln Gln Ser Thr Ala Arg Val Val
                260                 265                 270

Val Val Phe Ser Pro Asp Leu Thr Leu Tyr His Phe Phe Asn Glu Val
            275                 280                 285

Leu Arg Gln Asn Phe Thr Gly Ala Val Trp Ile Ala Ser Glu Ser Trp
290                 295                 300

Ala Ile Asp Pro Val Leu His Asn Leu Thr Glu Leu Arg His Leu Gly
305                 310                 315                 320

Thr Phe Leu Gly Ile Thr Ile Gln Ser Val Pro Ile Pro Gly Phe Ser
                325                 330                 335

Glu Phe Arg Glu Trp Gly Pro Gln Ala Gly Pro Pro Leu Ser Arg
            340                 345                 350

Thr Ser Gln Ser Tyr Thr Cys Asn Gln Glu Cys Asp Asn Cys Leu Asn
                355                 360                 365

Ala Thr Leu Ser Phe Asn Thr Ile Leu Arg Leu Ser Gly Glu Arg Val
            370                 375                 380

Val Tyr Ser Val Tyr Ser Ala Val Tyr Ala Val Ala His Ala Leu His
385                 390                 395                 400

Ser Leu Leu Gly Cys Asp Lys Ser Thr Cys Thr Lys Arg Val Val Tyr
                405                 410                 415

Pro Trp Gln Leu Leu Glu Glu Ile Trp Lys Val Asn Phe Thr Leu Leu
            420                 425                 430

Asp His Gln Ile Phe Phe Asp Pro Gln Gly Asp Val Ala Leu His Leu
            435                 440                 445

Glu Ile Val Gln Trp Gln Trp Asp Arg Ser Gln Asn Pro Phe Gln Ser
450                 455                 460

Val Ala Ser Tyr Tyr Pro Leu Gln Arg Gln Leu Lys Asn Ile Gln Asp
465                 470                 475                 480

Ile Ser Trp His Thr Ile Asn Asn Thr Ile Pro Met Ser Met Cys Ser
                485                 490                 495

Lys Arg Cys Gln Ser Gly Gln Lys Lys Lys Pro Val Gly Ile His Val
            500                 505                 510

Cys Cys Phe Glu Cys Ile Asp Cys Leu Pro Gly Thr Phe Leu Asn His
            515                 520                 525

Thr Glu Asp Glu Tyr Glu Cys Gln Ala Cys Pro Asn Asn Glu Trp Ser
            530                 535                 540

Tyr Gln Ser Glu Thr Ser Cys Phe Lys Arg Gln Leu Val Phe Leu Glu
545                 550                 555                 560

Trp His Glu Ala Pro Thr Ile Ala Val Ala Leu Leu Ala Ala Leu Gly
                565                 570                 575

Phe Leu Ser Thr Leu Ala Ile Leu Val Ile Phe Trp Arg His Phe Gln
```

```
                    580                 585                 590
Thr Pro Ile Val Arg Ser Ala Gly Gly Pro Met Cys Phe Leu Met Leu
        595                 600                 605

Thr Leu Leu Leu Val Ala Tyr Met Val Val Pro Val Tyr Val Gly Pro
        610                 615                 620

Pro Lys Val Ser Thr Cys Leu Cys Arg Gln Ala Leu Phe Pro Leu Cys
625                 630                 635                 640

Phe Thr Ile Cys Ile Ser Cys Ile Ala Val Arg Ser Phe Gln Ile Val
                645                 650                 655

Cys Ala Phe Lys Met Ala Ser Arg Phe Pro Arg Ala Tyr Ser Tyr Trp
            660                 665                 670

Val Arg Tyr Gln Gly Pro Tyr Val Ser Met Ala Phe Ile Thr Val Leu
        675                 680                 685

Lys Met Val Ile Val Ile Gly Met Leu Ala Thr Gly Leu Ser Pro
        690                 695                 700

Thr Thr Arg Thr Asp Pro Asp Pro Lys Ile Thr Ile Val Ser Cys
705                 710                 715                 720

Asn Pro Asn Tyr Arg Asn Ser Leu Leu Phe Asn Thr Ser Leu Asp Leu
                725                 730                 735

Leu Leu Ser Val Val Gly Phe Ser Phe Ala Tyr Met Gly Lys Glu Leu
            740                 745                 750

Pro Thr Asn Tyr Asn Glu Ala Lys Phe Ile Thr Leu Ser Met Thr Phe
        755                 760                 765

Tyr Phe Thr Ser Ser Val Ser Leu Cys Thr Phe Met Ser Ala Tyr Ser
        770                 775                 780

Gly Val Leu Val Thr Ile Val Asp Leu Leu Val Thr Val Leu Asn Leu
785                 790                 795                 800

Leu Ala Ile Ser Leu Gly Tyr Phe Gly Pro Lys Cys Tyr Met Ile Leu
                805                 810                 815

Phe Tyr Pro Glu Arg Asn Thr Pro Ala Tyr Phe Asn Ser Met Ile Gln
            820                 825                 830

Gly Tyr Thr Met Arg Arg Asp
        835

<210> SEQ ID NO 9
<211> LENGTH: 2559
<212> TYPE: DNA
<213> ORGANISM: human
<220> FEATURE:
<221> NAME/KEY: CDS
<222> LOCATION: (1)..(2559)

<400> SEQUENCE: 9 atg ctg ggc cct gct gtc ctg ggc ctc agc ctc tgg gct ctc ctg cac        48
Met Leu Gly Pro Ala Val Leu Gly Leu Ser Leu Trp Ala Leu Leu His
1               5                   10                  15 cct ggg acg ggg gcc cca ttg tgc ctg tca cag caa ctt agg atg aag        96
Pro Gly Thr Gly Ala Pro Leu Cys Leu Ser Gln Gln Leu Arg Met Lys
            20                  25                  30 ggg gac tac gtg ctg ggg ggg ctg ttc ccc ctg ggc gag gcc gag gag       144
Gly Asp Tyr Val Leu Gly Gly Leu Phe Pro Leu Gly Glu Ala Glu Glu
        35                  40                  45 gct ggc ctc cgc agc cgg aca cgg ccc agc agc cct gtg tgc acc agg       192
Ala Gly Leu Arg Ser Arg Thr Arg Pro Ser Ser Pro Val Cys Thr Arg
    50                  55                  60 ttc tcc tca aac ggc ctg ctc tgg gca ctg gcc atg aaa atg gcc gtg       240
Phe Ser Ser Asn Gly Leu Leu Trp Ala Leu Ala Met Lys Met Ala Val
65                  70                  75                  80
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| gag | gag | atc | aac | aac | aag | tcg | gat | ctg | ctg | ccc | ggg | ctg | cgc | ctg | ggc | 288  |
| Glu | Glu | Ile | Asn | Asn | Lys | Ser | Asp | Leu | Leu | Pro | Gly | Leu | Arg | Leu | Gly |      |
|     |     |     |     | 85  |     |     |     |     | 90  |     |     |     |     | 95  |     |      |
| tac | gac | ctc | ttt | gat | acg | tgc | tcg | gag | cct | gtg | gtg | gcc | atg | aag | ccc | 336  |
| Tyr | Asp | Leu | Phe | Asp | Thr | Cys | Ser | Glu | Pro | Val | Val | Ala | Met | Lys | Pro |      |
|     |     |     |     | 100 |     |     |     |     | 105 |     |     |     |     | 110 |     |      |
| agc | ctc | atg | ttc | ctg | gcc | aag | gca | ggc | agc | cgc | gac | atc | gcc | gcc | tac | 384  |
| Ser | Leu | Met | Phe | Leu | Ala | Lys | Ala | Gly | Ser | Arg | Asp | Ile | Ala | Ala | Tyr |      |
|     |     |     | 115 |     |     |     |     | 120 |     |     |     |     | 125 |     |     |      |
| tgc | aac | tac | acg | cag | tac | cag | ccc | cgt | gtg | ctg | gct | gtc | atc | ggg | ccc | 432  |
| Cys | Asn | Tyr | Thr | Gln | Tyr | Gln | Pro | Arg | Val | Leu | Ala | Val | Ile | Gly | Pro |      |
|     | 130 |     |     |     |     | 135 |     |     |     |     | 140 |     |     |     |     |      |
| cac | tcg | tca | gag | ctc | gcc | atg | gtc | acc | ggc | aag | ttc | ttc | agc | ttc | ttc | 480  |
| His | Ser | Ser | Glu | Leu | Ala | Met | Val | Thr | Gly | Lys | Phe | Phe | Ser | Phe | Phe |      |
| 145 |     |     |     |     | 150 |     |     |     |     | 155 |     |     |     |     | 160 |      |
| ctc | atg | ccc | cag | gtc | agc | tac | ggt | gct | agc | atg | gag | ctg | ctg | agc | gcc | 528  |
| Leu | Met | Pro | Gln | Val | Ser | Tyr | Gly | Ala | Ser | Met | Glu | Leu | Leu | Ser | Ala |      |
|     |     |     |     | 165 |     |     |     |     | 170 |     |     |     |     | 175 |     |      |
| cgg | gag | acc | ttc | ccc | tcc | ttc | ttc | cgc | acc | gtg | ccc | agc | gac | cgt | gtg | 576  |
| Arg | Glu | Thr | Phe | Pro | Ser | Phe | Phe | Arg | Thr | Val | Pro | Ser | Asp | Arg | Val |      |
|     |     |     | 180 |     |     |     |     | 185 |     |     |     |     | 190 |     |     |      |
| cag | ctg | acg | gcc | gcc | gcg | gag | ctg | ctg | cag | gag | ttc | ggc | tgg | aac | tgg | 624  |
| Gln | Leu | Thr | Ala | Ala | Ala | Glu | Leu | Leu | Gln | Glu | Phe | Gly | Trp | Asn | Trp |      |
|     | 195 |     |     |     |     | 200 |     |     |     |     | 205 |     |     |     |     |      |
| gtg | gcc | gcc | ctg | ggc | agc | gac | gac | gag | tac | ggc | cgg | cag | ggc | ctg | agc | 672  |
| Val | Ala | Ala | Leu | Gly | Ser | Asp | Asp | Glu | Tyr | Gly | Arg | Gln | Gly | Leu | Ser |      |
| 210 |     |     |     |     | 215 |     |     |     |     | 220 |     |     |     |     |     |      |
| atc | ttc | tcg | gcc | ctg | gcc | gcg | gca | cgc | ggc | atc | tgc | atc | gcg | cac | gag | 720  |
| Ile | Phe | Ser | Ala | Leu | Ala | Ala | Ala | Arg | Gly | Ile | Cys | Ile | Ala | His | Glu |      |
| 225 |     |     |     | 230 |     |     |     |     | 235 |     |     |     |     | 240 |     |      |
| ggc | ctg | gtg | ccg | ctg | ccc | cgt | gcc | gat | gac | tcg | cgg | ctg | ggg | aag | gtg | 768  |
| Gly | Leu | Val | Pro | Leu | Pro | Arg | Ala | Asp | Asp | Ser | Arg | Leu | Gly | Lys | Val |      |
|     |     |     |     | 245 |     |     |     |     | 250 |     |     |     |     | 255 |     |      |
| cag | gac | gtc | ctg | cac | cag | gtg | aac | cag | agc | agc | gtg | cag | gtg | gtg | ctg | 816  |
| Gln | Asp | Val | Leu | His | Gln | Val | Asn | Gln | Ser | Ser | Val | Gln | Val | Val | Leu |      |
|     |     |     |     | 260 |     |     |     |     | 265 |     |     |     |     | 270 |     |      |
| ctg | ttc | gcc | tcc | gtg | cac | gcc | gcc | cac | gcc | ctc | ttc | aac | tac | agc | atc | 864  |
| Leu | Phe | Ala | Ser | Val | His | Ala | Ala | His | Ala | Leu | Phe | Asn | Tyr | Ser | Ile |      |
|     | 275 |     |     |     |     | 280 |     |     |     |     | 285 |     |     |     |     |      |
| agc | agc | agg | ctc | tcg | ccc | aag | gtg | tgg | gtg | gcc | agc | gag | gcc | tgg | ctg | 912  |
| Ser | Ser | Arg | Leu | Ser | Pro | Lys | Val | Trp | Val | Ala | Ser | Glu | Ala | Trp | Leu |      |
|     | 290 |     |     |     |     | 295 |     |     |     |     | 300 |     |     |     |     |      |
| acc | tct | gac | ctg | gtc | atg | ggg | ctg | ccc | ggc | atg | gcc | cag | atg | ggc | acg | 960  |
| Thr | Ser | Asp | Leu | Val | Met | Gly | Leu | Pro | Gly | Met | Ala | Gln | Met | Gly | Thr |      |
| 305 |     |     |     |     | 310 |     |     |     |     | 315 |     |     |     |     | 320 |      |
| gtg | ctt | ggc | ttc | ctc | cag | agg | ggt | gcc | cag | ctg | cac | gag | ttc | ccc | cag | 1008 |
| Val | Leu | Gly | Phe | Leu | Gln | Arg | Gly | Ala | Gln | Leu | His | Glu | Phe | Pro | Gln |      |
|     |     |     |     | 325 |     |     |     |     | 330 |     |     |     |     | 335 |     |      |
| tac | gtg | aag | acg | cac | ctg | gcc | ctg | gcc | acc | gac | ccg | gcc | ttc | tgc | tct | 1056 |
| Tyr | Val | Lys | Thr | His | Leu | Ala | Leu | Ala | Thr | Asp | Pro | Ala | Phe | Cys | Ser |      |
|     |     |     | 340 |     |     |     |     | 345 |     |     |     |     | 350 |     |     |      |
| gcc | ctg | ggc | gag | agg | gag | cag | ggt | ctg | gag | gag | gac | gtg | gtg | ggc | cag | 1104 |
| Ala | Leu | Gly | Glu | Arg | Glu | Gln | Gly | Leu | Glu | Glu | Asp | Val | Val | Gly | Gln |      |
|     |     | 355 |     |     |     |     | 360 |     |     |     |     | 365 |     |     |     |      |
| cgc | tgc | ccg | cag | tgt | gac | tgc | atc | acg | ctg | cag | aac | gtg | agc | gca | ggg | 1152 |
| Arg | Cys | Pro | Gln | Cys | Asp | Cys | Ile | Thr | Leu | Gln | Asn | Val | Ser | Ala | Gly |      |
|     | 370 |     |     |     |     | 375 |     |     |     |     | 380 |     |     |     |     |      |
| cta | aat | cac | cac | cag | acg | ttc | tct | gtc | tac | gca | gct | gtg | tat | agc | gtg | 1200 |
| Leu | Asn | His | His | Gln | Thr | Phe | Ser | Val | Tyr | Ala | Ala | Val | Tyr | Ser | Val |      |
| 385 |     |     |     |     | 390 |     |     |     |     | 395 |     |     |     |     | 400 |      |

-continued

| | |
|---|---|
| gcc cag gcc ctg cac aac act ctt cag tgc aac gcc tca ggc tgc ccc<br>Ala Gln Ala Leu His Asn Thr Leu Gln Cys Asn Ala Ser Gly Cys Pro<br>405                   410               415 | 1248 |
| gcg cag gac ccc gtg aag ccc tgg cag ctc ctg gag aac atg tac aac<br>Ala Gln Asp Pro Val Lys Pro Trp Gln Leu Leu Glu Asn Met Tyr Asn<br>420                 425               430 | 1296 |
| ctg acc ttc cac gtg ggc ggg ctg ccg ctg cgg ttc gac agc agc gga<br>Leu Thr Phe His Val Gly Gly Leu Pro Leu Arg Phe Asp Ser Ser Gly<br>435                   440               445 | 1344 |
| aac gtg gac atg gag tac gac ctg aag ctg tgg gtg tgg cag ggc tca<br>Asn Val Asp Met Glu Tyr Asp Leu Lys Leu Trp Val Trp Gln Gly Ser<br>450                 455               460 | 1392 |
| gtg ccc agg ctc cac gac gtg ggc agg ttc aac ggc agc ctc agg aca<br>Val Pro Arg Leu His Asp Val Gly Arg Phe Asn Gly Ser Leu Arg Thr<br>465                   470               475               480 | 1440 |
| gag cgc ctg aag atc cgc tgg cac acg tct gac aac cag aag ccc gtg<br>Glu Arg Leu Lys Ile Arg Trp His Thr Ser Asp Asn Gln Lys Pro Val<br>485                 490               495 | 1488 |
| tcc cgg tgc tcg cgg cag tgc cag gag ggc cag gtg cgc cgg gtc aag<br>Ser Arg Cys Ser Arg Gln Cys Gln Glu Gly Gln Val Arg Arg Val Lys<br>500                 505               510 | 1536 |
| ggg ttc cac tcc tgc tgc tac gac tgt gtg gac tgc gag gcg ggc agc<br>Gly Phe His Ser Cys Cys Tyr Asp Cys Val Asp Cys Glu Ala Gly Ser<br>515                   520               525 | 1584 |
| tac cgg caa aac cca gac gac atc gcc tgc acc ttt tgt ggc cag gat<br>Tyr Arg Gln Asn Pro Asp Asp Ile Ala Cys Thr Phe Cys Gly Gln Asp<br>530                 535               540 | 1632 |
| gag tgg tcc ccg gag cga agc aca cgc tgc ttc cgc cgc agg tct cgg<br>Glu Trp Ser Pro Glu Arg Ser Thr Arg Cys Phe Arg Arg Arg Ser Arg<br>545                 550               555               560 | 1680 |
| ttc ctg gca tgg ggc gag ccg gct gtg ctg ctg ctc ctg ctg ctg<br>Phe Leu Ala Trp Gly Glu Pro Ala Val Leu Leu Leu Leu Leu Leu<br>565                   570               575 | 1728 |
| agc ctg gcg ctg ggc ctt gtg ctg gct gct ttg ggg ctg ttc gtt cac<br>Ser Leu Ala Leu Gly Leu Val Leu Ala Ala Leu Gly Leu Phe Val His<br>580                 585               590 | 1776 |
| cat cgg gac agc cca ctg gtt cag gcc tcg ggg ggg ccc ctg gcc tgc<br>His Arg Asp Ser Pro Leu Val Gln Ala Ser Gly Gly Pro Leu Ala Cys<br>595                 600               605 | 1824 |
| ttt ggc ctg gtg tgc ctg ggc ctg gtc tgc ctc agc gtc ctc ctg ttc<br>Phe Gly Leu Val Cys Leu Gly Leu Val Cys Leu Ser Val Leu Leu Phe<br>610                 615               620 | 1872 |
| cct ggc cag ccc agc cct gcc cga tgc ctg gcc cag cag ccc ttg tcc<br>Pro Gly Gln Pro Ser Pro Ala Arg Cys Leu Ala Gln Gln Pro Leu Ser<br>625                 630               635               640 | 1920 |
| cac ctc ccg ctc acg ggc tgc ctg agc aca ctc ttc ctg cag gcg gcc<br>His Leu Pro Leu Thr Gly Cys Leu Ser Thr Leu Phe Leu Gln Ala Ala<br>645                 650               655 | 1968 |
| gag atc ttc gtg gag tca gaa ctg cct ctg agc tgg gca gac cgg ctg<br>Glu Ile Phe Val Glu Ser Glu Leu Pro Leu Ser Trp Ala Asp Arg Leu<br>660                 665               670 | 2016 |
| agt ggc tgc ctg cgg ggg ccc tgg gcc tgg ctg gtg gtg ctg ctg gcc<br>Ser Gly Cys Leu Arg Gly Pro Trp Ala Trp Leu Val Val Leu Leu Ala<br>675                 680               685 | 2064 |
| atg ctg gtg gag gtc gca ctg tgc acc tgg tac ctg gtg gcc ttc ccg<br>Met Leu Val Glu Val Ala Leu Cys Thr Trp Tyr Leu Val Ala Phe Pro<br>690                 695               700 | 2112 |
| ccg gag gtg gtg acg gac tgg cac atg ctg ccc acg gag gcg ctg gtg<br>Pro Glu Val Val Thr Asp Trp His Met Leu Pro Thr Glu Ala Leu Val<br>705                 710               715               720 | 2160 |

```
cac tgc cgc aca cgc tcc tgg gtc agc ttc ggc cta gcg cac gcc acc      2208
His Cys Arg Thr Arg Ser Trp Val Ser Phe Gly Leu Ala His Ala Thr
                725                 730                 735 aat gcc acg ctg gcc ttt ctc tgc ttc ctg ggc act ttc ctg gtg cgg      2256
Asn Ala Thr Leu Ala Phe Leu Cys Phe Leu Gly Thr Phe Leu Val Arg
            740                 745                 750 agc cag ccg ggc cgc tac aac cgt gcc cgt ggc ctc acc ttt gcc atg      2304
Ser Gln Pro Gly Arg Tyr Asn Arg Ala Arg Gly Leu Thr Phe Ala Met
        755                 760                 765 ctg gcc tac ttc atc acc tgg gtc tcc ttt gtg ccc ctc ctg gcc aat      2352
Leu Ala Tyr Phe Ile Thr Trp Val Ser Phe Val Pro Leu Leu Ala Asn
    770                 775                 780 gtg cag gtg gtc ctc agg ccc gcc gtg cag atg ggc gcc ctc ctg ctc      2400
Val Gln Val Val Leu Arg Pro Ala Val Gln Met Gly Ala Leu Leu Leu
785                 790                 795                 800 tgt gtc ctg ggc atc ctg gct gcc ttc cac ctg ccc agg tgt tac ctg      2448
Cys Val Leu Gly Ile Leu Ala Ala Phe His Leu Pro Arg Cys Tyr Leu
                805                 810                 815 ctc atg cgg cag cca ggg ctc aac acc ccc gag ttc ttc ctg gga ggg      2496
Leu Met Arg Gln Pro Gly Leu Asn Thr Pro Glu Phe Phe Leu Gly Gly
            820                 825                 830 ggc cct ggg gat gcc caa ggc cag aat gac ggg aac aca gga aat cag      2544
Gly Pro Gly Asp Ala Gln Gly Gln Asn Asp Gly Asn Thr Gly Asn Gln
        835                 840                 845 ggg aaa cat gag tga                                                  2559
Gly Lys His Glu
    850

<210> SEQ ID NO 10
<211> LENGTH: 852
<212> TYPE: PRT
<213> ORGANISM: human

<400> SEQUENCE: 10

Met Leu Gly Pro Ala Val Leu Gly Leu Ser Leu Trp Ala Leu Leu His
1               5                   10                  15

Pro Gly Thr Gly Ala Pro Leu Cys Leu Ser Gln Gln Leu Arg Met Lys
            20                  25                  30

Gly Asp Tyr Val Leu Gly Gly Leu Phe Pro Leu Gly Glu Ala Glu Glu
        35                  40                  45

Ala Gly Leu Arg Ser Arg Thr Arg Pro Ser Ser Pro Val Cys Thr Arg
    50                  55                  60

Phe Ser Ser Asn Gly Leu Leu Trp Ala Leu Ala Met Lys Met Ala Val
65                  70                  75                  80

Glu Glu Ile Asn Asn Lys Ser Asp Leu Leu Pro Gly Leu Arg Leu Gly
                85                  90                  95

Tyr Asp Leu Phe Asp Thr Cys Ser Glu Pro Val Val Ala Met Lys Pro
            100                 105                 110

Ser Leu Met Phe Leu Ala Lys Ala Gly Ser Arg Asp Ile Ala Ala Tyr
        115                 120                 125

Cys Asn Tyr Thr Gln Tyr Gln Pro Arg Val Leu Ala Val Ile Gly Pro
    130                 135                 140

His Ser Ser Glu Leu Ala Met Val Thr Gly Lys Phe Phe Ser Phe Phe
145                 150                 155                 160

Leu Met Pro Gln Val Ser Tyr Gly Ala Ser Met Glu Leu Leu Ser Ala
                165                 170                 175

Arg Glu Thr Phe Pro Ser Phe Phe Arg Thr Val Pro Ser Asp Arg Val
            180                 185                 190
```

-continued

```
Gln Leu Thr Ala Ala Ala Glu Leu Leu Gln Glu Phe Gly Trp Asn Trp
            195                 200                 205
Val Ala Ala Leu Gly Ser Asp Asp Glu Tyr Gly Arg Gln Gly Leu Ser
        210                 215                 220
Ile Phe Ser Ala Leu Ala Ala Arg Gly Ile Cys Ile Ala His Glu
225                 230                 235                 240
Gly Leu Val Pro Leu Pro Arg Ala Asp Asp Ser Arg Leu Gly Lys Val
                245                 250                 255
Gln Asp Val Leu His Gln Val Asn Gln Ser Ser Val Gln Val Val Leu
            260                 265                 270
Leu Phe Ala Ser Val His Ala Ala His Ala Leu Phe Asn Tyr Ser Ile
        275                 280                 285
Ser Ser Arg Leu Ser Pro Lys Val Trp Val Ala Ser Glu Ala Trp Leu
    290                 295                 300
Thr Ser Asp Leu Val Met Gly Leu Pro Gly Met Ala Gln Met Gly Thr
305                 310                 315                 320
Val Leu Gly Phe Leu Gln Arg Gly Ala Gln Leu His Glu Phe Pro Gln
                325                 330                 335
Tyr Val Lys Thr His Leu Ala Leu Ala Thr Asp Pro Ala Phe Cys Ser
            340                 345                 350
Ala Leu Gly Glu Arg Glu Gln Gly Leu Glu Glu Asp Val Val Gly Gln
        355                 360                 365
Arg Cys Pro Gln Cys Asp Cys Ile Thr Leu Gln Asn Val Ser Ala Gly
    370                 375                 380
Leu Asn His His Gln Thr Phe Ser Val Tyr Ala Ala Val Tyr Ser Val
385                 390                 395                 400
Ala Gln Ala Leu His Asn Thr Leu Gln Cys Asn Ala Ser Gly Cys Pro
                405                 410                 415
Ala Gln Asp Pro Val Lys Pro Trp Gln Leu Leu Glu Asn Met Tyr Asn
            420                 425                 430
Leu Thr Phe His Val Gly Gly Leu Pro Leu Arg Phe Asp Ser Ser Gly
        435                 440                 445
Asn Val Asp Met Glu Tyr Asp Leu Lys Leu Trp Val Trp Gln Gly Ser
    450                 455                 460
Val Pro Arg Leu His Asp Val Gly Arg Phe Asn Gly Ser Leu Arg Thr
465                 470                 475                 480
Glu Arg Leu Lys Ile Arg Trp His Thr Ser Asp Asn Gln Lys Pro Val
                485                 490                 495
Ser Arg Cys Ser Arg Gln Cys Gln Glu Gly Gln Val Arg Arg Val Lys
            500                 505                 510
Gly Phe His Ser Cys Cys Tyr Asp Cys Val Asp Cys Glu Ala Gly Ser
        515                 520                 525
Tyr Arg Gln Asn Pro Asp Asp Ile Ala Cys Thr Phe Cys Gly Gln Asp
    530                 535                 540
Glu Trp Ser Pro Glu Arg Ser Thr Arg Cys Phe Arg Arg Ser Arg
545                 550                 555                 560
Phe Leu Ala Trp Gly Glu Pro Ala Val Leu Leu Leu Leu Leu Leu Leu
                565                 570                 575
Ser Leu Ala Leu Gly Leu Val Leu Ala Ala Leu Gly Leu Phe Val His
            580                 585                 590
His Arg Asp Ser Pro Leu Val Gln Ala Ser Gly Gly Pro Leu Ala Cys
        595                 600                 605
Phe Gly Leu Val Cys Leu Gly Leu Val Cys Leu Ser Val Leu Leu Phe
```

```
                610             615             620
Pro Gly Gln Pro Ser Pro Ala Arg Cys Leu Ala Gln Gln Pro Leu Ser
625             630             635             640

His Leu Pro Leu Thr Gly Cys Leu Ser Thr Leu Phe Leu Gln Ala Ala
                645             650             655

Glu Ile Phe Val Glu Ser Glu Leu Pro Leu Ser Trp Ala Asp Arg Leu
                660             665             670

Ser Gly Cys Leu Arg Gly Pro Trp Ala Trp Leu Val Val Leu Leu Ala
                675             680             685

Met Leu Val Glu Val Ala Leu Cys Thr Trp Tyr Leu Val Ala Phe Pro
690             695             700

Pro Glu Val Val Thr Asp Trp His Met Leu Pro Thr Glu Ala Leu Val
705             710             715             720

His Cys Arg Thr Arg Ser Trp Val Ser Phe Gly Leu Ala His Ala Thr
                725             730             735

Asn Ala Thr Leu Ala Phe Leu Cys Phe Leu Gly Thr Phe Leu Val Arg
                740             745             750

Ser Gln Pro Gly Arg Tyr Asn Arg Ala Arg Gly Leu Thr Phe Ala Met
                755             760             765

Leu Ala Tyr Phe Ile Thr Trp Val Ser Phe Val Pro Leu Leu Ala Asn
770             775             780

Val Gln Val Val Leu Arg Pro Ala Val Gln Met Gly Ala Leu Leu Leu
785             790             795             800

Cys Val Leu Gly Ile Leu Ala Ala Phe His Leu Pro Arg Cys Tyr Leu
                805             810             815

Leu Met Arg Gln Pro Gly Leu Asn Thr Pro Glu Phe Phe Leu Gly Gly
                820             825             830

Gly Pro Gly Asp Ala Gln Gly Gln Asn Asp Gly Asn Thr Gly Asn Gln
                835             840             845

Gly Lys His Glu
    850

<210> SEQ ID NO 11
<211> LENGTH: 3237
<212> TYPE: DNA
<213> ORGANISM: human
<220> FEATURE:
<221> NAME/KEY: CDS
<222> LOCATION: (1)..(3237)

<400> SEQUENCE: 11 atg gca ttt tat agc tgc tgc tgg gtc ctc ttg gca ctc acc tgg cac       48
Met Ala Phe Tyr Ser Cys Cys Trp Val Leu Leu Ala Leu Thr Trp His
1               5                   10                  15 acc tct gcc tac ggg cca gac cag cga gcc caa aag aag ggg gac att       96
Thr Ser Ala Tyr Gly Pro Asp Gln Arg Ala Gln Lys Lys Gly Asp Ile
                20                  25                  30 atc ctt ggg ggg ctc ttt cct att cat ttt gga gta gca gct aaa gat      144
Ile Leu Gly Gly Leu Phe Pro Ile His Phe Gly Val Ala Ala Lys Asp
            35                  40                  45 caa gat ctc aaa tca agg ccg gag tct gtg gaa tgt atc agg tat aat      192
Gln Asp Leu Lys Ser Arg Pro Glu Ser Val Glu Cys Ile Arg Tyr Asn
        50                  55                  60 ttc cgt ggg ttt cgc tgg tta cag gct atg ata ttt gcc ata gag gag      240
Phe Arg Gly Phe Arg Trp Leu Gln Ala Met Ile Phe Ala Ile Glu Glu
65                  70                  75                  80 ata aac agc agc cca gcc ctt ctt ccc aac ttg acg ctg gga tac agg      288
Ile Asn Ser Ser Pro Ala Leu Leu Pro Asn Leu Thr Leu Gly Tyr Arg
```

```
                         85                  90                  95
ata ttt gac act tgc aac acc gtt tct aag gcc ttg gaa gcc acc ctg    336
Ile Phe Asp Thr Cys Asn Thr Val Ser Lys Ala Leu Glu Ala Thr Leu
            100                 105                 110 agt ttt gtt gct caa aac aaa att gat tct ttg aac ctt gat gag ttc    384
Ser Phe Val Ala Gln Asn Lys Ile Asp Ser Leu Asn Leu Asp Glu Phe
        115                 120                 125 tgc aac tgc tca gag cac att ccc tct acg att gct gtg gtg gga gca    432
Cys Asn Cys Ser Glu His Ile Pro Ser Thr Ile Ala Val Val Gly Ala
130                 135                 140 act ggc tca ggc gtc tcc acg gca gtg gca aat ctg ctg ggg ctc ttc    480
Thr Gly Ser Gly Val Ser Thr Ala Val Ala Asn Leu Leu Gly Leu Phe
145                 150                 155                 160 tac att ccc cag gtc agt tat gcc tcc tcc agc aga ctc ctc agc aac    528
Tyr Ile Pro Gln Val Ser Tyr Ala Ser Ser Ser Arg Leu Leu Ser Asn
                165                 170                 175 aag aat caa ttc aag tct ttc ctc cga acc atc ccc aat gat gag cac    576
Lys Asn Gln Phe Lys Ser Phe Leu Arg Thr Ile Pro Asn Asp Glu His
            180                 185                 190 cag gcc act gcc atg gca gac atc atc gag tat ttc cgc tgg aac tgg    624
Gln Ala Thr Ala Met Ala Asp Ile Ile Glu Tyr Phe Arg Trp Asn Trp
        195                 200                 205 gtg ggc aca att gca gct gat gac gac tat ggg cgg ccg ggg att gag    672
Val Gly Thr Ile Ala Ala Asp Asp Asp Tyr Gly Arg Pro Gly Ile Glu
210                 215                 220 aaa ttc cga gag gaa gct gag gaa agg gat atc tgc atc gac ttc agt    720
Lys Phe Arg Glu Glu Ala Glu Glu Arg Asp Ile Cys Ile Asp Phe Ser
225                 230                 235                 240 gaa ctc atc tcc cag tac tct gat gag gaa gag atc cag cat gtg gta    768
Glu Leu Ile Ser Gln Tyr Ser Asp Glu Glu Glu Ile Gln His Val Val
                245                 250                 255 gag gtg att caa aat tcc acg gcc aaa gtc atc gtg gtt ttc tcc agt    816
Glu Val Ile Gln Asn Ser Thr Ala Lys Val Ile Val Val Phe Ser Ser
            260                 265                 270 ggc cca gat ctt gag ccc ctc atc aag gag att gtc cgg cgc aat atc    864
Gly Pro Asp Leu Glu Pro Leu Ile Lys Glu Ile Val Arg Arg Asn Ile
        275                 280                 285 acg ggc aag atc tgg ctg gcc agc gag gcc tgg gcc agc tcc tcc ctg    912
Thr Gly Lys Ile Trp Leu Ala Ser Glu Ala Trp Ala Ser Ser Ser Leu
290                 295                 300 atc gcc atg cct cag tac ttc cac gtg gtt ggc ggc acc att gga ttc    960
Ile Ala Met Pro Gln Tyr Phe His Val Val Gly Gly Thr Ile Gly Phe
305                 310                 315                 320 gct ctg aag gct ggg cag atc cca ggc ttc cgg gaa ttc ctg aag aag    1008
Ala Leu Lys Ala Gly Gln Ile Pro Gly Phe Arg Glu Phe Leu Lys Lys
                325                 330                 335 gtc cat ccc agg aag tct gtc cac aat ggt ttt gcc aag gag ttt tgg    1056
Val His Pro Arg Lys Ser Val His Asn Gly Phe Ala Lys Glu Phe Trp
            340                 345                 350 gaa gaa aca ttt aac tgc cac ctc caa gaa ggt gca aaa gga cct tta    1104
Glu Glu Thr Phe Asn Cys His Leu Gln Glu Gly Ala Lys Gly Pro Leu
        355                 360                 365 cct gtg gac acc ttt ctg aga ggt cac gaa gaa agt ggc gac agg ttt    1152
Pro Val Asp Thr Phe Leu Arg Gly His Glu Glu Ser Gly Asp Arg Phe
370                 375                 380 agc aac agc tcg aca gcc ttc cga ccc ctc tgt aca ggg gat gag aac    1200
Ser Asn Ser Ser Thr Ala Phe Arg Pro Leu Cys Thr Gly Asp Glu Asn
385                 390                 395                 400 atc agc agt gtc gag acc cct tac ata gat tac acg cat tta cgg ata    1248
Ile Ser Ser Val Glu Thr Pro Tyr Ile Asp Tyr Thr His Leu Arg Ile
```

-continued

|  |  |  |  |  |  |  |  |  |  |  |  |  |  |  |  |  |
|---|---|---|---|---|---|---|---|---|---|---|---|---|---|---|---|---|
|  |  |  |  | 405 |  |  |  |  | 410 |  |  |  |  | 415 |  |  |

```
tcc tac aat gtg tac tta gca gtc tac tcc att gcc cac gcc ttg caa      1296
Ser Tyr Asn Val Tyr Leu Ala Val Tyr Ser Ile Ala His Ala Leu Gln
            420                 425                 430 gat ata tat acc tgc tta cct ggg aga ggg ctc ttc acc aat ggc tcc      1344
Asp Ile Tyr Thr Cys Leu Pro Gly Arg Gly Leu Phe Thr Asn Gly Ser
                435                 440                 445 tgt gca gac atc aag aaa gtt gag gcg tgg cag gtc ctg aag cac cta      1392
Cys Ala Asp Ile Lys Lys Val Glu Ala Trp Gln Val Leu Lys His Leu
    450                 455                 460 cgg cat cta aac ttt aca aac aat atg ggg gag cag gtg acc ttt gat      1440
Arg His Leu Asn Phe Thr Asn Asn Met Gly Glu Gln Val Thr Phe Asp
465                 470                 475                 480 gag tgt ggt gac ctg gtg ggg aac tat tcc atc atc aac tgg cac ctc      1488
Glu Cys Gly Asp Leu Val Gly Asn Tyr Ser Ile Ile Asn Trp His Leu
                485                 490                 495 tcc cca gag gat ggc tcc atc gtg ttt aag gaa gtc ggg tat tac aac      1536
Ser Pro Glu Asp Gly Ser Ile Val Phe Lys Glu Val Gly Tyr Tyr Asn
                500                 505                 510 gtc tat gcc aag aag gga gaa aga ctc ttc atc aac gag gag aaa atc      1584
Val Tyr Ala Lys Lys Gly Glu Arg Leu Phe Ile Asn Glu Glu Lys Ile
            515                 520                 525 ctg tgg agt ggg ttc tcc agg gag gtg ccc ttc tcc aac tgc agc cga      1632
Leu Trp Ser Gly Phe Ser Arg Glu Val Pro Phe Ser Asn Cys Ser Arg
530                 535                 540 gac tgc ctg gca ggg acc agg aaa ggg atc att gag ggg gag ccc acc      1680
Asp Cys Leu Ala Gly Thr Arg Lys Gly Ile Ile Glu Gly Glu Pro Thr
545                 550                 555                 560 tgc tgc ttt gag tgt gtg gag tgt cct gat ggg gag tat agt gat gag      1728
Cys Cys Phe Glu Cys Val Glu Cys Pro Asp Gly Glu Tyr Ser Asp Glu
                565                 570                 575 aca gat gcc agt gcc tgt aac aag tgc cca gat gac ttc tgg tcc aat      1776
Thr Asp Ala Ser Ala Cys Asn Lys Cys Pro Asp Asp Phe Trp Ser Asn
                580                 585                 590 gag aac cac acc tcc tgc att gcc aag gag atc gag ttt ctg tcg tgg      1824
Glu Asn His Thr Ser Cys Ile Ala Lys Glu Ile Glu Phe Leu Ser Trp
            595                 600                 605 acg gag ccc ttt ggg atc gca ctc acc ctc ttt gcc gtg ctg ggc att      1872
Thr Glu Pro Phe Gly Ile Ala Leu Thr Leu Phe Ala Val Leu Gly Ile
610                 615                 620 ttc ctg aca gcc ttt gtg ctg ggt gtg ttt atc aag ttc cgc aac aca      1920
Phe Leu Thr Ala Phe Val Leu Gly Val Phe Ile Lys Phe Arg Asn Thr
625                 630                 635                 640 ccc att gtc aag gcc acc aac cga gag ctc tcc tac ctc ctc ctc ttc      1968
Pro Ile Val Lys Ala Thr Asn Arg Glu Leu Ser Tyr Leu Leu Leu Phe
                645                 650                 655 tcc ctg ctc tgc tgc ttc tcc agc tcc ctg ttc ttc atc ggg gag ccc      2016
Ser Leu Leu Cys Cys Phe Ser Ser Ser Leu Phe Phe Ile Gly Glu Pro
            660                 665                 670 cag gac tgg acg tgc cgc ctc cgc cag ccg gcc ttt ggc atc agc ttc      2064
Gln Asp Trp Thr Cys Arg Leu Arg Gln Pro Ala Phe Gly Ile Ser Phe
                675                 680                 685 gtg ctc tgc atc tca tgc atc ctg gtg aaa acc aac cgt gtc ctc ctg      2112
Val Leu Cys Ile Ser Cys Ile Leu Val Lys Thr Asn Arg Val Leu Leu
            690                 695                 700 gtg ttt gag gcc aag atc ccc acc agc ttc cac cgc aag tgg tgg ggg      2160
Val Phe Glu Ala Lys Ile Pro Thr Ser Phe His Arg Lys Trp Trp Gly
705                 710                 715                 720 ctc aac ctg cag ttc ctg ctg gtt ttc ctc tgc acc ttc atg cag att      2208
Leu Asn Leu Gln Phe Leu Leu Val Phe Leu Cys Thr Phe Met Gln Ile
```

|  |  |  |  |  |  |  |  |  |  |  |  |  |  |
|---|---|---|---|---|---|---|---|---|---|---|---|---|---|
|  |  |  | 725 |  |  | 730 |  |  |  | 735 |  |  |  |
| gtc | atc | tgt | gtg | atc | tgg | ctc | tac | acc | gcg | ccc | ccc | tca | agc | tac | cgc | 2256 |
| Val | Ile | Cys | Val | Ile | Trp | Leu | Tyr | Thr | Ala | Pro | Pro | Ser | Ser | Tyr | Arg |  |
|  |  |  | 740 |  |  |  | 745 |  |  |  | 750 |  |  |  |

```
gtc atc tgt gtg atc tgg ctc tac acc gcg ccc ccc tca agc tac cgc    2256
Val Ile Cys Val Ile Trp Leu Tyr Thr Ala Pro Pro Ser Ser Tyr Arg
            740             745             750 aac cag gag ctg gag gat gag atc atc ttc atc acg tgc cac gag ggc    2304
Asn Gln Glu Leu Glu Asp Glu Ile Ile Phe Ile Thr Cys His Glu Gly
            755             760             765 tcc ctc atg gcc ctg ggc ttc ctg atc ggc tac acc tgc ctg ctg gct    2352
Ser Leu Met Ala Leu Gly Phe Leu Ile Gly Tyr Thr Cys Leu Leu Ala
            770             775             780 gcc atc tgc ttc ttc ttt gcc ttc aag tcc cgg aag ctg ccg gag aac    2400
Ala Ile Cys Phe Phe Phe Ala Phe Lys Ser Arg Lys Leu Pro Glu Asn
785             790             795             800 ttc aat gaa gcc aag ttc atc acc ttc agc atg ctc atc ttc ttc atc    2448
Phe Asn Glu Ala Lys Phe Ile Thr Phe Ser Met Leu Ile Phe Phe Ile
            805             810             815 gtc tgg atc tcc ttc att cca gcc tat gcc agc acc tat ggc aag ttt    2496
Val Trp Ile Ser Phe Ile Pro Ala Tyr Ala Ser Thr Tyr Gly Lys Phe
            820             825             830 gtc tct gcc gta gag gtg att gcc atc ctg gca gcc agc ttt ggc ttg    2544
Val Ser Ala Val Glu Val Ile Ala Ile Leu Ala Ala Ser Phe Gly Leu
            835             840             845 ctg gcg tgc atc ttc ttc aac aag atc tac atc att ctc ttc aag cca    2592
Leu Ala Cys Ile Phe Phe Asn Lys Ile Tyr Ile Ile Leu Phe Lys Pro
850             855             860 tcc cgc aac acc atc gag gag gtg cgt tgc agc acc gca gct cac gct    2640
Ser Arg Asn Thr Ile Glu Glu Val Arg Cys Ser Thr Ala Ala His Ala
865             870             875             880 ttc aag gtg gct gcc cgg gcc acg ctg cgc cgc agc aac gtc tcc cgc    2688
Phe Lys Val Ala Ala Arg Ala Thr Leu Arg Arg Ser Asn Val Ser Arg
            885             890             895 aag cgg tcc agc agc ctt gga ggc tcc acg gga tcc acc ccc tcc tcc    2736
Lys Arg Ser Ser Ser Leu Gly Gly Ser Thr Gly Ser Thr Pro Ser Ser
            900             905             910 tcc atc agc agc aag agc aac agc gaa gac cca ttc cca cag ccc gag    2784
Ser Ile Ser Ser Lys Ser Asn Ser Glu Asp Pro Phe Pro Gln Pro Glu
            915             920             925 agg cag aag cag cag cag ccg ctg gcc cta acc cag caa gag cag cag    2832
Arg Gln Lys Gln Gln Gln Pro Leu Ala Leu Thr Gln Gln Glu Gln Gln
            930             935             940 cag cag ccc ctg acc ctc cca cag cag caa cga tct cag cag cag ccc    2880
Gln Gln Pro Leu Thr Leu Pro Gln Gln Gln Arg Ser Gln Gln Gln Pro
945             950             955             960 aga tgc aag cag aag gtc atc ttt ggc agc ggc acg gtc acc ttc tca    2928
Arg Cys Lys Gln Lys Val Ile Phe Gly Ser Gly Thr Val Thr Phe Ser
            965             970             975 ctg agc ttt gat gag cct cag aag aac gcc atg gcc cac agg aat tct    2976
Leu Ser Phe Asp Glu Pro Gln Lys Asn Ala Met Ala His Arg Asn Ser
            980             985             990 acg cac cag aac tcc ctg gag gcc  cag aaa agc agc gat  acg ctg acc   3024
Thr His Gln Asn Ser Leu Glu Ala  Gln Lys Ser Ser Asp  Thr Leu Thr
            995             1000            1005 cga cac cag cca tta ctc ccg  ctg cag tgc ggg gaa  acg gac tta       3069
Arg His Gln Pro Leu Leu Pro  Leu Gln Cys Gly Glu  Thr Asp Leu
    1010            1015            1020 gat ctg acc gtc cag gaa aca  ggt ctg caa gga cct  gtg ggt gga       3114
Asp Leu Thr Val Gln Glu Thr  Gly Leu Gln Gly Pro  Val Gly Gly
    1025            1030            1035 gac cag cgg cca gag gtg gag  gac cct gaa gag ttg  tcc cca gca       3159
Asp Gln Arg Pro Glu Val Glu  Asp Pro Glu Glu Leu  Ser Pro Ala
```

```
              1040                1045                1050
ctt gta gtg tcc agt tca cag agc ttt gtc atc agt ggt gga ggc        3204
Leu Val Val Ser Ser Ser Gln Ser Phe Val Ile Ser Gly Gly Gly
        1055                1060                1065 agc act gtt aca gaa aac gta gtg aat tca taa                        3237
Ser Thr Val Thr Glu Asn Val Val Asn Ser
        1070                1075
```

<210> SEQ ID NO 12
<211> LENGTH: 1078
<212> TYPE: PRT
<213> ORGANISM: human

<400> SEQUENCE: 12

```
Met Ala Phe Tyr Ser Cys Cys Trp Val Leu Leu Ala Leu Thr Trp His
1               5                   10                  15

Thr Ser Ala Tyr Gly Pro Asp Gln Arg Ala Gln Lys Lys Gly Asp Ile
            20                  25                  30

Ile Leu Gly Gly Leu Phe Pro Ile His Phe Gly Val Ala Ala Lys Asp
        35                  40                  45

Gln Asp Leu Lys Ser Arg Pro Glu Ser Val Glu Cys Ile Arg Tyr Asn
    50                  55                  60

Phe Arg Gly Phe Arg Trp Leu Gln Ala Met Ile Phe Ala Ile Glu Glu
65                  70                  75                  80

Ile Asn Ser Ser Pro Ala Leu Leu Pro Asn Leu Thr Leu Gly Tyr Arg
                85                  90                  95

Ile Phe Asp Thr Cys Asn Thr Val Ser Lys Ala Leu Glu Ala Thr Leu
            100                 105                 110

Ser Phe Val Ala Gln Asn Lys Ile Asp Ser Leu Asn Leu Asp Glu Phe
        115                 120                 125

Cys Asn Cys Ser Glu His Ile Pro Ser Thr Ile Ala Val Val Gly Ala
    130                 135                 140

Thr Gly Ser Gly Val Ser Thr Ala Val Ala Asn Leu Leu Gly Leu Phe
145                 150                 155                 160

Tyr Ile Pro Gln Val Ser Tyr Ala Ser Ser Ser Arg Leu Leu Ser Asn
                165                 170                 175

Lys Asn Gln Phe Lys Ser Phe Leu Arg Thr Ile Pro Asn Asp Glu His
            180                 185                 190

Gln Ala Thr Ala Met Ala Asp Ile Ile Glu Tyr Phe Arg Trp Asn Trp
        195                 200                 205

Val Gly Thr Ile Ala Ala Asp Asp Asp Tyr Gly Arg Pro Gly Ile Glu
    210                 215                 220

Lys Phe Arg Glu Glu Ala Glu Glu Arg Asp Ile Cys Ile Asp Phe Ser
225                 230                 235                 240

Glu Leu Ile Ser Gln Tyr Ser Asp Glu Glu Ile Gln His Val Val
                245                 250                 255

Glu Val Ile Gln Asn Ser Thr Ala Lys Val Ile Val Val Phe Ser Ser
            260                 265                 270

Gly Pro Asp Leu Glu Pro Leu Ile Lys Glu Ile Val Arg Arg Asn Ile
        275                 280                 285

Thr Gly Lys Ile Trp Leu Ala Ser Glu Ala Trp Ala Ser Ser Ser Leu
    290                 295                 300

Ile Ala Met Pro Gln Tyr Phe His Val Val Gly Gly Thr Ile Gly Phe
305                 310                 315                 320

Ala Leu Lys Ala Gly Gln Ile Pro Gly Phe Arg Glu Phe Leu Lys Lys
                325                 330                 335
```

-continued

```
Val His Pro Arg Lys Ser Val His Asn Gly Phe Ala Lys Glu Phe Trp
            340                 345                 350
Glu Glu Thr Phe Asn Cys His Leu Gln Glu Gly Ala Lys Gly Pro Leu
        355                 360                 365
Pro Val Asp Thr Phe Leu Arg Gly His Glu Glu Ser Gly Asp Arg Phe
370                 375                 380
Ser Asn Ser Ser Thr Ala Phe Arg Pro Leu Cys Thr Gly Asp Glu Asn
385                 390                 395                 400
Ile Ser Ser Val Glu Thr Pro Tyr Ile Asp Tyr Thr His Leu Arg Ile
                405                 410                 415
Ser Tyr Asn Val Tyr Leu Ala Val Tyr Ser Ile Ala His Ala Leu Gln
            420                 425                 430
Asp Ile Tyr Thr Cys Leu Pro Gly Arg Gly Leu Phe Thr Asn Gly Ser
        435                 440                 445
Cys Ala Asp Ile Lys Lys Val Glu Ala Trp Gln Val Leu Lys His Leu
450                 455                 460
Arg His Leu Asn Phe Thr Asn Asn Met Gly Glu Gln Val Thr Phe Asp
465                 470                 475                 480
Glu Cys Gly Asp Leu Val Gly Asn Tyr Ser Ile Ile Asn Trp His Leu
                485                 490                 495
Ser Pro Glu Asp Gly Ser Ile Val Phe Lys Glu Val Gly Tyr Tyr Asn
            500                 505                 510
Val Tyr Ala Lys Lys Gly Glu Arg Leu Phe Ile Asn Glu Glu Lys Ile
        515                 520                 525
Leu Trp Ser Gly Phe Ser Arg Glu Val Pro Phe Ser Asn Cys Ser Arg
530                 535                 540
Asp Cys Leu Ala Gly Thr Arg Lys Gly Ile Ile Glu Gly Glu Pro Thr
545                 550                 555                 560
Cys Cys Phe Glu Cys Val Glu Cys Pro Asp Gly Glu Tyr Ser Asp Glu
                565                 570                 575
Thr Asp Ala Ser Ala Cys Asn Lys Cys Pro Asp Asp Phe Trp Ser Asn
            580                 585                 590
Glu Asn His Thr Ser Cys Ile Ala Lys Glu Ile Glu Phe Leu Ser Trp
        595                 600                 605
Thr Glu Pro Phe Gly Ile Ala Leu Thr Leu Phe Ala Val Leu Gly Ile
610                 615                 620
Phe Leu Thr Ala Phe Val Leu Gly Val Phe Ile Lys Phe Arg Asn Thr
625                 630                 635                 640
Pro Ile Val Lys Ala Thr Asn Arg Glu Leu Ser Tyr Leu Leu Leu Phe
                645                 650                 655
Ser Leu Leu Cys Cys Phe Ser Ser Ser Leu Phe Phe Ile Gly Glu Pro
            660                 665                 670
Gln Asp Trp Thr Cys Arg Leu Arg Gln Pro Ala Phe Gly Ile Ser Phe
        675                 680                 685
Val Leu Cys Ile Ser Cys Ile Leu Val Lys Thr Asn Arg Val Leu Leu
690                 695                 700
Val Phe Glu Ala Lys Ile Pro Thr Ser Phe His Arg Lys Trp Trp Gly
705                 710                 715                 720
Leu Asn Leu Gln Phe Leu Leu Val Phe Leu Cys Thr Phe Met Gln Ile
                725                 730                 735
Val Ile Cys Val Ile Trp Leu Tyr Thr Ala Pro Pro Ser Ser Tyr Arg
            740                 745                 750
Asn Gln Glu Leu Glu Asp Glu Ile Ile Phe Ile Thr Cys His Glu Gly
```

```
                755                 760                 765
Ser Leu Met Ala Leu Gly Phe Leu Ile Gly Tyr Thr Cys Leu Leu Ala
    770                 775                 780

Ala Ile Cys Phe Phe Phe Ala Phe Lys Ser Arg Lys Leu Pro Glu Asn
785                 790                 795                 800

Phe Asn Glu Ala Lys Phe Ile Thr Phe Ser Met Leu Ile Phe Phe Ile
                805                 810                 815

Val Trp Ile Ser Phe Ile Pro Ala Tyr Ala Ser Thr Tyr Gly Lys Phe
            820                 825                 830

Val Ser Ala Val Glu Val Ile Ala Ile Leu Ala Ala Ser Phe Gly Leu
            835                 840                 845

Leu Ala Cys Ile Phe Phe Asn Lys Ile Tyr Ile Ile Leu Phe Lys Pro
        850                 855                 860

Ser Arg Asn Thr Ile Glu Glu Val Arg Cys Ser Thr Ala Ala His Ala
865                 870                 875                 880

Phe Lys Val Ala Ala Arg Ala Thr Leu Arg Arg Ser Asn Val Ser Arg
                885                 890                 895

Lys Arg Ser Ser Ser Leu Gly Gly Ser Thr Gly Ser Thr Pro Ser Ser
            900                 905                 910

Ser Ile Ser Ser Lys Ser Asn Ser Glu Asp Pro Phe Pro Gln Pro Glu
        915                 920                 925

Arg Gln Lys Gln Gln Pro Leu Ala Leu Thr Gln Glu Gln Gln
            930                 935                 940

Gln Gln Pro Leu Thr Leu Pro Gln Gln Arg Ser Gln Gln Pro
945                 950                 955                 960

Arg Cys Lys Gln Lys Val Ile Phe Gly Ser Gly Thr Val Thr Phe Ser
                965                 970                 975

Leu Ser Phe Asp Glu Pro Gln Lys Asn Ala Met Ala His Arg Asn Ser
            980                 985                 990

Thr His Gln Asn Ser Leu Glu Ala  Gln Lys Ser Ser Asp  Thr Leu Thr
        995                 1000                1005

Arg His  Gln Pro Leu Leu Pro  Leu Gln Cys Gly Glu  Thr Asp Leu
    1010                1015                1020

Asp Leu  Thr Val Gln Glu Thr  Gly Leu Gln Gly Pro  Val Gly Gly
    1025                1030                1035

Asp Gln  Arg Pro Glu Val Glu  Asp Pro Glu Glu Leu  Ser Pro Ala
    1040                1045                1050

Leu Val  Val Ser Ser Ser Gln  Ser Phe Val Ile Ser  Gly Gly Gly
    1055                1060                1065

Ser Thr  Val Thr Glu Asn Val  Val Asn Ser
    1070                1075

<210> SEQ ID NO 13
<211> LENGTH: 28
<212> TYPE: DNA
<213> ORGANISM: artificial
<220> FEATURE:
<223> OTHER INFORMATION: primer

<400> SEQUENCE: 13
caccaagctt atggcatttt atagctgc                                      28

<210> SEQ ID NO 14
<211> LENGTH: 28
<212> TYPE: DNA
<213> ORGANISM: artificial
<220> FEATURE:
```

```
<223> OTHER INFORMATION: primer

<400> SEQUENCE: 14
atatccgcgg cacctccctg gagaaccc                                              28

<210> SEQ ID NO 15
<211> LENGTH: 28
<212> TYPE: DNA
<213> ORGANISM: artificial
<220> FEATURE:
<223> OTHER INFORMATION: primer

<400> SEQUENCE: 15
atatccgcgg tccatgtgtt ccaagagg                                              28

<210> SEQ ID NO 16
<211> LENGTH: 28
<212> TYPE: DNA
<213> ORGANISM: artificial
<220> FEATURE:
<223> OTHER INFORMATION: primer

<400> SEQUENCE: 16
atatgcggcc gcagtccctc ctcatggt                                              28

<210> SEQ ID NO 17
<211> LENGTH: 28
<212> TYPE: DNA
<213> ORGANISM: artificial
<220> FEATURE:
<223> OTHER INFORMATION: primer

<400> SEQUENCE: 17
atatccgcgg tcccggtgct cgcggcag                                              28

<210> SEQ ID NO 18
<211> LENGTH: 31
<212> TYPE: DNA
<213> ORGANISM: artificial
<220> FEATURE:
<223> OTHER INFORMATION: primer

<400> SEQUENCE: 18
atatgcggcc gcactcatgt ttcccctgat t                                          31

<210> SEQ ID NO 19
<211> LENGTH: 2658
<212> TYPE: DNA
<213> ORGANISM: artificial
<220> FEATURE:
<223> OTHER INFORMATION: fusion product of human DNA sequence fragments
<220> FEATURE:
<221> NAME/KEY: CDS
<222> LOCATION: (1)..(2658)

<400> SEQUENCE: 19 atg gca ttt tat agc tgc tgc tgg gtc ctc ttg gca ctc acc tgg cac            48
Met Ala Phe Tyr Ser Cys Cys Trp Val Leu Leu Ala Leu Thr Trp His
1               5                   10                  15 acc tct gcc tac ggg cca gac cag cga gcc caa aag aag ggg gac att            96
Thr Ser Ala Tyr Gly Pro Asp Gln Arg Ala Gln Lys Lys Gly Asp Ile
                20                  25                  30 atc ctt ggg ggg ctc ttt cct att cat ttt gga gta gca gct aaa gat           144
Ile Leu Gly Gly Leu Phe Pro Ile His Phe Gly Val Ala Ala Lys Asp
            35                  40                  45 caa gat ctc aaa tca agg ccg gag tct gtg gaa tgt atc agg tat aat           192
```

| | | | | | | | | | | | | | | |
|---|---|---|---|---|---|---|---|---|---|---|---|---|---|---|
| Gln | Asp | Leu | Lys | Ser | Arg | Pro | Glu | Ser | Val | Glu | Cys | Ile | Arg | Tyr | Asn |
| | 50 | | | | 55 | | | | 60 | | | | | |

```
ttc cgt ggg ttt cgc tgg tta cag gct atg ata ttt gcc ata gag gag      240
Phe Arg Gly Phe Arg Trp Leu Gln Ala Met Ile Phe Ala Ile Glu Glu
 65              70                  75                  80 ata aac agc agc cca gcc ctt ctt ccc aac ttg acg ctg gga tac agg      288
Ile Asn Ser Ser Pro Ala Leu Leu Pro Asn Leu Thr Leu Gly Tyr Arg
                 85                  90                  95 ata ttt gac act tgc aac acc gtt tct aag gcc ttg gaa gcc acc ctg      336
Ile Phe Asp Thr Cys Asn Thr Val Ser Lys Ala Leu Glu Ala Thr Leu
                100                 105                 110 agt ttt gtt gct caa aac aaa att gat tct ttg aac ctt gat gag ttc      384
Ser Phe Val Ala Gln Asn Lys Ile Asp Ser Leu Asn Leu Asp Glu Phe
            115                 120                 125 tgc aac tgc tca gag cac att ccc tct acg att gct gtg gtg gga gca      432
Cys Asn Cys Ser Glu His Ile Pro Ser Thr Ile Ala Val Val Gly Ala
        130                 135                 140 act ggc tca ggc gtc tcc acg gca gtg gca aat ctg ctg ggg ctc ttc      480
Thr Gly Ser Gly Val Ser Thr Ala Val Ala Asn Leu Leu Gly Leu Phe
145                 150                 155                 160 tac att ccc cag gtc agt tat gcc tcc tcc agc aga ctc ctc agc aac      528
Tyr Ile Pro Gln Val Ser Tyr Ala Ser Ser Ser Arg Leu Leu Ser Asn
                165                 170                 175 aag aat caa ttc aag tct ttc ctc cga acc atc ccc aat gat gag cac      576
Lys Asn Gln Phe Lys Ser Phe Leu Arg Thr Ile Pro Asn Asp Glu His
                180                 185                 190 cag gcc act gcc atg gca gac atc atc gag tat ttc cgc tgg aac tgg      624
Gln Ala Thr Ala Met Ala Asp Ile Ile Glu Tyr Phe Arg Trp Asn Trp
            195                 200                 205 gtg ggc aca att gca gct gat gac gac tat ggg cgg ccg ggg att gag      672
Val Gly Thr Ile Ala Ala Asp Asp Asp Tyr Gly Arg Pro Gly Ile Glu
        210                 215                 220 aaa ttc cga gag gaa gct gag gaa agg gat atc tgc atc gac ttc agt      720
Lys Phe Arg Glu Glu Ala Glu Glu Arg Asp Ile Cys Ile Asp Phe Ser
225                 230                 235                 240 gaa ctc atc tcc cag tac tct gat gag gaa gag atc cag cat gtg gta      768
Glu Leu Ile Ser Gln Tyr Ser Asp Glu Glu Glu Ile Gln His Val Val
                245                 250                 255 gag gtg att caa aat tcc acg gcc aaa gtc atc gtg gtt ttc tcc agt      816
Glu Val Ile Gln Asn Ser Thr Ala Lys Val Ile Val Val Phe Ser Ser
                260                 265                 270 ggc cca gat ctt gag ccc ctc atc aag gag att gtc cgg cgc aat atc      864
Gly Pro Asp Leu Glu Pro Leu Ile Lys Glu Ile Val Arg Arg Asn Ile
            275                 280                 285 acg ggc aag atc tgg ctg gcc agc gag gcc tgg gcc agc tcc tcc ctg      912
Thr Gly Lys Ile Trp Leu Ala Ser Glu Ala Trp Ala Ser Ser Ser Leu
        290                 295                 300 atc gcc atg cct cag tac ttc cac gtg gtt ggc ggc acc att gga ttc      960
Ile Ala Met Pro Gln Tyr Phe His Val Val Gly Gly Thr Ile Gly Phe
305                 310                 315                 320 gct ctg aag gct ggg cag atc cca ggc ttc cgg gaa ttc ctg aag aag     1008
Ala Leu Lys Ala Gly Gln Ile Pro Gly Phe Arg Glu Phe Leu Lys Lys
                325                 330                 335 gtc cat ccc agg aag tct gtc cac aat ggt ttt gcc aag gag ttt tgg     1056
Val His Pro Arg Lys Ser Val His Asn Gly Phe Ala Lys Glu Phe Trp
                340                 345                 350 gaa gaa aca ttt aac tgc cac ctc caa gaa ggt gca aaa gga cct tta     1104
Glu Glu Thr Phe Asn Cys His Leu Gln Glu Gly Ala Lys Gly Pro Leu
            355                 360                 365 cct gtg gac acc ttt ctg aga ggt cac gaa gaa agt ggc gac agg ttt     1152
```

-continued

| | | |
|---|---|---|
| Pro Val Asp Thr Phe Leu Arg Gly His Glu Glu Ser Gly Asp Arg Phe<br>370                              375                      380 | | |
| agc aac agc tcg aca gcc ttc cga ccc ctc tgt aca ggg gat gag aac<br>Ser Asn Ser Ser Thr Ala Phe Arg Pro Leu Cys Thr Gly Asp Glu Asn<br>385                              390                      395                      400 | 1200 | |
| atc agc agt gtc gag acc cct tac ata gat tac acg cat tta cgg ata<br>Ile Ser Ser Val Glu Thr Pro Tyr Ile Asp Tyr Thr His Leu Arg Ile<br>                             405                      410                      415 | 1248 | |
| tcc tac aat gtg tac tta gca gtc tac tcc att gcc cac gcc ttg caa<br>Ser Tyr Asn Val Tyr Leu Ala Val Tyr Ser Ile Ala His Ala Leu Gln<br>                    420                      425                      430 | 1296 | |
| gat ata tat acc tgc tta cct ggg aga ggg ctc ttc acc aat ggc tcc<br>Asp Ile Tyr Thr Cys Leu Pro Gly Arg Gly Leu Phe Thr Asn Gly Ser<br>                435                      440                      445 | 1344 | |
| tgt gca gac atc aag aaa gtt gag gcg tgg cag gtc ctg aag cac cta<br>Cys Ala Asp Ile Lys Lys Val Glu Ala Trp Gln Val Leu Lys His Leu<br>450                              455                      460 | 1392 | |
| cgg cat cta aac ttt aca aac aat atg ggg gag cag gtg acc ttt gat<br>Arg His Leu Asn Phe Thr Asn Asn Met Gly Glu Gln Val Thr Phe Asp<br>465                              470                      475                      480 | 1440 | |
| gag tgt ggt gac ctg gtg ggg aac tat tcc atc atc aac tgg cac ctc<br>Glu Cys Gly Asp Leu Val Gly Asn Tyr Ser Ile Ile Asn Trp His Leu<br>                    485                      490                      495 | 1488 | |
| tcc cca gag gat ggc tcc atc gtg ttt aag gaa gtc ggg tat tac aac<br>Ser Pro Glu Asp Gly Ser Ile Val Phe Lys Glu Val Gly Tyr Tyr Asn<br>                500                      505                      510 | 1536 | |
| gtc tat gcc aag aag gga gaa aga ctc ttc atc aac gag gag aaa atc<br>Val Tyr Ala Lys Lys Gly Glu Arg Leu Phe Ile Asn Glu Glu Lys Ile<br>              515                      520                      525 | 1584 | |
| ctg tgg agt ggg ttc tcc agg gag gtg ccc ttc tcc aac tgc agc cga<br>Leu Trp Ser Gly Phe Ser Arg Glu Val Pro Phe Ser Asn Cys Ser Arg<br>530                              535                      540 | 1632 | |
| gac tgc ctg gca ggg acc agg aaa ggg atc att gag ggg gag ccc acc<br>Asp Cys Leu Ala Gly Thr Arg Lys Gly Ile Ile Glu Gly Glu Pro Thr<br>545                              550                      555                      560 | 1680 | |
| tgc tgc ttt gag tgt gtg gag tgt cct gat ggg gag tat agt gat gag<br>Cys Cys Phe Glu Cys Val Glu Cys Pro Asp Gly Glu Tyr Ser Asp Glu<br>                      565                      570                      575 | 1728 | |
| aca gat gcc agt gcc tgt aac aag tgc cca gat gac ttc tgg tcc aat<br>Thr Asp Ala Ser Ala Cys Asn Lys Cys Pro Asp Asp Phe Trp Ser Asn<br>                580                      585                      590 | 1776 | |
| gag aac cac acc tcc tgc att gcc aag cgt acg gtc ttc ctg gaa tgg<br>Glu Asn His Thr Ser Cys Ile Ala Lys Arg Thr Val Phe Leu Glu Trp<br>              595                      600                      605 | 1824 | |
| cat gag gca ccc acc atc gct gtg gcc ctg ctg gcc gcc ctg ggc ttc<br>His Glu Ala Pro Thr Ile Ala Val Ala Leu Leu Ala Ala Leu Gly Phe<br>610                              615                      620 | 1872 | |
| ctc agc acc ctg gcc atc ctg gtg ata ttc tgg agg cac ttc cag aca<br>Leu Ser Thr Leu Ala Ile Leu Val Ile Phe Trp Arg His Phe Gln Thr<br>625                              630                      635                      640 | 1920 | |
| ccc ata gtt cgc tcg gct ggg ggc ccc atg tgc ttc ctg atg ctg aca<br>Pro Ile Val Arg Ser Ala Gly Gly Pro Met Cys Phe Leu Met Leu Thr<br>                    645                      650                      655 | 1968 | |
| ctg ctg ctg gtg gca tac atg gtg gtc ccg gtg tac gtg ggg ccg ccc<br>Leu Leu Leu Val Ala Tyr Met Val Val Pro Val Tyr Val Gly Pro Pro<br>                660                      665                      670 | 2016 | |
| aag gtc tcc acc tgc ctc tgc cgc cag gcc ctc ttt ccc ctc tgc ttc<br>Lys Val Ser Thr Cys Leu Cys Arg Gln Ala Leu Phe Pro Leu Cys Phe<br>              675                      680                      685 | 2064 | |
| aca att tgc atc tcc tgt atc gcc gtg cgt tct ttc cag atc gtc tgc<br> | 2112 | |

```
                                    -continued

Thr Ile Cys Ile Ser Cys Ile Ala Val Arg Ser Phe Gln Ile Val Cys
        690                 695                 700 gcc ttc aag atg gcc agc cgc ttc cca cgc gcc tac agc tac tgg gtc       2160
Ala Phe Lys Met Ala Ser Arg Phe Pro Arg Ala Tyr Ser Tyr Trp Val
705                 710                 715                 720 cgc tac cag ggg ccc tac gtc tct atg gca ttt atc acg gta ctc aaa       2208
Arg Tyr Gln Gly Pro Tyr Val Ser Met Ala Phe Ile Thr Val Leu Lys
                725                 730                 735 atg gtc att gtg gta att ggc atg ctg gcc acg ggc ctc agt ccc acc       2256
Met Val Ile Val Val Ile Gly Met Leu Ala Thr Gly Leu Ser Pro Thr
        740                 745                 750 acc cgt act gac ccc gat gac ccc aag atc aca att gtc tcc tgt aac       2304
Thr Arg Thr Asp Pro Asp Asp Pro Lys Ile Thr Ile Val Ser Cys Asn
755                 760                 765 ccc aac tac cgc aac agc ctg ctg ttc aac acc agc ctg gac ctg ctg       2352
Pro Asn Tyr Arg Asn Ser Leu Leu Phe Asn Thr Ser Leu Asp Leu Leu
        770                 775                 780 ctc tca gtg gtg ggt ttc agc ttc gcc tac atg ggc aaa gag ctg ccc       2400
Leu Ser Val Val Gly Phe Ser Phe Ala Tyr Met Gly Lys Glu Leu Pro
785                 790                 795                 800 acc aac tac aac gag gcc aag ttc atc acc ctc agc atg acc ttc tat       2448
Thr Asn Tyr Asn Glu Ala Lys Phe Ile Thr Leu Ser Met Thr Phe Tyr
            805                 810                 815 ttc acc tca tcc gtc tcc ctc tgc acc ttc atg tct gcc tac agc ggg       2496
Phe Thr Ser Ser Val Ser Leu Cys Thr Phe Met Ser Ala Tyr Ser Gly
        820                 825                 830 gtg ctg gtc acc atc gtg gac ctc ttg gtc act gtg ctc aac ctc ctg       2544
Val Leu Val Thr Ile Val Asp Leu Leu Val Thr Val Leu Asn Leu Leu
835                 840                 845 gcc atc agc ctg ggc tac ttc ggc ccc aag tgc tac atg atc ctc ttc       2592
Ala Ile Ser Leu Gly Tyr Phe Gly Pro Lys Cys Tyr Met Ile Leu Phe
850                 855                 860 tac ccg gag cgc aac acg ccc gcc tac ttc aac agc atg atc cag ggc       2640
Tyr Pro Glu Arg Asn Thr Pro Ala Tyr Phe Asn Ser Met Ile Gln Gly
865                 870                 875                 880 tac acc atg agg agg gac                                                2658
Tyr Thr Met Arg Arg Asp
            885

<210> SEQ ID NO 20
<211> LENGTH: 886
<212> TYPE: PRT
<213> ORGANISM: artificial
<220> FEATURE:
<223> OTHER INFORMATION: Synthetic Construct

<400> SEQUENCE: 20

Met Ala Phe Tyr Ser Cys Cys Trp Val Leu Leu Ala Leu Thr Trp His
1               5                   10                  15

Thr Ser Ala Tyr Gly Pro Asp Gln Arg Ala Gln Lys Lys Gly Asp Ile
            20                  25                  30

Ile Leu Gly Gly Leu Phe Pro Ile His Phe Gly Val Ala Ala Lys Asp
        35                  40                  45

Gln Asp Leu Lys Ser Arg Pro Glu Ser Val Glu Cys Ile Arg Tyr Asn
    50                  55                  60

Phe Arg Gly Phe Arg Trp Leu Gln Ala Met Ile Phe Ala Ile Glu Glu
65                  70                  75                  80

Ile Asn Ser Ser Pro Ala Leu Leu Pro Asn Leu Thr Leu Gly Tyr Arg
                85                  90                  95

Ile Phe Asp Thr Cys Asn Thr Val Ser Lys Ala Leu Glu Ala Thr Leu
```

-continued

```
                100                 105                 110
        Ser Phe Val Ala Gln Asn Lys Ile Asp Ser Leu Asn Leu Asp Glu Phe
                        115                 120                 125

Cys Asn Cys Ser Glu His Ile Pro Ser Thr Ile Ala Val Val Gly Ala
                        130                 135                 140

Thr Gly Ser Gly Val Ser Thr Ala Val Ala Asn Leu Leu Gly Leu Phe
        145                 150                 155                 160

Tyr Ile Pro Gln Val Ser Tyr Ala Ser Ser Arg Leu Leu Ser Asn
                        165                 170                 175

Lys Asn Gln Phe Lys Ser Phe Leu Arg Thr Ile Pro Asn Asp Glu His
                        180                 185                 190

Gln Ala Thr Ala Met Ala Asp Ile Ile Glu Tyr Phe Arg Trp Asn Trp
                        195                 200                 205

Val Gly Thr Ile Ala Ala Asp Asp Tyr Gly Arg Pro Gly Ile Glu
                        210                 215                 220

Lys Phe Arg Glu Glu Ala Glu Arg Asp Ile Cys Ile Asp Phe Ser
        225                 230                 235                 240

Glu Leu Ile Ser Gln Tyr Ser Asp Glu Glu Ile Gln His Val Val
                        245                 250                 255

Glu Val Ile Gln Asn Ser Thr Ala Lys Val Ile Val Phe Ser Ser
                        260                 265                 270

Gly Pro Asp Leu Glu Pro Leu Ile Lys Glu Ile Val Arg Arg Asn Ile
                        275                 280                 285

Thr Gly Lys Ile Trp Leu Ala Ser Glu Ala Trp Ala Ser Ser Ser Leu
                        290                 295                 300

Ile Ala Met Pro Gln Tyr Phe His Val Val Gly Gly Thr Ile Gly Phe
        305                 310                 315                 320

Ala Leu Lys Ala Gly Gln Ile Pro Gly Phe Arg Glu Phe Leu Lys Lys
                        325                 330                 335

Val His Pro Arg Lys Ser Val His Asn Gly Phe Ala Lys Glu Phe Trp
                        340                 345                 350

Glu Glu Thr Phe Asn Cys His Leu Gln Glu Gly Ala Lys Gly Pro Leu
                        355                 360                 365

Pro Val Asp Thr Phe Leu Arg Gly His Glu Glu Ser Gly Asp Arg Phe
                        370                 375                 380

Ser Asn Ser Ser Thr Ala Phe Arg Pro Leu Cys Thr Gly Asp Glu Asn
        385                 390                 395                 400

Ile Ser Ser Val Glu Thr Pro Tyr Ile Asp Tyr Thr His Leu Arg Ile
                        405                 410                 415

Ser Tyr Asn Val Tyr Leu Ala Val Tyr Ser Ile Ala His Ala Leu Gln
                        420                 425                 430

Asp Ile Tyr Thr Cys Leu Pro Gly Arg Gly Leu Phe Thr Asn Gly Ser
                        435                 440                 445

Cys Ala Asp Ile Lys Lys Val Glu Ala Trp Gln Val Leu Lys His Leu
                        450                 455                 460

Arg His Leu Asn Phe Thr Asn Asn Met Gly Glu Gln Val Thr Phe Asp
        465                 470                 475                 480

Glu Cys Gly Asp Leu Val Gly Asn Tyr Ser Ile Ile Asn Trp His Leu
                        485                 490                 495

Ser Pro Glu Asp Gly Ser Ile Val Phe Lys Glu Val Gly Tyr Tyr Asn
                        500                 505                 510

Val Tyr Ala Lys Lys Gly Glu Arg Leu Phe Ile Asn Glu Glu Lys Ile
                        515                 520                 525
```

```
Leu Trp Ser Gly Phe Ser Arg Glu Val Pro Phe Ser Asn Cys Ser Arg
            530                 535                 540

Asp Cys Leu Ala Gly Thr Arg Lys Gly Ile Ile Glu Gly Glu Pro Thr
545                 550                 555                 560

Cys Cys Phe Glu Cys Val Glu Cys Pro Asp Gly Glu Tyr Ser Asp Glu
                565                 570                 575

Thr Asp Ala Ser Ala Cys Asn Lys Cys Pro Asp Asp Phe Trp Ser Asn
                580                 585                 590

Glu Asn His Thr Ser Cys Ile Ala Lys Arg Thr Val Phe Leu Glu Trp
            595                 600                 605

His Glu Ala Pro Thr Ile Ala Val Ala Leu Leu Ala Ala Leu Gly Phe
610                 615                 620

Leu Ser Thr Leu Ala Ile Leu Val Ile Phe Trp Arg His Phe Gln Thr
625                 630                 635                 640

Pro Ile Val Arg Ser Ala Gly Gly Pro Met Cys Phe Leu Met Leu Thr
                645                 650                 655

Leu Leu Leu Val Ala Tyr Met Val Val Pro Val Tyr Val Gly Pro Pro
                660                 665                 670

Lys Val Ser Thr Cys Leu Cys Arg Gln Ala Leu Phe Pro Leu Cys Phe
                675                 680                 685

Thr Ile Cys Ile Ser Cys Ile Ala Val Arg Ser Phe Gln Ile Val Cys
690                 695                 700

Ala Phe Lys Met Ala Ser Arg Phe Pro Arg Ala Tyr Ser Tyr Trp Val
705                 710                 715                 720

Arg Tyr Gln Gly Pro Tyr Val Ser Met Ala Phe Ile Thr Val Leu Lys
                725                 730                 735

Met Val Ile Val Val Ile Gly Met Leu Ala Thr Gly Leu Ser Pro Thr
                740                 745                 750

Thr Arg Thr Asp Pro Asp Asp Pro Lys Ile Thr Ile Val Ser Cys Asn
                755                 760                 765

Pro Asn Tyr Arg Asn Ser Leu Leu Phe Asn Thr Ser Leu Asp Leu Leu
                770                 775                 780

Leu Ser Val Val Gly Phe Ser Phe Ala Tyr Met Gly Lys Glu Leu Pro
785                 790                 795                 800

Thr Asn Tyr Asn Glu Ala Lys Phe Ile Thr Leu Ser Met Thr Phe Tyr
                805                 810                 815

Phe Thr Ser Ser Val Ser Leu Cys Thr Phe Met Ser Ala Tyr Ser Gly
                820                 825                 830

Val Leu Val Thr Ile Val Asp Leu Leu Val Thr Val Leu Asn Leu Leu
                835                 840                 845

Ala Ile Ser Leu Gly Tyr Phe Gly Pro Lys Cys Tyr Met Ile Leu Phe
850                 855                 860

Tyr Pro Glu Arg Asn Thr Pro Ala Tyr Phe Asn Ser Met Ile Gln Gly
865                 870                 875                 880

Tyr Thr Met Arg Arg Asp
                885

<210> SEQ ID NO 21
<211> LENGTH: 2691
<212> TYPE: DNA
<213> ORGANISM: artificial
<220> FEATURE:
<223> OTHER INFORMATION: fusion product of human DNA sequence fragments
<220> FEATURE:
<221> NAME/KEY: CDS
<222> LOCATION: (1)..(2691)
```

<400> SEQUENCE: 21

```
atg gca ttt tat agc tgc tgc tgg gtc ctc ttg gca ctc acc tgg cac        48
Met Ala Phe Tyr Ser Cys Cys Trp Val Leu Leu Ala Leu Thr Trp His
1               5                   10                  15 acc tct gcc tac ggg cca gac cag cga gcc caa aag aag ggg gac att        96
Thr Ser Ala Tyr Gly Pro Asp Gln Arg Ala Gln Lys Lys Gly Asp Ile
            20                  25                  30 atc ctt ggg ggg ctc ttt cct att cat ttt gga gta gca gct aaa gat       144
Ile Leu Gly Gly Leu Phe Pro Ile His Phe Gly Val Ala Ala Lys Asp
        35                  40                  45 caa gat ctc aaa tca agg ccg gag tct gtg gaa tgt atc agg tat aat       192
Gln Asp Leu Lys Ser Arg Pro Glu Ser Val Glu Cys Ile Arg Tyr Asn
    50                  55                  60 ttc cgt ggg ttt cgc tgg tta cag gct atg ata ttt gcc ata gag gag       240
Phe Arg Gly Phe Arg Trp Leu Gln Ala Met Ile Phe Ala Ile Glu Glu
65                  70                  75                  80 ata aac agc agc cca gcc ctt ctt ccc aac ttg acg ctg gga tac agg       288
Ile Asn Ser Ser Pro Ala Leu Leu Pro Asn Leu Thr Leu Gly Tyr Arg
                85                  90                  95 ata ttt gac act tgc aac acc gtt tct aag gcc ttg gaa gcc acc ctg       336
Ile Phe Asp Thr Cys Asn Thr Val Ser Lys Ala Leu Glu Ala Thr Leu
            100                 105                 110 agt ttt gtt gct caa aac aaa att gat tct ttg aac ctt gat gag ttc       384
Ser Phe Val Ala Gln Asn Lys Ile Asp Ser Leu Asn Leu Asp Glu Phe
        115                 120                 125 tgc aac tgc tca gag cac att ccc tct acg att gct gtg gtg gga gca       432
Cys Asn Cys Ser Glu His Ile Pro Ser Thr Ile Ala Val Val Gly Ala
    130                 135                 140 act ggc tca ggc gtc tcc acg gca gtg gca aat ctg ctg ggg ctc ttc       480
Thr Gly Ser Gly Val Ser Thr Ala Val Ala Asn Leu Leu Gly Leu Phe
145                 150                 155                 160 tac att ccc cag gtc agt tat gcc tcc tcc agc aga ctc ctc agc aac       528
Tyr Ile Pro Gln Val Ser Tyr Ala Ser Ser Ser Arg Leu Leu Ser Asn
                165                 170                 175 aag aat caa ttc aag tct ttc ctc cga acc atc ccc aat gat gag cac       576
Lys Asn Gln Phe Lys Ser Phe Leu Arg Thr Ile Pro Asn Asp Glu His
            180                 185                 190 cag gcc act gcc atg gca gac atc atc gag tat ttc cgc tgg aac tgg       624
Gln Ala Thr Ala Met Ala Asp Ile Ile Glu Tyr Phe Arg Trp Asn Trp
        195                 200                 205 gtg ggc aca att gca gct gat gac gac tat ggg cgg ccg ggg att gag       672
Val Gly Thr Ile Ala Ala Asp Asp Asp Tyr Gly Arg Pro Gly Ile Glu
    210                 215                 220 aaa ttc cga gag gaa gct gag gaa agg gat atc tgc atc gac ttc agt       720
Lys Phe Arg Glu Glu Ala Glu Glu Arg Asp Ile Cys Ile Asp Phe Ser
225                 230                 235                 240 gaa ctc atc tcc cag tac tct gat gag gaa gag atc cag cat gtg gta       768
Glu Leu Ile Ser Gln Tyr Ser Asp Glu Glu Glu Ile Gln His Val Val
                245                 250                 255 gag gtg att caa aat tcc acg gcc aaa gtc atc gtg gtt ttc tcc agt       816
Glu Val Ile Gln Asn Ser Thr Ala Lys Val Ile Val Val Phe Ser Ser
            260                 265                 270 ggc cca gat ctt gag ccc ctc atc aag gag att gtc cgg cgc aat atc       864
Gly Pro Asp Leu Glu Pro Leu Ile Lys Glu Ile Val Arg Arg Asn Ile
        275                 280                 285 acg ggc aag atc tgg ctg gcc agc gag gcc tgg gcc agc tcc tcc ctg       912
Thr Gly Lys Ile Trp Leu Ala Ser Glu Ala Trp Ala Ser Ser Ser Leu
    290                 295                 300 atc gcc atg cct cag tac ttc cac gtg gtt ggc ggc acc att gga ttc       960
Ile Ala Met Pro Gln Tyr Phe His Val Val Gly Gly Thr Ile Gly Phe
```

```
              305                 310                 315                 320
gct ctg aag gct ggg cag atc cca ggc ttc cgg gaa ttc ctg aag aag        1008
Ala Leu Lys Ala Gly Gln Ile Pro Gly Phe Arg Glu Phe Leu Lys Lys
                    325                 330                 335 gtc cat ccc agg aag tct gtc cac aat ggt ttt gcc aag gag ttt tgg        1056
Val His Pro Arg Lys Ser Val His Asn Gly Phe Ala Lys Glu Phe Trp
                340                 345                 350 gaa gaa aca ttt aac tgc cac ctc caa gaa ggt gca aaa gga cct tta        1104
Glu Glu Thr Phe Asn Cys His Leu Gln Glu Gly Ala Lys Gly Pro Leu
            355                 360                 365 cct gtg gac acc ttt ctg aga ggt cac gaa gaa agt ggc gac agg ttt        1152
Pro Val Asp Thr Phe Leu Arg Gly His Glu Glu Ser Gly Asp Arg Phe
        370                 375                 380 agc aac agc tcg aca gcc ttc cga ccc ctc tgt aca ggg gat gag aac        1200
Ser Asn Ser Ser Thr Ala Phe Arg Pro Leu Cys Thr Gly Asp Glu Asn
385                 390                 395                 400 atc agc agt gtc gag acc cct tac ata gat tac acg cat tta cgg ata        1248
Ile Ser Ser Val Glu Thr Pro Tyr Ile Asp Tyr Thr His Leu Arg Ile
                    405                 410                 415 tcc tac aat gtg tac tta gca gtc tac tcc att gcc cac gcc ttg caa        1296
Ser Tyr Asn Val Tyr Leu Ala Val Tyr Ser Ile Ala His Ala Leu Gln
                420                 425                 430 gat ata tat acc tgc tta cct ggg aga ggg ctc ttc acc aat ggc tcc        1344
Asp Ile Tyr Thr Cys Leu Pro Gly Arg Gly Leu Phe Thr Asn Gly Ser
            435                 440                 445 tgt gca gac atc aag aaa gtt gag gcg tgg cag gtc ctg aag cac cta        1392
Cys Ala Asp Ile Lys Lys Val Glu Ala Trp Gln Val Leu Lys His Leu
        450                 455                 460 cgg cat cta aac ttt aca aac aat atg ggg gag cag gtg acc ttt gat        1440
Arg His Leu Asn Phe Thr Asn Asn Met Gly Glu Gln Val Thr Phe Asp
465                 470                 475                 480 gag tgt ggt gac ctg gtg ggg aac tat tcc atc atc aac tgg cac ctc        1488
Glu Cys Gly Asp Leu Val Gly Asn Tyr Ser Ile Ile Asn Trp His Leu
                    485                 490                 495 tcc cca gag gat ggc tcc atc gtg ttt aag gaa gtc ggg tat tac aac        1536
Ser Pro Glu Asp Gly Ser Ile Val Phe Lys Glu Val Gly Tyr Tyr Asn
                500                 505                 510 gtc tat gcc aag aag gga gaa aga ctc ttc atc aac gag gag aaa atc        1584
Val Tyr Ala Lys Lys Gly Glu Arg Leu Phe Ile Asn Glu Glu Lys Ile
            515                 520                 525 ctg tgg agt ggg ttc tcc agg gag gtg ccc ttc tcc aac tgc agc cga        1632
Leu Trp Ser Gly Phe Ser Arg Glu Val Pro Phe Ser Asn Cys Ser Arg
        530                 535                 540 gac tgc ctg gca ggg acc agg aaa ggg atc att gag ggg gag ccc acc        1680
Asp Cys Leu Ala Gly Thr Arg Lys Gly Ile Ile Glu Gly Glu Pro Thr
545                 550                 555                 560 tgc tgc ttt gag tgt gtg gag tgt cct gat ggg gag tat agt gat gag        1728
Cys Cys Phe Glu Cys Val Glu Cys Pro Asp Gly Glu Tyr Ser Asp Glu
                    565                 570                 575 aca gat gcc agt gcc tgt aac aag tgc cca gat gac ttc tgg tcc aat        1776
Thr Asp Ala Ser Ala Cys Asn Lys Cys Pro Asp Asp Phe Trp Ser Asn
                580                 585                 590 gag aac cac acc tcc tgc att gcc aag cgt acg cgg ttc ctg gca tgg        1824
Glu Asn His Thr Ser Cys Ile Ala Lys Arg Thr Arg Phe Leu Ala Trp
            595                 600                 605 ggc gag ccg gct gtg ctg ctg ctc ctg ctg ctg agc ctg gcg ctg        1872
Gly Glu Pro Ala Val Leu Leu Leu Leu Leu Leu Ser Leu Ala Leu
        610                 615                 620 ggc ctt gtg ctg gct gct ttg ggg ctg ttc gtt cac cat cgg gac agc        1920
Gly Leu Val Leu Ala Ala Leu Gly Leu Phe Val His His Arg Asp Ser
```

```
                625                 630                 635                 640
cca ctg gtt cag gcc tcg ggg ggg ccc ctg gcc tgc ttt ggc ctg gtg                      1968
Pro Leu Val Gln Ala Ser Gly Gly Pro Leu Ala Cys Phe Gly Leu Val
                            645                 650                 655 tgc ctg ggc ctg gtc tgc ctc agc gtc ctc ctg ttc cct ggc cag ccc                      2016
Cys Leu Gly Leu Val Cys Leu Ser Val Leu Leu Phe Pro Gly Gln Pro
                660                 665                 670 agc cct gcc cga tgc ctg gcc cag cag ccc ttg tcc cac ctc ccg ctc                      2064
Ser Pro Ala Arg Cys Leu Ala Gln Gln Pro Leu Ser His Leu Pro Leu
            675                 680                 685 acg ggc tgc ctg agc aca ctc ttc ctg cag gcg gcc gag atc ttc gtg                      2112
Thr Gly Cys Leu Ser Thr Leu Phe Leu Gln Ala Ala Glu Ile Phe Val
        690                 695                 700 gag tca gaa ctg cct ctg agc tgg gca gac cgg ctg agt ggc tgc ctg                      2160
Glu Ser Glu Leu Pro Leu Ser Trp Ala Asp Arg Leu Ser Gly Cys Leu
705                 710                 715                 720 cgg ggg ccc tgg gcc tgg ctg gtg gtg ctg ctg gcc atg ctg gtg gag                      2208
Arg Gly Pro Trp Ala Trp Leu Val Val Leu Leu Ala Met Leu Val Glu
                725                 730                 735 gtc gca ctg tgc acc tgg tac ctg gtg gcc ttc ccg ccg gag gtg gtg                      2256
Val Ala Leu Cys Thr Trp Tyr Leu Val Ala Phe Pro Pro Glu Val Val
            740                 745                 750 acg gac tgg cac atg ctg ccc acg gag gcg ctg gtg cac tgc cgc aca                      2304
Thr Asp Trp His Met Leu Pro Thr Glu Ala Leu Val His Cys Arg Thr
        755                 760                 765 cgc tcc tgg gtc agc ttc ggc cta gcg cac gcc acc aat gcc acg ctg                      2352
Arg Ser Trp Val Ser Phe Gly Leu Ala His Ala Thr Asn Ala Thr Leu
    770                 775                 780 gcc ttt ctc tgc ttc ctg ggc act ttc ctg gtg cgg agc cag ccg ggc                      2400
Ala Phe Leu Cys Phe Leu Gly Thr Phe Leu Val Arg Ser Gln Pro Gly
785                 790                 795                 800 cgc tac aac cgt gcc cgt ggc ctc acc ttt gcc atg ctg gcc tac ttc                      2448
Arg Tyr Asn Arg Ala Arg Gly Leu Thr Phe Ala Met Leu Ala Tyr Phe
                805                 810                 815 atc acc tgg gtc tcc ttt gtg ccc ctg gcc aat gtg cag gtg gtc                          2496
Ile Thr Trp Val Ser Phe Val Pro Leu Ala Asn Val Gln Val Val
            820                 825                 830 ctc agg ccc gcc gtg cag atg ggc gcc ctc ctg ctc tgt gtc ctg ggc                      2544
Leu Arg Pro Ala Val Gln Met Gly Ala Leu Leu Leu Cys Val Leu Gly
        835                 840                 845 atc ctg gct gcc ttc cac ctg ccc agg tgt tac ctg ctc atg cgg cag                      2592
Ile Leu Ala Ala Phe His Leu Pro Arg Cys Tyr Leu Leu Met Arg Gln
    850                 855                 860 cca ggg ctc aac acc ccc gag ttc ttc ctg gga ggg ggc cct ggg gat                      2640
Pro Gly Leu Asn Thr Pro Glu Phe Phe Leu Gly Gly Gly Pro Gly Asp
865                 870                 875                 880 gcc caa ggc cag aat gac ggg aac aca gga aat cag ggg aaa cat gag                      2688
Ala Gln Gly Gln Asn Asp Gly Asn Thr Gly Asn Gln Gly Lys His Glu
                885                 890                 895 tga                                                                                  2691

<210> SEQ ID NO 22
<211> LENGTH: 896
<212> TYPE: PRT
<213> ORGANISM: artificial
<220> FEATURE:
<223> OTHER INFORMATION: Synthetic Construct

<400> SEQUENCE: 22

Met Ala Phe Tyr Ser Cys Cys Trp Val Leu Leu Ala Leu Thr Trp His
1               5                   10                  15
```

Thr Ser Ala Tyr Gly Pro Asp Gln Arg Ala Gln Lys Lys Gly Asp Ile
                20                  25                  30

Ile Leu Gly Gly Leu Phe Pro Ile His Phe Gly Val Ala Ala Lys Asp
            35                  40                  45

Gln Asp Leu Lys Ser Arg Pro Glu Ser Val Glu Cys Ile Arg Tyr Asn
50                  55                  60

Phe Arg Gly Phe Arg Trp Leu Gln Ala Met Ile Phe Ala Ile Glu Glu
65                  70                  75                  80

Ile Asn Ser Ser Pro Ala Leu Leu Pro Asn Leu Thr Leu Gly Tyr Arg
                85                  90                  95

Ile Phe Asp Thr Cys Asn Thr Val Ser Lys Ala Leu Glu Ala Thr Leu
                100                 105                 110

Ser Phe Val Ala Gln Asn Lys Ile Asp Ser Leu Asn Leu Asp Glu Phe
                115                 120                 125

Cys Asn Cys Ser Glu His Ile Pro Ser Thr Ile Ala Val Val Gly Ala
130                 135                 140

Thr Gly Ser Gly Val Ser Thr Ala Val Ala Asn Leu Leu Gly Leu Phe
145                 150                 155                 160

Tyr Ile Pro Gln Val Ser Tyr Ala Ser Ser Arg Leu Leu Ser Asn
                165                 170                 175

Lys Asn Gln Phe Lys Ser Phe Leu Arg Thr Ile Pro Asn Asp Glu His
                180                 185                 190

Gln Ala Thr Ala Met Ala Asp Ile Ile Glu Tyr Phe Arg Trp Asn Trp
                195                 200                 205

Val Gly Thr Ile Ala Ala Asp Asp Tyr Gly Arg Pro Gly Ile Glu
210                 215                 220

Lys Phe Arg Glu Glu Ala Glu Glu Arg Asp Ile Cys Ile Asp Phe Ser
225                 230                 235                 240

Glu Leu Ile Ser Gln Tyr Ser Asp Glu Glu Ile Gln His Val Val
                245                 250                 255

Glu Val Ile Gln Asn Ser Thr Ala Lys Val Ile Val Val Phe Ser Ser
                260                 265                 270

Gly Pro Asp Leu Glu Pro Leu Ile Lys Glu Ile Val Arg Arg Asn Ile
                275                 280                 285

Thr Gly Lys Ile Trp Leu Ala Ser Glu Ala Trp Ala Ser Ser Ser Leu
                290                 295                 300

Ile Ala Met Pro Gln Tyr Phe His Val Val Gly Gly Thr Ile Gly Phe
305                 310                 315                 320

Ala Leu Lys Ala Gly Gln Ile Pro Gly Phe Arg Glu Phe Leu Lys Lys
                325                 330                 335

Val His Pro Arg Lys Ser Val His Asn Gly Phe Ala Lys Glu Phe Trp
                340                 345                 350

Glu Glu Thr Phe Asn Cys His Leu Gln Glu Gly Ala Lys Gly Pro Leu
                355                 360                 365

Pro Val Asp Thr Phe Leu Arg Gly His Glu Glu Ser Gly Asp Arg Phe
                370                 375                 380

Ser Asn Ser Ser Thr Ala Phe Arg Pro Leu Cys Thr Gly Asp Glu Asn
385                 390                 395                 400

Ile Ser Ser Val Glu Thr Pro Tyr Ile Asp Tyr Thr His Leu Arg Ile
                405                 410                 415

Ser Tyr Asn Val Tyr Leu Ala Val Tyr Ser Ile Ala His Ala Leu Gln
                420                 425                 430

Asp Ile Tyr Thr Cys Leu Pro Gly Arg Gly Leu Phe Thr Asn Gly Ser

-continued

```
            435                 440                 445
Cys Ala Asp Ile Lys Lys Val Glu Ala Trp Gln Val Leu Lys His Leu
            450                 455                 460
Arg His Leu Asn Phe Thr Asn Asn Met Gly Glu Gln Val Thr Phe Asp
465                 470                 475                 480
Glu Cys Gly Asp Leu Val Gly Asn Tyr Ser Ile Ile Asn Trp His Leu
                    485                 490                 495
Ser Pro Glu Asp Gly Ser Ile Val Phe Lys Glu Val Gly Tyr Tyr Asn
                500                 505                 510
Val Tyr Ala Lys Lys Gly Glu Arg Leu Phe Ile Asn Glu Glu Lys Ile
                515                 520                 525
Leu Trp Ser Gly Phe Ser Arg Glu Val Pro Phe Ser Asn Cys Ser Arg
            530                 535                 540
Asp Cys Leu Ala Gly Thr Arg Lys Gly Ile Ile Glu Gly Glu Pro Thr
545                 550                 555                 560
Cys Cys Phe Glu Cys Val Glu Cys Pro Asp Gly Glu Tyr Ser Asp Glu
                    565                 570                 575
Thr Asp Ala Ser Ala Cys Asn Lys Cys Pro Asp Asp Phe Trp Ser Asn
                580                 585                 590
Glu Asn His Thr Ser Cys Ile Ala Lys Arg Thr Arg Phe Leu Ala Trp
            595                 600                 605
Gly Glu Pro Ala Val Leu Leu Leu Leu Leu Leu Ser Leu Ala Leu
            610                 615                 620
Gly Leu Val Leu Ala Ala Leu Gly Leu Phe Val His His Arg Asp Ser
625                 630                 635                 640
Pro Leu Val Gln Ala Ser Gly Gly Pro Leu Ala Cys Phe Gly Leu Val
                    645                 650                 655
Cys Leu Gly Leu Val Cys Leu Ser Val Leu Leu Phe Pro Gly Gln Pro
                660                 665                 670
Ser Pro Ala Arg Cys Leu Ala Gln Gln Pro Leu Ser His Leu Pro Leu
                675                 680                 685
Thr Gly Cys Leu Ser Thr Leu Phe Leu Gln Ala Ala Glu Ile Phe Val
            690                 695                 700
Glu Ser Glu Leu Pro Leu Ser Trp Ala Asp Arg Leu Ser Gly Cys Leu
705                 710                 715                 720
Arg Gly Pro Trp Ala Trp Leu Val Val Leu Leu Ala Met Leu Val Glu
                    725                 730                 735
Val Ala Leu Cys Thr Trp Tyr Leu Val Ala Phe Pro Pro Glu Val Val
                740                 745                 750
Thr Asp Trp His Met Leu Pro Thr Glu Ala Leu Val His Cys Arg Thr
            755                 760                 765
Arg Ser Trp Val Ser Phe Gly Leu Ala His Ala Thr Asn Ala Thr Leu
            770                 775                 780
Ala Phe Leu Cys Phe Leu Gly Thr Phe Leu Val Arg Ser Gln Pro Gly
785                 790                 795                 800
Arg Tyr Asn Arg Ala Arg Gly Leu Thr Phe Ala Met Leu Ala Tyr Phe
                    805                 810                 815
Ile Thr Trp Val Ser Phe Val Pro Leu Leu Ala Asn Val Gln Val Val
                820                 825                 830
Leu Arg Pro Ala Val Gln Met Gly Ala Leu Leu Leu Cys Val Leu Gly
            835                 840                 845
Ile Leu Ala Ala Phe His Leu Pro Arg Cys Tyr Leu Leu Met Arg Gln
            850                 855                 860
```

```
Pro Gly Leu Asn Thr Pro Glu Phe Phe Leu Gly Gly Gly Pro Gly Asp
865                 870                 875                 880

Ala Gln Gly Gln Asn Asp Gly Asn Thr Gly Asn Gln Gly Lys His Glu
            885                 890                 895

<210> SEQ ID NO 23
<211> LENGTH: 28
<212> TYPE: DNA
<213> ORGANISM: artificial
<220> FEATURE:
<223> OTHER INFORMATION: primer

<400> SEQUENCE: 23
atatcgtacg cttggcaatg caggaggt                                            28

<210> SEQ ID NO 24
<211> LENGTH: 28
<212> TYPE: DNA
<213> ORGANISM: artificial
<220> FEATURE:
<223> OTHER INFORMATION: primer

<400> SEQUENCE: 24
atatcgtacg gtcttcctgg aatggcat                                            28

<210> SEQ ID NO 25
<211> LENGTH: 28
<212> TYPE: DNA
<213> ORGANISM: artificial
<220> FEATURE:
<223> OTHER INFORMATION: primer

<400> SEQUENCE: 25
atatcgtacg cggttcctgg catggggc                                            28
```

CHIMERIC PROTEINS AND THEIR USE IN METHODS TO SCREEN FOR SWEET TASTE MODULATORS

CROSS REFERENCE TO RELATED APPLICATIONS

This application is a national stage application of International Application No. PCT/EP2007/04710, filed 18 Dec. 2008, which claims the benefit of U.S. Application Ser. No. 60/814,866, filed 19 Jun. 2006 and U.S. Application Ser. No. 60/881,402, filed 19 Jan. 2007 from which applications priority is claimed, and which are incorporated herein by reference.

Sweetness modulators and in particular sweetness enhancers are of great interest to the food and flavor industry, for example, to allow reduction of sweeteners including sugars or artificial sweeteners. The use of sweetness enhancers can reduce calories, prevent teeth from damage by sugars, and avoid or reduce the bitter/metallic off- and aftertastes associated with many artificial sweeteners.

To screen for sweetness modifiers or enhancers, known screens employing the T1R2/T1R3 heterodimeric sweet receptor can be used.

To identify or characterise a sweetness modifier/enhancer, usually the results of samples with and without potential enhancer/modifier, both samples additionally containing a sweetener, are compared. However, sweeteners and in particular sugars have a great effect on osmolarity, and/or are viscous. Due to changes in properties of the samples such as viscosity and osmolarity, artifacts may occur that cause incorrect results when using standard screening methods.

Another disadvantage of known screens is that the wild-type T1R2/T1R3 receptor comprises several binding domains, in particular the extracellular amino terminal domains including the venus flytrap ("VFT") domain that bind to carbohydrate sweeteners such as sucrose, glucose, fructose as well as the artificial sweeteners aspartame and sucralose. Therefore, a screen for specific modulators of specific ligands, and in particular for ligands of the transmembrane domains ("TMD(s)") and cystein-rich domains of T1R2 and/or T1R3, excluding the VFT ligands, is not possible with known screening methods.

Agonists that bind in the TMD of T1R3 are cyclamate and Neohesperidin Dihydrochalcone (NDHC). Sucrose and sucralose bind in the VFTs of T1R2 and T1R3, asparatame binds in the VFT of T1R2.

In order to prevent identification of agents that may compete with sugars for binding to the receptor, a screen that allows identification of sweet receptor modulators that bind at a site physically distinct from the VFT domains, and in particular in the TMD and/or cysteine-rich domains, would be desirable.

SUMMARY

The screening methods and binding assays that are provided avoid the above problems and allow for improved results by using CSR::T1R chimeric proteins.

In a first aspect, provided is a CSR::T1R chimeric protein able to bind to at least one sweetener or sweetness enhancer, comprising one or more CSR::T1R selected from the group consisting of a CSR::T1R2 polypeptide substantially homologous to SEQ ID NO:2 (CSR::T1R2-a) or SEQ ID NO:20 (CSR::T1R2-b) with a sequence identity of at least 90%, a CSR::T1R3 polypeptide substantially homologous to SEQ ID NO:4 (CSR::T1R3-a) or SEQ ID NO: 22 (CSR::T1R3-b) with a sequence identity of at least 90%.

In another aspect, provided is a CSR::T1R chimeric protein as defined herein-above comprising two polypeptide subunits in form of a heterodimeric protein selected from the group consisting of a CSR::T1R2/CSR::T1R3 heterodimeric chimeric protein, a CSR::T1R2/T1R3 heterodimeric chimeric protein, and a T1R2/CSR::T1R3 heterodimeric chimeric protein, wherein the T1R2 subunit of the heterodimer comprises a polypeptide a polypeptide essentially homologous to SEQ ID NO:8 with a sequence identity of at least 90%; and wherein the T1R3 subunit of the heterodimer comprises a polypeptide essentially homologous to SEQ ID NO:10 with a sequence identity of at least 90%.

In another aspect, provided is a CSR::T1R chimeric protein comprising two polypeptide subunits as defined herein-above which is a CSR::T1R2/CSR::T1R3 heterodimeric chimeric protein including but not limited to a CSR::T1R2-a/CSR::T1R3-a heterodimeric protein, a CSR::T1R2-b/CSR::T1R3-b heterodimeric protein, a CSR::T1R2-a/CSR::T1R3-b heterodimeric protein, a CSR::T1R2-b/CSR::T1R3-a heterodimeric protein, or a heterodimeric protein substantially homologous thereto as herein defined, wherein CSR::T1R2-a corresponds to SEQ ID NO: 2, CSR::T1R2-b corresponds to SEQ ID NO:20, CSR::T1R3-a corresponds to SEQ ID NO:4 and CSR::T1R3-b corresponds to SEQ ID NO:22.

In another aspect, provided is a nucleic acid encoding a CSR::T1R chimeric protein able to bind at least one sweetener or sweetness enhancer comprising one or more of a nucleic acid substantially homologous to a nucleotide sequence selected from the group consisting of SEQ ID NO:1 (CSR::T1R2-a), SEQ ID NO: 19 (CSR::T1R2-b); SEQ ID NO:3 (CSR::T1R3-a), and SEQ ID NO: 21 (CSR::T1R3-b), as determined by sequence identity, a nucleic acid substantially homologous to a nucleotide sequence selected from the group consisting of SEQ ID NO:1 (CSR::T1R2-a), SEQ ID NO: 19 (CSR::T1R2-b); SEQ ID NO:3 (CSR::T1R3-a), and SEQ ID NO: 21 (CSR::T1R3-b), as determined by hybridisation, a nucleic acid substantially homologous to a nucleotide sequence encoding the CSR::T1R chimeric protein as defined in claim 1, wherein the substantially homologous nucleic acid as determined by sequence identity has a sequence identity of at least 90%; wherein the substantially homologous nucleic acid as determined by hybridisation hybridises under stringent hybridization conditions at a temperature of 42° C. in a solution consisting of 50% formamide, 5×SSC, and 1% SDS, and washing at 65° C. in a solution consisting of 0.2×SSC and 0.1% SDS; wherein the nucleic acid optionally comprises SEQ ID NO:6 (HSV tag) at or near its end to form the C-terminus in the corresponding protein.

In another aspect, provided is an expression vector comprising the nucleic acid as defined herein-above.

In another aspect, provided is a host cell transfected with an expression vector as defined in herein-above.

In another aspect, provided is a host cell as described herein-above stably expressing a CSR::T1R chimeric protein as defined herein-above and a G-Protein, optionally a G-Protein substantially homologous to Gaq-Gustducin.

In another aspect, provided is a host cell as described herein-above, transiently expressing a CSR::T1R chimeric protein as described herein-above and a G-Protein, optionally a G-Protein substantially homologous to Gaq-Gustducin.

In another aspect, provided is a method of producing a CSR::T1R chimeric protein as defined herein-above, comprising the step of culturing host cells comprising an expression vector encoding for the CSR::T1R chimeric protein, under conditions sufficient for expression, thereby forming the CSR::T1R chimeric protein and optionally recovering it from the cells.

In another aspect, provided is a method to identify an agent that modulates sweet taste signaling in taste cells, the method comprising:

(i) contacting cells that express a CSR::T1R chimeric protein that responds to stimuli selected from sweet taste stimuli and calcium stimuli with an agent thereby providing a functional response, optionally in presence of another agent; and (ii) determining whether at least one agent affects the functional response of said CSR::T1R chimeric protein in said cells by at least one functional response in said cells;

wherein said CSR::T1R chimeric protein is as defined herein-above.

In another aspect, provided is a method as defined herein-above wherein the cells also express a G-Protein.

In another aspect, provided is a method as defined herein-above wherein the G-Protein is a chimeric G-protein substantially homologous to Gaq-Gustducin.

In another aspect, provided is a method as defined herein-above wherein the G-Protein is the chimeric G-protein G alpha 16-gustducin 44.

In another aspect, provided is a method as defined herein-above wherein step (ii) is performed by measuring a change in or caused by intracellular messengers.

In another aspect, provided is a method as defined herein-above wherein the functional response is determined by measuring a change in an intracellular messenger selected from IP3 and calcium$^{2+}$.

In another aspect, provided is a method as defined herein-above wherein said cells are selected from the group consisting of bacterial cells, eucaryotic cells, yeast cells, insect cells, mammalian cells, amphibian cells, and worm cells.

In another aspect, provided is a method as described herein-above, wherein the cell is a mammalian cell.

In another aspect, provided is a method as described herein-above wherein the cell is a mammalian cell selected from the group consisting of CHO, COS, HeLa and HEK-293 cells.

In another aspect, provided is a method as described herein-above, wherein step (i) further comprises contacting the CSR::T1R chimeric protein with a test agent in presence of calcium.

In another aspect, provided is a method as described herein-above, wherein the calcium is provided in the form of calcium chloride.

In another aspect, provided is a kit comprising
(i) recombinant cells that express a CSR::T1R chimeric protein as defined herein-above, and
(ii) an agonist of the CSR::T1R chimeric protein,
for combined use to identify test agents as modulators of the CSR::T1R chimeric protein.

In another aspect, provided is a method of using the kit as defined herein-above comprising:
(i) growing recombinant cells that express a CSR::T1R chimeric protein as defined herein-above;
(ii) adding test agents in the presence of an agonist in a suitable concentration;
(iii) determining a change in a functional response of the cells by comparing the response in presence and absence of the test agent, and the test agent is thereby identified as a modulator of the CSR::T1R chimeric protein as defined herein-above.

In another aspect, provided is a method to identify an agent that modulates the CSR::T1R chimeric protein as defined herein-above, the method comprising:
(i) measuring a parameter that changes in response to a ligand binding to the CSR::T1R chimeric protein, and
(ii) determining a change of the parameter in response to a test agent, optionally in presence of a ligand, in comparison to a negative control and thereby identifying a modulator or ligand.

In another aspect, provided is a method as defined herein-above wherein the ligand is selected from the group consisting of calcium, calcium ions and calcium chloride.

In another aspect, provided is a method as defined herein-above, wherein step (i) is performed by a method selected from the group consisting of fluorescence spectroscopy, NMR spectroscopy, measuring of one or more of absorbance, refractive index, hydrodynamic methods, chromatography, measuring solubility, biochemical methods, wherein the methods measure the properties of the CSR::T1R chimeric protein in a suitable environment selected form the group consisting of solution, bilayer membrane, attached to a solid phase, in a lipid monolayer, bound on a membrane, and in vesicles.

DETAILED DESCRIPTION

CSR::T1R chimeric proteins include but are not limited to a CSR::T1R2 monomer, a CSR::T1R3 monomer, a CSR::T1R2/CSR::T1R3 heterodimer, a CSR::T1R2/T1R3 heterodimer (chimeric T1R2 subunit with wildtype T1R3), and a T1R2/CSR::T1R3 heterodimer (chimeric T1R3 subunit with wildtype T1R2).

CSR::T1R2 includes but is not limited to CSR::T1R2-a and CSR::T1R2-b.

CSR::T1R3 includes but is not limited to CSR::T1R3-a or CSR::T1R3-b.

Each -a variant differs from the relevant -b variant in the exact location where the two parts of different origin (CSR and T1R, respectively) are joined to give the chimeric CSR::T1R protein. Variants-a are joined just before the cysteine-rich domain (CRD), variants-b are joined just after the CRD, as is apparent from their sequences (SEQ ID NO: 1+2:CSR::T1R2-a nucleic acid+protein; SEQ ID NO: 3+4:CSR::T1R3-a nucleic acid+protein; SEQ ID NO: 19+20:CSR::T1R2-b nucleic acid+protein; SEQ ID NO: 21+22:CSR::T1R3-b nucleic acid+protein).

Each chimeric subunits may be combined with each other chimeric subunit or the wildtype subunit. Accordingly, the CSR::T1R chimeric proteins include, in particular, a CSR::T1R2-a monomer, a CSR::T1R3-a monomer, a CSR::T1R2-a/CSR::T1R3-a heterodimer, a CSR::T1R2-a/T1R3 heterodimer (chimeric T1R2-a subunit with wildtype T1R3), and a T1R2/CSR::T1R3-a heterodimer (chimeric T1R3-a subunit with wildtype T1R2), as well as a CSR::T1R2-b monomer, a CSR::T1R3-b monomer, a CSR::T1R2-b/CSR::T1R3-b heterodimer, a CSR::T1R2-b/T1R3 heterodimer (chimeric T1R2-a subunit with wildtype T1R3), a T1R2/CSR::T1R3-b heterodimer (chimeric T1R3-a subunit with wildtype T1R2), a CSR::T1R2-a/CSR::T1R3-b heterodimer, and a CSR::T1R2-b/CSR::T1R3-a heterodimer.

The CSR:T1R chimeric protein does not possess the VFT domains of T1R2, T1R3, or T1R2 and T1R3, and therefore allows specifically identification of compounds that bind to the TMD domains and the cystein-rich domains of T1R2 and/or T1R3. These identified compounds are of particular interest as they would not be expected to compete with carbohydrates binding in the VFT site for binding to the sweet taste receptor in vivo and are therefore particularly interesting potential candidates for sweetness enhancers of carbohydrates.

Chimeric proteins are joined fragments of two or more original proteins that sometimes are able to combine desired properties or eliminate unwanted ones. As the folding of a protein in the three dimensional space is critical and the position of amino acids will influence the folding, not any two fragments can be joined. Even if critical domains and amino acids are known, the successful expression, correct folding and intact functionality of desired properties is very much unpredictable.

Applicant has found that the chimeric monomers, CSR::T1R2 and CSR::T1R3, are functional and are able to form a functional CSR::T1R2/CSR::T1R3 heterodimer (see examples for the CSR::T1R2-a/CSR::T1R3-a and CSR::T1R2-b/CSR::T1R3-b heterodimers; CSR::T1R2-a/CSR::T1R3-b and CSR::T1R2-b/CSR::T1R3-a heterodimers may also work). Experiments of the applicant indicate that the CSR::T1R2 monomeric subunit also functions as a functional sweet receptor on its own, without forming a heterodimer. Preliminary experiments indicate that the CSR::T1R3 may have difficulties in engaging and/or activating certain G-proteins; however, CSR::T1R3 is useful in binding assays that do not require the ability to activate a G-Protein.

Accordingly, CSR::T1R2 and CSR::T1R3 are also useful in their monomeric form in the methods described herein. Alternative heterodimers that can be used in these methods are chimeric subunit/wildtype subunit heterodimers (CSR::T1R2/T1R3 and T1R2/CSR::T1R3).

In the CSR::T1R2/CSR::T1R3 heterodimer, each of the CSR::T1R subunits of the heterodimeric complex consist of joined sequence fragments from two source proteins. The two source proteins are the human calcium-sensing receptor (hCaSR), and a T1R protein (T1R2 or T1R3). The hCaSR-derived fragment (CSR) common to both subunits comprises the extracellular domain (ECD) of hCaSR. The T1R-derived fragments comprise the transmembrane domains (TMD) of the T1R sequences and differ, as they are derived from either T1R2 or T1R3.

The chimeric protein allows to use calcium as a ligand/agonist for receptor activation instead of sweeteners, so that any adverse effects due to the presence of sweeteners can be avoided.

The term CSR::T1R, as used herein, designates the CSR::T1R2 homomer; or the CSR::T1R3 homomer; or the heterodimeric complex of CSR::T1R2 with CSR::T1R3 or with the wildtype T1R3 (CSR::T1R2/CSR::T1R3 or CSR::T1R2/T1R3); or the heterodimeric complex of CSR::T1R3 with CSR::T1R2 or with the wildtype T1R2 (CSR::T1R2/CSR::T1R3 or T1R2/CSR::T1R3).

More generally, as the receptor is coupled to a G-Protein in vivo and in many in vitro methods, CSR::T1R is also referred to as "the GPCR".

The chimeric CSR::T1R constructs that are provided (DNA, vectors, transfected cells, proteins) are useful when screening, without limitation, for modulators of the sweet taste response, for example, without limitation, sweetness enhancers. Traditional screening methods and binding assays may be used to screen for modulators and enhancers. Such screening methodology is well-known in the art, and is outlined below.

Alternatively, as the CSR (part of the hCaSR) in the chimeric CSR::T1R constructs renders the resulting receptors responsive to calcium, when screening for a modulator in presence/absence of a ligand/agonist of the T1R receptor, the ligand is replaced with calcium (for example, without limitation, in the form of calcium chloride). This has the additional advantage of avoiding any negative effects of the actual ligand/agonist being present. For example, when screening for modulators of sugar ligands/agonists, the adverse effects of sugars on osmolarity etc. is avoided.

Cells Used in the Assays:

Transfected or endogenous T1R3 and T1R2 can negatively interfere with methods that determine agonist responses of CSR::T1R2 and/or CSR::T1R3, respectively, or the change of said responses dependent on another modulator. The absence of T1R3 and T1R2 provides a null background for the determination of CSR::T1R2 and/or CSR::T1R3 activation, so that observed signals can be directly attributed to CSR::T1R2 and/or CSR::T1R3 activity. This allows the identification of agents that specifically modulate CSR::T1R2 and/or CSR::T1R3, and excludes agents that activates the wildtype T1R2 and T1R3, which could in the case of T1R3 also include umami tastants, as T1R3 is part of both the sweet and the umami heterodimers.

The presence of the endogenous wildtype T1R2 and/or T1R3 will cause some backgrounds signals, which are undesirable. While cells with endogenous T1R2 and/or T1R3 can still be useful to obtain results with sufficiently low background, a better choice are cells that do not contain the endogenous T1R2 and T1R3 receptors. An exception occurs when using a CSR::T1R2/T1R3 chimeric protein, which may contain wildtype T1R3 without adverse effect on the background, or a T1R2/CSR::T1R3 chimeric protein, which may contain wildtype T1R2 without adverse effects on the background.

The cells listed below are particularly useful as they do not contain endogenous/wildtype T1R3, or endogenous wildtype T1R2.

However, alternative cells are also useful in the methods described herein.

Suitable eucaryotic cells include eucaryotic cells, for example, without limitation, mammalian cells, yeast cells, or insect cells (including Sf9), amphibian cells (including melanophore cells), or worm cells including cells of *Caenorhabditis* (including *Caenorhabditis elegans*).

Suitable mammalian cells include, for example, without limitation, COS cells (including Cos-1 and Cos-7), CHO cells, HEK293 cells, HEK293T cells, HEK293 T-Rex™ cells, or other transfectable eucaryotic cell lines.

Suitable bacterial cells include without limitation *E. coli*.

Cells may be transfected with a GPCR and a G-protein (which links the receptor to a phospholipase C signal transduction pathway) transiently or stably, as is well known in the art. An excellent heterologous expression system that employs the chimeric G-protein G alpha 16-gustducin 44 (also known as G.sub.alpha.16 gust(ducin)44, G.sub.alpha.16gust(ducin)44, Gα16gust(ducin)44, Gα16gust(ducin)44, Gα16-gustducin 44, or as used hereinbelow, "G16gust44") which provides for enhanced coupling to taste GPCRs, is described in detail in WO 2004/055048. Alternatively, other chimeric G-proteins based on Gaq-Gustducin described in WO 2004/055048, or other G-Proteins, for example, G16 or G15, may also be used.

The CSR::T1R can be expressed in a cell with a G-protein that links the receptor to a signal transduction pathway, for example, the phospholipase C signal transduction pathway, or signal transduction pathways including, for example, the following: adenylate cyclase, guanylate cyclase, phospholipase C, IP3, GTPase/GTP binding, arachinoid acid, cAMP/cGMP, DAG, protein kinase c (PKC), MAP kinase tyrosine kinase, or ERK kinase.

Alternatively, any suitable reporter gene may be linked to a CSR::T1R-activation responsive promoter and used to determine CSR::T1R activity, as described in more detail hereinbelow.

Vector Constructs Used in Cells Described Herein-Above:

The vector constructs for expressing the GPCR and/or the G-protein in such cells may be produced in a manner known per se using Polymerase Chain Reactions. After verification of the sequence, cDNA fragments may be sub-cloned into a suitable vector, for example pcDNA 3.1 mammalian expression vector for mammalian cells, and transiently transfected in a corresponding host cell to enable the correct expression of the gene.

After a post-transfection period, for example 48 hours, cell lysates may be prepared, analysed by a Western-Blot analysis in order to confirm the correct expression of the protein. Once correct protein expression is confirmed, suitable cells, for example mammalian cells including HEK293T cells and HEK T-Rex™, may be transfected to generate cells stably expressing the protein according to techniques well known in the art.

Alternatively, a variety of non-mammalian expression vector/host systems can be used to contain and express sequences encoding the CSR::T1R G-Protein coupled receptor (GPCR). These include, for example, microorganisms including bacteria transformed with recombinant bacteriophage, plasmid, or cosmid DNA expression vectors; yeast transformed with yeast expression vectors; insect cell systems infected with viral expression vectors (for example baculovirus), or with bacterial expression vectors (for example pBR322 plasmids).

Examples of specific vectors that may be used with the systems described herein-above are described in "G-protein coupled receptors (Signal Transduction Series)"; Editors: Tatsuya Haga and Gabriel Berstein, 1st ed., CRC Press—Boca Raton Fla.; September 1999.

In bacterial systems, a number of cloning and expression vectors may be selected depending upon the use intended for polynucleotide sequences encoding the GPCR. For example, routine cloning, subcloning, and propagation of polynucleotide sequences encoding a GPCR can be achieved using a multifunctional *E. coli* vector such as pBLUESCRIPT (Stratagene, La Jolla Calif.) or pSPORT1 plasmid (Life Technologies). Ligation of sequences encoding a GPCR into the vector's multiple cloning site disrupts the lacZ gene, allowing a colorimetric screening procedure for identification of transformed bacteria containing recombinant molecules. In addition, these vectors may be useful for in vitro transcription, dideoxy sequencing, single strand rescue with helper phage, and creation of nested deletions in the cloned sequence. When large quantities of a GPCR are needed, for example, for the production of antibodies, vectors which direct high level expression of a GPCR may be used. For example, vectors containing the strong, inducible SP6 or T7 bacteriophage promoter may be used.

Yeast expression systems may be used for production of a GPCR. A number of vectors containing constitutive or inducible promoters, such as alpha factor, alcohol oxidase, and PGH promoters, may be used in the yeast *Saccharomyces cerevisiae* or *Pichia pastoris*. In addition, such vectors direct either the secretion or intracellular retention of expressed proteins and enable integration of foreign sequences into the host genome for stable propagation.

For the expression of heterologous proteins in insect cell lines is, for example, derivatives of the Lepidopteran baculovirus, *Autographa californica* multicapsid nucleo-virus (AcMNPV) can be used. In this system, foreign gene expression is directed by a very strong late viral promoter, either the polyhedrin or p10 promoters, and a wide array of vectors is available that optimises expression and recovery of recombinant proteins. These vectors enable expression of both membrane-bound and secreted proteins at high levels, and also many post-translational modifications known to occur in mammalian systems, including N- and O-linked glycosylation, phosphorylation, acylation, proteolysis and secreted vaccine components. A number of vectors are commercially available, for example the InsectSelect™ System from Invitrogen.

Expression Systems:

In order to express cDNAs encoding the desired proteins (GPCR (CSR::T1R) and G-protein), one typically subclones the appropriate cDNA into an expression vector that contains a strong promoter to direct transcription, a transcription/translation terminator, and a ribosome-binding site for translational initiation. Suitable bacterial promoters are well known in the art, for example, *E. coli, Bacillus* sp., and *Salmonella*, and kits for such expression systems are commercially available. Similarly, eukaryotic expression systems for mammalian cells, yeast, and insect cells are commercially available. The eukaryotic expression vector may be, for example, an adenoviral vector, an adeno-associated vector, or a retroviral vector.

In addition to the promoter, the expression vector typically contains a transcription unit or expression cassette that contains all the additional elements required for the expression of the protein-encoding nucleic acid in host cells. A typical expression cassette thus contains a promoter operably linked to the nucleic acid sequence encoding the protein and signals required for efficient polyadenylation of the transcript, ribosome binding sites, and translation termination. The nucleic acid sequence encoding the protein may typically be linked to a membrane-targeting signal such as the N-terminal 45 amino acids of the rat Somatostatin-3 receptor sequence to promote efficient cell-surface expression of the recombinant protein, which is useful for cell-surface receptors. Additional elements may include, for example, enhancers.

An expression cassette should also contain a transcription termination region downstream of the structural gene to provide for efficient termination. The termination region may be obtained from the same gene as the promoter sequence or may be obtained from different genes.

For expression of the proteins, conventional vectors for expression in eucaryotic or procaryotic cells well known in the art may be used. Examples of vectors include bacterial expression vectors, for example, plasmids including pBR322-based plasmids, pSKF, and pET23D, and fusion expression systems, for example, GST and LacZ.

Expression vectors containing regulatory elements from eukaryotic viruses are typically used in eukaryotic expression vectors, for example SV40 vectors, cytomegalovirus vectors, papilloma virus vectors, and vectors derived from Epstein-Barr virus. Other exemplary eukaryotic vectors include pMSG, pAV009/A$^+$, pMTO10/A$^+$, pMAMneo-5, baculovirus pDSVE, pcDNA3.1, pIRES and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, dihydrofolate reductase and the like.

The elements that are typically included in expression vectors may also include a replicon that functions in *E. coli*, a gene encoding drug resistance to permit selection of bacteria that harbor recombinant plasmids, and unique restriction sites in non-essential regions of the plasmid to allow insertion of eukaryotic sequences. The particular drug resistance gene chosen is not critical, any of the many drug resistance genes known in the art are suitable. The prokaryotic sequences are optionally chosen such that they do not interfere with the replication of the DNA in eukaryotic cells, if necessary.

In bacterial systems the GPCR cDNA fragment may be expressed alone or as a fusion protein wherein the GPCR of interest is fused to the *E. coli* periplasmic maltose-binding protein (MBP) wherein the MBP, including its signal peptide, is linked to the amino terminus of the GPCR. The wild-type GPCR cDNA or the MBP:GPCR fusion cDNA is subcloned into a suitable plasmid, for example pBR322, where in *E. coli*, GPCR expression is driven by the /ac wild-type promoter. Methods of expression of GPCRs in *E. coli* are described, for example, in "G-protein coupled receptors (Signal Transduction Series)"; Editors: Tatsuya Haga and Gabriel Berstein, 1st ed., pp. 265-280 CRC Press—Boca Raton Fla.; September 1999.

Genetically engineered yeast systems and insect cell systems which lack endogenous GPCRs provide the advantage of a null background for CSR::T1R activation screening.

Genetically engineered yeast systems substitute a human GPCR and Gα protein for the corresponding components of the endogenous yeast pheromone receptor pathway. Downstream signaling pathways are also modified so that the normal yeast response to the signal is converted to positive growth on selective media or to reporter gene expression (described by Broach, J. R. and J. Thorner (1996) Nature 384 (supp.):14-16).

Genetically engineered insect systems incorporate a human GPCR and Gα protein that enables receptor coupling the phospholipase C signaling pathway (see for example Knight and Grigliatti, (2004) J Receptors and Signal Transduction 24: 241-256).

Amphibian cell systems, in particular melanophore cells, are described, for example, in WO 92/01810 that describes a GPCR expression system.

Overexpression of CSR::T1R:

CSR::T1R may be overexpressed by placing it under the control of a strong constitutive promoter, for example the CMV early promoter. Alternatively, certain mutations of conserved GPCR amino acids or amino acid domains can be introduced to render the employed GPCR constitutively active.

Transfection of CSR::T1R Expression Vector Constructs into Cells:

Standard transfection methods can be used to produce bacterial, mammalian, yeast or insect cell lines that express large quantities of the protein.

Any known method for introducing nucleotide sequences into host cells may be used. It is only necessary that the particular genetic engineering procedure used be capable of successfully introducing the relevant genes into the host cell capable of expressing the proteins of interest. These methods may involve introducing cloned genomic DNA, cDNA, synthetic DNA or other foreign genetic material into a host cell and include the use of calcium phosphate transfection, polybrene, protoplast fusion, electroporation, liposomes, microinjection, plasma vectors, viral vectors and the like.

For example, without limitation, the T-Rex™ expression system (Invitrogen Corp., Carlsbad, Calif.) may be used. The T-Rex™ System is a tetracycline-regulated mammalian expression system that uses regulatory elements from the *E. coli* Tn10-encoded tetracycline (Tet) resistance operon. Tetracycline regulation in the T-Rex™ System is based on the binding of tetracycline to the Tet repressor and derepression of the promoter controlling expression of the gene of interest.

Cell Culture:

After transfection, the transfected cells may be cultured using standard culturing conditions well known in the art. It will be apparent to the skilled person that different cells require different culture conditions including appropriate temperature and cell culture media.

CSR::T1R Receptor Protein Recovery:

If desired, the protein may be recovered from the cell culture using standard techniques. For example, the cells may be burst open either mechanically or by osmotic shock before being subject to precipitation and chromatography steps, the nature and sequence of which will depend on the particular recombinant material to be recovered. Alternatively, the recombinant protein may be recovered from the culture medium in which the recombinant cells had been cultured.

Modulators that may be Identified by the Assays:

Modulators (various types including ligands, agonists, partial agonists, antagonists, inverse agonists, inhibitors, enhancers) of CSR::T1R receptor activity can be identified as described herein below.

The type of a modulator may include more than one type at a time, and may depend on the concentration. For example, an agent may act as an agonist in a certain concentration range, but act as a modulator or enhancer of another agonist (for example a sweetener or sugar) in another concentration range. Therefore, agents should be tested at different concentrations to identify them as modulators.

There now follows a definition of the agents to be identified in the methods described herein.

A modulator is an agent that effects an increase or decrease of one or more of the following: the cell surface expression of a receptor, the binding of a ligand to a receptor, the intracellular response initiated by an active form of the receptor (either in the presence or absence or an agonist). The modulator can itself be an agonist that binds to the receptor, activates it and thereby modulates an increase in the cellular response.

Modulators include various types of compounds, including small molecules, peptides, proteins, nucleic acids, antibodies or fragments thereof. These can be derived from various sources including synthetic or natural, extracts of natural material, for example from animal, mammalian, insect, plant, bacterial or fungal cell material or cultured cells, or conditioned medium of such cells.

A ligand is an agent that binds to the receptor; it may be an agonist, partial agonist, enhancer, antagonist, or inverse agonist.

An agonist is a ligand of the CSR::T1R chimeric protein receptor that activates the receptor and increases an intracellular response when it binds to a receptor compared to the intracellular response in the absence of the agonist. Additionally or alternatively, an agonist may decrease internalization of a cell surface receptor such that the cell surface expression of a receptor is increased as compared to the number of cell surface receptors present on the surface of a cell in the absence of an agonist.

Agonists of CSR::T1R include, for example, calcium, perillartine, cyclamate, NDHC, and cinnamonitrile.

A ligand of the CSR::T1R chimeric protein can be divided into two types, a CSR-domain-ligand which binds in the CSR part of the chimeric protein (calcium), or a TSR-domain ligand, which binds in the T1R-part of the chimeric protein (modulators of the sweet taste response).

A partial agonist is an agonist that only partially activates the receptor in comparison to other agonists that maximally activate the receptor.

An antagonist is a ligand which binds to the receptor at the same (competitive antagonist) or at a different site (alllosteric antagonist) as an agonist, but does not activate an intracellular response initiated by an active form of a receptor, thereby inhibiting the intracellular response induced by an agonist as compared to the intracellular response in the presence of an agonist and in the absence of an antagonist.

An inverse agonist, binding to a receptor, decreases the constitutive intracellular response mediated by a receptor as compared to the intracellular response in the absence of the inverse agonist.

An inhibitor decreases the binding of an agonist to the receptor as compared to the binding of the agonist in the absence of inhibitor, and/or decreases the intracellular response induced by an agonist.

An enhancer increases the binding of an agonist to the receptor as compared to the binding of the agonist in the absence of enhancer, and/or increases the intracellular response induced by an agonist.

The activity, or changes in activity, of a receptor binding a ligand and transmitting the signal through, for example, a G-protein (i.e. due to different interactions with modulators) can be determined by the assays described herein-below.

Assays to Identify Modulators of the CSR::T1R Receptor:

Modulators can be identified using a wide variety of in vitro and in vivo assays to determine and compare functional effects/parameters, or alternatively by binding assays. The effects of the test agents upon the function of the receptors can be measured by examining a suitable functional parameters. Any physiological change that affects receptor activity can be used to identify modulators.

Such functional assays are well-known in the art, for example assays using intact cells or tissues isolated from animals based on measuring the concentration or activity or their change of a secondary messenger (including, for example, intracellular calcium (Ca2+), cAMP, cGMP, inositol phosphate (IP3), diacylglycerol/DAG, arachinoid acid, MAP kinase or tyrosine kinase), ion flux, phosphorylation levels, transcription levels, neurotransmitter levels, and assays based on GTP-binding, GTPase, adenylate cyclase, phospholipid-breakdown, diacylglycerol, inositol triphosphate, arachidonic acid release, PKC, kinase and transcriptional reporters. Some suitable assays are, for example, described in WO 01 18050.

Receptor activation typically initiates subsequent intracellular events, for example, increases in second messengers, for example, IP3, which releases intracellular stores of calcium ions. Activation of some G-protein coupled receptors stimulates the formation of inositol triphosphate (IP3) through phospholipase C-mediated hydrolysis of phosphatidylinositol. IP3 in turn stimulates the release of intracellular calcium ion stores. Thus, a change in cytoplasmic calcium ion levels, or a change in second messenger levels such as IP3 can be used to determine G-protein coupled receptor activity.

All functional assays may be performed by samples containing cells expressing the receptor on their surfaces or on isolated cell membrane fractions. Useful cells are described herein-above. Instead of samples with separate cells or cell membranes, tissues from transgenic animals may be used.

The screening methods described herein are particularly useful to identify modulators of the sweet taste response, for example, sweetness enhancers.

To identify a modulator which is not an agonist itself (e.g. an antagonist, partial agonist, inverse agonist, inhibitor, or enhancer), samples with and without test agent both containing an agonist are compared. As agonist, for example, calcium can be used. Using calcium has the advantage that both TMDs will be accessible. Other known or identified agonists can also be used, for example, perillartine, cyclamate, neohesperidine dihydrochalone (NDHC), and cinnamonitrile), but will partially occupy ligand/agonist binding sites which may coincide with the modulator binding site of the to be identified modulator, and may cause lower signals. For example, a control (with agonist but without modulator) is assigned a relative receptor activity value of 100. A decrease in activity relative to the control identifies an inhibitor, antagonist or inverse agonist, an increase identifies an enhancer. Usually, an increase or decrease in the measured activity of 10% or more in a sample with test agent compared to a sample without test agent or compared to a sample with test agent but based on cells that do not express CSR::T1R (mock-transfected cells) can be considered significant.

To identify a sweetness enhancer, samples with and without test agent are compared. For example, a control (with agonist, for example calcium chloride, but without modulator) is assigned a relative receptor activity value of 100. An increase identifies an enhancer. Usually, an increase or decrease in the measured activity of 10% or more in a sample with test agent compared to a sample without test agent or compared to a sample with test agent but based on cells that do not express CSR::T1R (mock-transfected cells) can be considered significant.

For screens that employ the CSR::TSR1 chimeric protein, calcium can be used as agonist. Alternatively, agonists binding in the relevant parts of the T1R2 and/or T1R3 fragments of CSR::TSR1 may be used. These agonists include, for example, perillartine, cyclamate, NDHC, and cinnamonitrile.

Identification of Agonists or Partial Agonists:

To identify an agonist or partial agonist that does not bind in the VFT domains, a sample with test agent is compared to a positive control with an agonist (for example calcium chloride, perillartine, cyclamate, neohesperidin dihydrochalcone (NDHC), cinnamonitrile, or another identified ligand/agonist).

Alternatively/additionally, samples with and without test agent are compared in their activity of the CSR::T1R chimeric protein.

For example, an agonist or partial agonist will have a biological activity corresponding to at least 10% of the maximal biological activity of the positive control sweet agonist when the agonist or partial agonist is present at 100 mM or less, for example it may have a maximal biological activity comparable to the agonist or higher. Maximal biological activity is defined as the maximal achievable receptor response to an agonist, for example calcium chloride, perillartine, cyclamate, neohesperidin dihydrochalcone (NDHC), cinnamonitrile that can be achieved within a given receptor assay format and this response fails to increase further despite application of increasing concentrations of that same agonist.

The above-mentioned agonists may, at a different concentration, also act as an enhancer of an agonist of the CSR::T1R chimeric protein. This may be tested in a screening method by using calcium or other agonist to test the agonist-test agent for signals indicating a sweetness enhancing effect.

Alternatively, an increase in the measured activity of, for example, 10% or more in a sample with test agent is compared to a sample without test agent or is compared to a sample with test agent but based on cells that do not express CSR::T1R (mock-transfected cells).

To identify antagonists, receptor activity in the presence of a known agonist with and without a test agent is compared.

Antagonists show a reduction of agonist-stimulated receptor activity, for example by at least 10%.

To identify inverse agonists, receptor activity in the presence of a known agonist with and without a test agent is compared in samples comprising animals/cells/membranes that overexpress the receptor as described herein-above. Inverse agonists show a reduction of constitutive activity of the receptor, for example by at least 10%.

Various examples of suitable detection methods that measure CSR::T1R receptor activity in assays described herein-above follow.

Many screens rely on calcium activity, and for these a buffer system low in calcium should be used to avoid unspecific stimulation of cells, receptor, enzyme or reporter genes)

Detection of changes of cytoplasmic ions or membrane voltage:

Cells are loaded with ion sensitive dyes to report receptor activity, as described in detail in "G-protein coupled receptors (Signal Transduction Series)", CRC Press 1999; 1st Edition; Eds Haga and Berstein. Changes in the concentration of ions in the cytoplasm or membrane voltage are measured using an ion sensitive or membrane voltage fluorescent indicator, respectively.

Calcium Flux:

Intracellular calcium release induced by the activation of GPCRs is detected using cell-permeant dyes that bind to calcium. The calcium-bound dyes generate a fluorescence signal that is proportional to the rise in intracellular calcium. The methods allows for rapid and quantitative measurement of receptor activity.

Cells used are transfected cells that co-express the CSR::T1R GPCR and a G-protein which allows for coupling to the phospholipase C pathway as described herein-above Negative controls include cells or their membranes not expressing CSR::T1R (mock transfected), to exclude possible non-specific effects of the candidate compound.

The calcium flux detection protocol is described in detail in "G-protein coupled receptors (Signal Transduction Series)"; Editors: Tatsuya Haga and Gabriel Berstein, 1st ed., 424 pp. CRC Press—Boca Raton Fla.; September 1999, and an adapted version with is summarised below:

Day 0: 96-well plates are seeded with 8.5K cells per well and maintained at 37° C. overnight in nutritive growth media.

Day 1: Cells are transfected using 150 ng of GPCR DNA and 0.3 µl of Lipofectamine 2000 (Invitrogen) per well. Transfected cells are maintained at 37° C. overnight in nutritive growth media.

Day 2: Growth media is discarded and cells are incubated for 1 hour (at room temperature in the dark) with 50 µl of calcium assay solution consisting of 1.5 µM Fluo-4 AM (Molecular Probes) and 2.5 µM probenicid dissolved in a reduced calcium C1 buffer solution which contains 130 mM NaCl, 5 mM KCl, 10 mM Hepes, 0.5 mM CaCl2 and 10 mM glucose (pH 7.4) at 37° C. 125 µl of the reduced calcium C1 buffer is added to each well and the plate is further incubated for 30 minutes at room temperature in the dark.

Buffer solutions are discarded and plate is washed 5 times with 100 µl reduced calcium C1 buffer as a washing buffer and cells are reconstituted in 200 µl of reduced calcium C1 buffer.

Then the plate is placed in a fluorescent microplate reader, for example, the Flexstation (Molecular Devices) or the FLIPR (Molecular Devices) and receptor activation is initiated following addition of 20 µl of a 10× concentrated ligand stock solution. Fluorescence is continuously monitored for 15 seconds prior to ligand addition and for 45-110 seconds after ligand addition. Receptor activation levels are defined by the two following equations: % Activation=(Maximum fluorescence−baseline fluorescence/baseline fluorescence)*100 or Fluorescence Increase=Maximum Fluorescence−baseline fluorescence, where baseline fluorescence represents the average fluorescence levels prior to ligand addition.

Useful cells are, without limitation, mammalian cells as described herein-above, for example HEK293T cells and HEK293 T-Rex™ cells. Cells may be transfected with a GPCR and a G-Protein transiently or stably as is well known in the art. An excellent heterologous expression system is described in detail in WO 2004/055048.

A calcium flux assay can be performed, for example, as described in example 1 herein-below.

The identification of a modulator is performed as described above subject to the following modifications. The signals are compared to the baseline level of CSR::T1R activity obtained from recombinant cells expressing CSR::T1R in the presence of an agonist but in the absence of a test agent. An increase or decrease in CSR::T1R activity, for example of at least 2 fold, at least 5 fold, at least 10 fold, at least a 100 fold, or more identifies a modulator.

Alternatively, the identification involves an increase or decrease fluorescence intensity of, for example, 10% or more, when compared to a sample without modulator, or when compared to a sample with modulator but in cells that do not express the CSR::T1R polypeptide (mock-transfected cells).

Adenylate Cyclase Activity:

Assays for adenylate cyclase activity are performed, for example, as described in detail by Kenimer & Nirenberg, 1981, Mol. Pharmacol. 20: 585-591. Reaction mixtures are incubated usually at 37° C. for less than 10 minutes. Following incubation, reaction mixtures are deproteinized by the addition of 0.9 ml of cold 6% trichloroacetic acid. Tubes are centrifuged and each supernatant solution is added to a Dowex AG50W-X4 column. The cAMP fraction from the column is eluted with 4 ml of 0.1 mM imidazole-HCl (pH 7.5) into a counting vial in order to measure the levels of cAMP generated following receptor activation by the agonist. Control reactions should also be performed using protein homogenate from cells that do not express a CSR::T1R polypeptide.

IP3/$Ca^{2+}$ Signals:

In cells expressing G-proteins, signals corresponding to inositol triphosphate (IP3)/$Ca^{2+}$ and thereby receptor activity can be detected using fluorescence. Cells expressing a GPCR may exhibit increased cytoplasmic calcium levels as a result of contribution from both intracellular stores and via activation of ion channels, in which case it may be desirable, although not necessary, to conduct such assays in calcium-free buffer, optionally supplemented with a chelating agent such as EDTA, to distinguish fluorescence response resulting from calcium release from internal stores.

Phospholipase C/Intracellular $Ca^{2+}$ Signals:

CSR::T1R is expressed in a cell with a G-protein that links the receptor to a phospholipase C signal transduction pathway. Changes in intracellular $Ca^{2+}$ concentration are measured, for example using fluorescent $Ca^{2+}$ indicator dyes and/or fluorometric imaging.

GTPase/GTP Binding:

For a GPCR including CSR::T1R, a measure of receptor activity is the binding of GTP by cell membranes containing the GPCR. Measured is the G-protein coupling to membranes by detecting the binding of labelled GTP.

Membranes isolated from cells expressing the receptor are incubated in a buffer containing 35S-GTPγS and unlabelled GDP. Active GTPase releases the label as inorganic phosphate, which is detected by separation of free inorganic phosphate in a 5% suspension of activated charcoal in 20 mM $H_3PO_4$, followed by scintillation counting. The mixture is incubated and unbound labelled GTP is removed by filtration onto GF/B filters. Bound and labelled GTP is measured by liquid scintillation counting. Controls include assays using membranes isolated from cells not expressing CSR::T1R (mock-transfected), in order to exclude possible non-specific effects of the test agent. The method is described in detail by Traynor and Nahorski, 1995, Mol. Pharmacol. 47: 848-854.

To identify modulators, as described herein-above, a change (increase or decrease) of 10% or more in GTP binding or GTPase activity is usually sufficient. However, to identify agonists, the assays described herein-above are performed subject to the following modifications. An agent is identified as an agonist usually if the activity is at least 50% of that of a known agonist (for example perillartine) when the compound is present at 100 mM or less, for example 10 to 500 µM, for example about 100 µM, or if it will induce a level the same as or higher than that induced by a known agonist.

Microphysiometer or Biosensor:

Such assays can be performed as described in detail in Hafner, 2000, Biosens. Bioelectron. 15: 149-158.

Arachinoid Acid:

The intracellular level of arachinoid acid is employed as an indicator of receptor activity. Such a method is described in detail by Gijon et al., 2000, J. Biol. Chem., 275:20146-20156.

cAMP/cGMP:

Intracellular or extracellular cAMP is measured using a cAMP radioimmunoassay (RIA) or cAMP binding protein, for example as described by Horton & Baxendale, 1995, Methods Mol. Biol. 41: 91-105. Alternatively, a number of kits for the measurement of cAMP are commercially available, for example the High Efficiency Fluorescence Polarization-based homogeneous assay by LJL Biosystems and NEN Life Science Products. Alternatively, the intracellular or extracellular levels of cGMP may measured using an immunoassay. For example, the method described in Felley-Bosco et al., Am. J. Resp. Cell and Mol. Biol., 11:159-164 (1994), may be used to determine the level of cGMP. Alternatively an assay kit for measuring cAMP and/or cGMP as described in U.S. Pat. No. 4,115,538 can be used.

Negative controls with mock-transfected cells or extracts thereof to exclude possible non-specific effects of test agents may be used.

DAG/IP3:

Second messengers Diacylglycerol (DAG) and/or inositol triphosphate (IP3), which are released by Phospholipid breakdown, that is caused by receptor activity, can be detected and used as an indicator of GPCR (CSR::T1R) activity, for example as described in Phospholipid Signalling Protocols, edited by Ian M. Bird, Totowa, N.J., Humana Press, 1998. Alternatively, kits for the measurement of inositol triphosphates are available commercially from Perkin Elmer and CisBio International.

Negative controls with mock-transfected cells or extracts thereof to exclude possible non-specific effects of test agents may be used.

PKC Activity:

Growth factor receptor tyrosine kinases can signal via a pathway involving activation of Protein Kinase C(PKC), which is a family of phospholipid- and calcium-activated protein kinases.

Increases in gene products induced by PKC show PKC activation and thereby receptor activity. These gene products include, for example, proto-oncogene transcription factor-encoding genes (including c-fos, c-myc and c-jun), proteases, protease inhibitors (including collagenase type I and plasminogen activator inhibitor), and adhesion molecules (including intracellular adhesion molecule I (ICAM I)).

PKC activity may be directly measured as described by Kikkawa et al., 1982, J. Biol. Chem. 257: 13341, where the phosphorylation of a PKC substrate peptide, which is subsequently separated by binding to phosphocellulose paper, is measured. It can be used to measure activity of purified kinase, or in crude cellular extracts. Protein kinase C sample can be diluted in 20 mM HEPES/2 mM DTT immediately prior to the assay.

An alternative assay can be performed using the Protein Kinase C Assay Kit commercially available by PanVera.

The above-described PKC assays are performed on extracts from cells expressing the GPCR (CSR::T1R).

Alternatively, activity can be measured through the use of reporter gene constructs driven by the control sequences of genes activated by PKC activation.

Negative controls with mock-transfected cells or extracts thereof to exclude possible non-specific effects of test agents may be used.

Map Kinase Activity:

MAP kinase activity can be measured using commercially available kits, for example, the p38 MAP Kinase assay kit by New England Biolabs, or the FlashPlate™ MAP Kinase assays by Perkin-Elmer Life Sciences. p42/44 MAP kinases or ERK1/2 can be measured to show GPCR (CSR::T1R) activity when cells with Gq and Gi coupled GPCRs are used, and an ERK1/2 assay kit is commercially available by TGR Biosciences, which measures the phosphorylation of endogenous ERK1/2 kinases following GPCR activation.

Alternatively, direct measurements of tyrosine kinase activity through known synthetic or natural tyrosine kinase substrates and labelled phosphate are well known; the activity of other types of kinases (for example, Serine/Threonine kinases) can be measured similarly.

All kinase assays can be performed with both purified kinases and crude extracts prepared from cells expressing one or more CSR::T1R polypeptide.

The substrates of kinases that are used can be either full-length protein or synthetic peptides representing the substrate. Pinna & Ruzzene (1996, Biochem. Biophys. Acta 1314: 191-225) lists a number of phosphorylation substrate sites useful for detecting kinase activities. A number of kinase substrate peptides are commercially available. One that is particularly useful is the "Src-related peptide," RRLIEDAEYAARG (commercially available from Sigma), which is a substrate for many receptor and nonreceptor tyrosine kinases. Some methods require the binding of peptide substrates to filters, then the peptide substrates should have a net positive charge to facilitate binding. Generally, peptide substrates should have at least 2 basic residues and a free-amino terminus. Reactions generally use a peptide concentration of 0.7-1.5 mM.

Negative controls with mock-transfected cells or extracts thereof to exclude possible non-specific effects of test agents may be used.

Transcriptional Reporters/CSR::T1R-Responsive Promoter/Reporter Gene:

To identify modulators with reporter gene assays, an at least 2-fold increase or 10% decrease in the signal is significant. An agonist stimulates for example at least 2-fold, 5-fold, 10-fold or more when comparing activity in presence and absence of the test agent.

The intracellular signal initiated by binding of an agonist to CSR::T1R sets in motion a cascade of intracellular events, the ultimate consequence of which is a rapid and detectable change in the transcription or translation of one or more genes.

The activity of the receptor can therefore be determined by measuring the expression of a reporter gene driven by a promoter responsive to CSR::T1R activation.

A "promoter" as used herein is one or more transcriptional control elements or sequences necessary for receptor-mediated regulation of gene expression, including one or more of basal promoter, enhancers and transcription-factor binding sites necessary for receptor-regulated expression. Promoters responsive to the intracellular signals resulting from agonist binding to CSR::T1R are selected and operatively linked to a corresponding promoter-controlled reporter gene whose transcription, translation or ultimate activity is readily detectable and measurable.

Reporter genes may be selected, for example, from luciferase, CAT, GFP, α-lactamase, β-galactosidase, and the so-called "immediate early" genes, c-fos proto-oncogene, transcription factor CREB, vasoactive intestinal peptide (VIP) gene, the somatostatin gene, the proenkephalin gene, the phosphoenolpyruvate carboxy-kinase (PEPCK) gene, genes responsive to NF-κB, and AP-1-responsive genes (including the genes for Fos and Jun, Fos-related antigens (Fra) 1 and 2, IκBα, ornithine decarboxylase, and annexins I and II).

Promoters will be selected according to the selected reporter gene, as will be apparent to the skilled person.

Luciferase, CAT, GFP, β-lactamase, β-galactosidase and assays for the detection of their products are well known in the art. Examples of further reporter genes are described herein-below.

The "immediate early" genes are suitable and are rapidly induced (for example within minutes of contact between the receptor and the effector protein or ligand). Desirable properties in reporter genes include one or more of the following: rapid responsiveness to ligand binding, low or undetectable expression in quiescent cells; induction that is transient and independent of new protein synthesis; subsequent shut-off of transcription requires new protein synthesis; and mRNAs transcribed from these genes which have a short half-life of several minutes to a few hours. Similarly, the promoter may have one, several or all of these properties.

The c-fos proto-oncogene is an example of a gene that is responsive to a number of different stimuli and has an rapid induction. The c-fos regulatory elements include a TATA box that is required for transcription initiation; two upstream elements for basal transcription, and an enhancer, which includes an element with dyad symmetry and which is required for induction by TPA, serum, EGF, and PMA. The 20 bp c-fos transcriptional enhancer element located between −317 and -298 bp upstream from the c-fos mRNA cap site, is essential for serum induction in serum starved NIH 3T3 cells. One of the two upstream elements is located at −63 to −57 and it resembles the consensus sequence for cAMP regulation.

The transcription factor CREB (cyclic AMP responsive element binding protein) is responsive to levels of intracellular cAMP. Therefore, the activation of a receptor that signals via modulation of cAMP levels can be determined by detecting either the binding of the transcription factor, or the expression of a reporter gene linked to a CREB-binding element (termed the CRE, or cAMP response element). The DNA sequence of the CRE is TGACGTCA. Reporter constructs responsive to CREB binding activity are described in U.S. Pat. No. 5,919,649.

Other suitable reporter genes and their promoters include the vasoactive intestinal peptide (VIP) gene and its promoter which is cAMP responsive; the somatostatin gene and its promoter which is cAMP responsive; the proenkephalin and its promoter which is responsive to cAMP, nicotinic agonists, and phorbol esters; and the phosphoenolpyruvate carboxy-kinase (PEPCK) gene and its promoter which is cAMP responsive.

Additional examples of reporter genes and their promoters that are responsive to changes in GPCR activity include the AP-1 transcription factor and NF-κB. The AP-1 promoter is characterised by a consensus AP-1 binding site which is the palindrome TGA(C/G)TCA. The AP-1 site is also responsible for mediating induction by tumor promoters including the phorbol ester 12-O-tetradecanoylphorbol-β-acetate (TPA), and are therefore sometimes also referred to as a TRE, for TPA-response element. AP-1 activates numerous genes that are involved in the early response of cells to growth stimuli. Examples of AP-1-responsive genes include the genes for Fos and Jun (which proteins themselves make up AP-1 activity), Fos-related antigens (Fra) 1 and 2, IκBα, ornithine decarboxylase, and annexins I and II.

A large number of genes have been identified as NF-κB responsive, and their control elements can be linked to a reporter gene to monitor GPCR activity. Genes responsive to NF-κB include for example those encoding IL-1β, TNF-α, CCR5, P-selection, Fas ligand, GM-CSF and IκBα. Vectors encoding NF-κB-responsive reporters are known in the art or can be readily formed using ordinary skill in the art, for example, synthetic NF-κB elements and a minimal promoter, or using the NF-κB-responsive sequences of a gene known to be subject to NF-κB regulation. Further, NF-κB responsive reporter constructs are commercially available from, for example, CLONTECH.

A given promoter construct can easily be tested by exposing GPCR (CSR::T1R)-expressing cells, transfected with the construct, to an agonist (for example perillartine). An increase of at least 2-fold in the expression of reporter gene in response to the agonist indicates that the reporter is suitable to measure GPCR (CSR::T1R) activity.

Controls for transcription assays include both cells not expressing GPCR (CSR::T1R), but carrying the reporter construct, and cells with a promoterless reporter construct.

Agents that modulate GPCR (CSR::T1R) activity as shown by reporter gene activation can be verified by using other promoters and/or other receptors to verify GPCR (CSR::T1R) specificity of the signal and determine the spectrum of their activity, thereby excluding any non-specific signals, for example non-specific signals via the reporter gene pathway.

Inositol Phosphates (IP) Measurement:

Phosphatidyl inositol (PI) hydrolysis may be determined as described in U.S. Pat. No. 5,436,128, which involves labelling of cells with 3H-myoinositol for at least 48 hours or more. The labelled cells are contacted with a test agent for one hour, then these cells are lysed and extracted in chloroform-methanol-water. This is followed by separating the inositol phosphates by ion exchange chromatography and quantifying them by scintillation counting. For agonists, fold stimulation is determined by calculating the ratio of counts per minute (cpm) in the presence of tested agent, to cpm in the presence of buffer control. Likewise, for inhibitors, antagonists and inverse agonists, fold inhibition is determined by calculating the ratio of cpm in the presence of test agent, to cpm in the presence of buffer control (which may or may not contain an agonist).

Binding Assays:

Alternatively to the functional assays described hereinabove that measure a change in parameters caused by a functional response to ligand binding, ligand binding may be determined by binding assays that measure the binding of a ligand to a CSR::T1R receptor.

Binding assays are well known in the art and can be tested in solution, in a bilayer membrane, optionally attached to a solid phase, in a lipid monolayer, or in vesicles. Binding of a modulator to a CSR::T1R polypeptide can be determined, for example, by measuring changes in spectroscopic characteristics (for example fluorescence, absorbance, or refractive index), hydrodynamic methods (employing for example shape), chromatography, measuring solubility properties of a CSR::T1R polypeptide. In one embodiment, binding assays are biochemical and use membrane extracts from cells/tissue expressing recombinant CSR::T1R polypeptides. A binding assay may, for example, be performed as described for T1R5 by Adler et al. in US20050032158, paragraphs [0169] to [0198].

CSR::T1R Receptor Polypeptide and Nucleic Acid, and Substantially Homologous Polypeptides and Nucleic Acids:

The CSR::T1R chimeric protein useful in methods described herein may be selected from the group consisting of the polypeptide selected from SEQ ID NO:2 (CSR::T1R2-a), SEQ ID NO:4 (CSR::T1R3-a), SEQ ID NO: 20 (CSR::T1R2-b), SEQ ID NO: 22 (CSR::T1R3-b), the chimeric heterodimer of SEQ ID NO: 2 and SEQ ID NO:4 (CSR::T1R2-a/CSR::T1R3-a), the chimeric heterodimer of SEQ ID NO: 20 and SEQ ID NO: 22 (CSR::T1R2-b/CSR::T1R3-b), the chimeric heterodimer of SEQ ID NO: 2 and SEQ ID NO: 22 (CSR::T1R2-a/CSR::T1R3-b), the chimeric heterodimer of SEQ ID NO: 20 and SEQ ID NO: 4 (CSR::T1R2-b/CSR::T1R3-a), a heterodimer of SEQ ID NO:2 or 20 with wildtype T1R3 (CSR::T1R2-a/T1R3 or CSR::T1R2-b/T1R3), a heterodimer of SEQ ID NO: 4 or 22 with wildtype T1R2 (T1R2/CSR::T1R3-a or T1R2/CSR::T1R3-b).

Alternatively, the CSR::T1R chimeric protein (or nucleic acid encoding the CSR::T1R) may be a receptor (or nucleotide sequence to form such a CSR::T1R receptor) which is substantially homologous and remains functional (i.e. binds to ligands and/or is activated by ligands, or encodes such a receptor).

A substantially homologous CSR::T1R chimeric protein includes such proteins where the T1R2 or T1R3 part of CSR::T1R2 and/or CSR::T1R3 is replaced with the relevant part of an allelic variant or different species, including T1R2 and/or T1R3 from mouse, rat, hamster, ape, and dog.

Further, substantially homologous CSR::T1R nucleotide or polypeptide sequences may be formed by conservative mutations and/or point mutations and include any conservatively modified variant as detailed below.

With respect to nucleic acid sequences, conservatively modified variants means nucleic acids which encode identical or essentially identical amino acid sequences (conservatively substituted amino acids, i.e. lysine switched to arginine and further examples as explained herein-below).

Because of the degeneracy of the genetic code, a large number of nucleic acids different in sequence but functionally identical encode any given polypeptide/protein. Such nucleic acid variations are "silent variations," which are one species of conservatively modified variations. Each nucleic acid sequence which encodes a polypeptide also describes every possible silent variation of the nucleic acid. Therefore, each codon in a nucleic acid (except AUG, which is ordinarily the only codon for methionine, and TGG, which is ordinarily the only codon for tryptophan) can be modified to yield a functionally identical nucleic acid sequence that will produce an identical polypeptide. Accordingly, each silent variation of a nucleic acid which encodes a polypeptide is implicit in each given nucleic acid sequence.

With respect to amino acid sequences, amino acid substitutions may be introduced using known protocols of recombinant gene technology including PCR, gene cloning, site-directed mutagenesis of cDNA, transfection of host cells, and in-vitro transcription which may be used to introduce such changes to the CSR::T1R sequence. The variants can then be screened for taste-cell-specific GPCR functional activity. Conservative substitution tables providing functionally similar amino acids are well known in the art. For example, one exemplary guideline to select conservative substitutions includes (original residue followed by exemplary substitution): ala/gly or ser; arg/lys; asn/gln or his; asp/glu; cys/ser; gin/asn; gly/asp; gly/ala or pro; his/asn or gin; ile/leu or val; leu/ile or val; lys/arg or gin or glu; met/leu or tyr or ile; phe/met or leu or tyr; ser/thr; thr/ser; trp/tyr; tyr/trp or phe; val/ile or leu.

An alternative exemplary guideline uses the following six groups, each containing amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (1); 5) Isoleucine (I), Leucine (L), Methionine (M), Valine (V); and 6) Phenylalanine (F), Tyrosine (Y), Tryptophan (W).

Another alternative guideline is to allow for all charged amino acids as conservative substitutions for each other whether they are positive or negative.

In addition, individual substitutions, deletions or additions that alter, add or delete a single amino acid or a small percentage (for example up to 26%, or up to 20%, or up to 10%) of amino acids in an encoded sequence are also considered to be conservatively modified variations.

Substantially homologous nucleotide or polypeptide sequences have the degree of sequence identity or hybridize under certain stringent hybridization conditions as indicated below.

% Sequence Identity:

A substantially homologous nucleotide sequence has a % sequence identity of at least at least 90%, at least 95%, or at least 98%.

A substantially homologous polypeptide sequence has a % sequence identity of at least at least 90%, at least 95% or at least 98%.

Calculation of % Sequence Identity is determined as follows.

BLAST (Basic Local Alignment Search Tool) is the heuristic search algorithm employed by the programs blastn which is available at the interne website of the National Center For Biotechnology Information.

To determine % identity of a nucleotide query sequence against another nucleotide sequence, Blastn is used, using default parameters of BLAST version 2.2.1.3, including an EXPECT (statistical significance threshold for reporting matches against database sequences) of 10, and DUST filtering.

Stringent Hybridization Conditions:

Nucleotide sequences are considered substantially homologous provided that they are capable of selectively hybridizing to the nucleotide sequences presented herein, or to their complement, under stringent hybridisation conditions detailed below. Stringent conditions are temperature of 42° C. in a solution consisting of 50% formamide, 5×SSC, and 1% SDS and washing at 65° C. in a solution consisting of 0.2× SSC and 0.1% SDS (1×SSC=0.15 M NaCl, 0.015 M $Na_3$ Citrate pH 7.0).

Background hybridization may occur because of other nucleotide sequences present, for example, in the cDNA or genomic DNA library being screened.

A signal that is less than 10 fold as intense as the specific interaction observed with the target DNA is considered background. The intensity of interaction may be measured, for example, by radiolabelling the probe, e.g. with $^{32}P$.

Kit to Identify a Modulator:

A kit, for example, a screening kit or high throughput screening kit, that comprises recombinant cells that express the CSR::T1R, or a substantially homologous sequence thereto; and that comprises an agonist of the CSR::T1R, for example, without limitation, calcium chloride, perillartine, NDHC, cyclamate, and cinnamonitrile.

Using a kit comprising calcium has the advantage of binding to and activating the chimeric protein only, but not the wild-type receptor or the T1R2 and T1R3 part of the chimeric protein.

Optionally, the cells further comprise a G-protein for example for calcium signalling. Suitable G-proteins are known and described herein-above; the skilled person is aware how to introduce them to the cells if necessary. A very useful chimeric G-protein is Galpha16-gustducin 44.

The agonist is provided in suitable concentrations, for example 1 nM to 10 mM, or 0.1 microM to 1 milliM, for example 0.1 microM to 100 microM.

Useful concentrations are, for example, for calcium chloride 0.2 to 20 mM, for perillartine 5 to 500 µM, for cinnamonitrile 10 to 1000 µM, for cyclamate 0.01 to 5 mM, for Neohesperidin Dihydrochalcone (NDHC) 0.033 to 3.3 mM.

Optional kit components may include a suitable medium for culturing the recombinant cells provided, and a solid support to grow the cells on, for example, a cell culture dish or microtiter plate, these optional components will be readily available to the skilled person.

The kit may be used as follows:
(i) Recombinant cells that express the CSR::T1R chimeric protein are grown on the solid support.
(ii) test agents at concentrations from about 1 nM to 100 mM or more are added to the culture medium of defined plates or wells in the presence of the agonist in a suitable concentration
(iii) a change in a functional response of the cells is determined by comparing the response in presence and absence of the test agent, and the test agent is thereby identified as a modulator.

For example, (iii) may be performed according to any one of the assays described-herein above, in combination with any one of the detection methods that report receptor activity described herein-above. This may require specifically chosen or adapted recombinant cells, which are also described herein-above.

A suitable assay is, for example, the calcium flux assay to determine activation of CSR::T1R and its change in response to a test agent.

The kit may be used to identify an enhancer as follows:
(i) Recombinant cells that express the CSR::T1R chimeric protein are grown on the solid support.
(ii) rest agents at concentrations from about 1 nM to 100 mM or more are added to the culture medium of defined plates or wells in the presence of the calcium agonist (for example, without limitation, in form of calcium chloride) in a suitable concentration.
(iii) a change in a functional response of the cells to calcium is determined by comparing the response in presence and absence of the test agent, and the test agent is thereby identified as an enhancer.

A suitable calcium chloride concentration is, for example, from about 0.2 to 20 mM, or 0.5 to 10 mM, or about 1 mM.

Confirmation of Identified Modulators:

A modulator identified by a method described hereinabove may easily be confirmed by simple sensory experiments using a panel of flavorists or test persons to taste the identified modulators. The compounds are tasted e.g. in water to confirm sweet taste or together with sweet tastants in comparison to a negative control without modulator to confirm a modulator that enhances the sweet taste.

Large Scale Screening Assays:

Transcriptional reporter assays and most cell-based assays described herein-above are well suited for screening libraries for agents that modulate CSR::T1R activity.

The assays may be designed to screen large chemical libraries by automating the assay steps and providing compounds from any convenient source to the assays, which are typically run in parallel (for example in microtiter formats on microtiter plates in robotic assays).

Assays may be run in high throughput screening methods that involve providing a combinatorial chemical or peptide library containing a large number of potential modulators. Such libraries are then screened in one or more assays described herein-above to identify those library agents (particular chemical species or subclasses) that display the activity described herein-above. The modulators thus identified can be directly used or may serve as leads to identify further modulators by making and testing derivatives.

Synthetic compound libraries are commercially available from a number of companies including Maybridge Chemical Co. (Trevillet, Cornwall, UK), Comgenex (Princeton, N.J.), Brandon Associates (Merrimack, N.H.), and Microsource (New Milford, Conn.).

Libraries of Test Agents:

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

A rare chemical library is available from Aldrich (Milwaukee, Wis.).

Libraries of natural compounds in the form of bacterial, fungal, plant and animal extracts are commercially available for example from Pan Laboratories (Bothell, Wash.) or MycoSearch (NC), or are readily produceable by methods well known in the art. Additionally, natural and synthetically produced libraries and compounds are readily modified through conventional chemical, physical, and biochemical means.

Other libraries include protein/expression libraries, cDNA libraries from natural sources, including, for example, foods, plants, animals, bacteria, libraries expressing randomly or systematically mutated variants of one or more polypeptides, genomic libraries in viral vectors that are used to express the mRNA content of one cell or tissue.

In a high throughput assay, it is possible to screen up to several thousand different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 modulators. If 1536 well plates are used, then a single plate can easily assay from about 100 to about 1500 different compounds. It is possible to assay several different plates per day; assay screens for up to about 6,000-20,000 different compounds is possible.

Types of Test Agents that may be Tested for their CSR::T1R Modulating Effect in the Assay Methods:

The test agents may be any agent including small chemical compounds, chemical polymers, biological polymers, peptides, proteins, sugars, carbohydrates, nucleic acids and lipids. An agent can be a synthetic compound, a mixture of compounds, a natural product or natural sample, for example plant extract, culture supernatant, or tissue sample.

As examples of compounds that may modify sweet taste there may be mentioned methyl chavicol, Theasaponin E1, Acesulfame K, Alitame, Aspartame, CH 401, Dulcin, Neotame, sodium Cyclamate, Sucralose, Superaspartame, Cynarin, Glycyphyllin, Rebaudioside C, Abrusoside A, Abrusoside B, Abrusoside C, Abrusoside D, Abrusoside E, Apioglycyrrhizin, Araboglycyrrhizin, Baiyunoside, Brazzein, Bryodulcoside, Carnosifloside V, Carnosifloside VI, D. cumminsii, Cyclocarioside A, Cyclocarioside I, Dulcoside A, Glycyrrhizic Acid, Hernandulcin, Hernandulcin, 4beta-hydroxy-Hesperitin-7-Glucoside Dihydrochalcone, Huangqioside E, Huangqioside E, 3-Hydroxyphloridzin, 2,3-Dihydro-6-Methoxy 3-O-Acetate, Mabinlin Maltosyl-Alpha-(1,6)-Neohesperidin Dihydrochalcone, Mogroside IIE, Mogroside III, Mogroside IIIE, Mogroside IV, Mogroside V, 11-Oxo Mogroside V, Monatin, Monoammonium Glycyrrhizinate (Mag), Mukuroziosideode lib, Naringin Dihydrochalcone, Neohesperidin Dihydrochalcone (NHDHC), Neomogroside, Osladin, Periandrin I, Periandrin II, Periandrin III, Periandrin IV, Periandrin V, Phlomisoside I, Phlorizin, Phyllodulcin, Polypodoside A, Potassium magnesium calcium glycyrrhizin, Pterocaryosides A, Pterocaryosides B, Rebaudioside A, Rebaudioside B, Rubusoside, Scandenoside R6, Siamenoside I, Sodium glycyrrhizinate, Steviolbioside, Stevioside, Stevioside, alpha-Glycosyl Suavioside A, Suavioside B, Suavioside G, Suavioside H, Suavioside I, Suavioside J, Thaumatin, Triammonium Glycyrrhizinate (TAG), Trilobtain Curculin, Strogin 1, Strogin 2, Strogin 4, Miraculin, Hodulcin, Jujubasaponin II, Jujubasaponin III, Abrusoside E, Periandrinic acid I, monoglucuronide, Periandrinic acid II, monoglycuronide, Chlorogenic Acid, beta-(1,3-Hydroxy-4-methoxybenzyl)-Hespertin Dihydrochalcone, 3'-Carboxy-Hespertin Dihydrochalcone, 3'-Stevioside analogue.

Identified modulators of sweet tastants may include, for example, modulators of artificial sweeteners that are able to elicit a sweet taste sensation.

Consumables include food products, beverages, oral care products, and compositions for admixture to such products, in particular flavour compositions. Flavour compositions may be added to processed foods or beverages during their processing, or they may actually be consumables in their own right, e.g. condiments such as sauces and the like. Sweet tastants are particularly interesting in confectionary and other sweet consumables including desserts, but also in savoury and sweet-sour consumables. Examples of consumables include confectionary products, cakes, cereal products, baker's products, bread products, gums, chewing gums, sauces (condiments), soups, processed foods, cooked fruits and vegetable products, meat and meat products, egg products, milk and dairy products, cheese products, butter and butter substitute products, milk substitute products, soy products, edible oils and fat products, medicaments, beverages, alcoholic drinks, beers, soft drinks, food extracts, plant extracts, meat extracts, condiments, sweeteners, nutraceuticals, pharmaceutical and non-pharmaceutical gums, tablets, lozenges, drops, emulsions, elixirs, syrups and other preparations for making beverages, instant beverages and effervescent tablets.

Sequences of Nucleic Acids and Proteins:

The sequences employed in the constructs and methods described-herein can be found in the sequence listing hereinbelow.

SEQ ID NO:1 and 19 correspond to the nucleotide/nucleic acid sequence encoding the CSR::T1R2 chimeric proteins (-a/-b), SEQ ID NO: 2 and 20 correspond to the polypeptide/amino acid sequence of the CSR::T1R2 chimeric proteins (-a and -b). SEQ ID NO:3 and 21 correspond to the nucleotide/nucleic acid sequence encoding the CSR::T1R3 chimeric proteins (-a and -b), SEQ ID NO: 4 and 22 correspond to the polypeptide/amino acid sequence of the CSR::T1R3 chimeric proteins (-a and -b).

Together as a complex comprising two subunits, the CSR::T1R2 chimeric protein and the CSR::T1R3 chimeric protein form a functional chimeric sweet receptor. The resulting complex may comprise the two -a variants, the two -b variants, or combinations (CSR::T1R2-a with CSR::T1R3-b or CSR::T1R2-b with CSR::T1R3-b), or homologous variants of these that retain their function as herein described.

In the transfected construct, the nucleic acid coding for the novel chimeric protein (SEQ ID NO:1 or 3 for variants-a, and SEQ ID NO: 19 and 21 for variants-b) is followed by the HSV tag at the C-terminus (SEQ ID NO:5).

The resulting proteins will accordingly comprise the following amino acids: amino acids of SEQ ID NO:1 followed by SEQ ID NO:5, SEQ ID NO:19 followed by SEQ ID NO:5, SEQ ID NO: 3 followed by SEQ ID NO:5, or SEQ ID NO:21 followed by SEQ ID NO:5.

The known full-length nucleic acid and protein sequences of the known T1R2 and T1R3 subunits of the T1R2/T1R3 receptor complex are given in SEQ ID NO: 7+8 for T1R2, and SEQ ID NO: 9+10 for T1R3.

The known full length hCaSR receptor nucleic acid and protein sequences are given in SEQ ID NO: 11+12.

SEQ ID NO: 1+2: CSR::T1R2-a nucleic acid+protein
SEQ ID NO: 3+4: CSR::T1R3-a nucleic acid+protein
SEQ ID NO:5+6: HSV tag at C-terminus nucleic acid+protein
SEQ ID NO:7+8: T1R2 (full length coding sequence) nucleic acid+protein
SEQ ID NO: 9+10: T1R3 (full length coding sequence) nucleic acid+protein
SEQ ID NO:11+12: hCaSR nucleic acid+protein
SEQ ID NO: 13-18: primer sequences, compare example 2a&b and example 3a&b
SEQ ID NO: 19+20: CSR::T1R2-b nucleic acid+protein
SEQ ID NO: 21+22: CSR::T1R3-b nucleic acid+protein
SEQ ID NO: 23-25: primer sequences, compare examples 2b and 3b There now follows a series of examples that serve to illustrate the above-described methods. The following examples are merely illustrative and should not be construed as limiting the methods or kit in any manner.

EXAMPLES

All examples use the DNA sequences derived from human T1R2, T1R3 and hCaSR.

Overview Examples

1: Fluo-4 Calcium Assay
2a: Preparation of CSR::T1R2-a vector construct
2b: Preparation of CSR::T1R2-b vector construct 3a: Preparation of the CSR::T1R3-a vector construct
3b: Preparation of the CSR::T1R3-b vector construct
4: Preparation of the T1R2, T1R3 vector constructs (wildtype receptors for comparison)
5: Transfections of CSR::T1R2/CSR::T1R3, and T1R2/T1R3 heterologous expression
5.2: Preparation of Stable Cell Lines expressing the CSR:T1R2/CSR:T1R3 heterodimer
6a: Activation of CSR::T1R2-a/CSR::T1R3-a
6b: Activation of CSR::T1R2-b/CSR::T1R3-b Example 1

Fluo-4 Calcium Assay

Fluo-4 is a fluorescent indicator for intracellular calcium and allows to determine changes in the calcium concentration, in particular an increase in response to receptor activation occurring after ligand addition.

HEK293 cells stably expressing $G\alpha 16$-gustducin 44 were used as host cells and transfected with various constructs as described in example 4.

Black, clear-bottom 96-well plates were used for all assays. They were seeded the day before with 8500 transfected cells per well and maintained at 37° C. overnight in an a growth medium appropriate for the cells used. For HEK293 cells, Dulbecco's Modified Eagle medium containing high glucose, L-glutamine, pyroxidine hydrochloride, and supplemented with 10% fetal bovine serum was used for growth and maintenance of the HEK293 cells.

At the time of the assay, the growth medium was discarded and cells were incubated for 1 hour (at 37° C. in the dark) with 50 µl of a calcium assay solution consisting of 1.5 µM Fluo-4 AM (Molecular Probes™, Invitrogen, US) and 2.5 µM probenicid (Sigma-Aldrich) dissolved in a reduced calcium C1 buffer solution. Reduced calcium C1 buffer solution contains 130 mM NaCl, 5 mM KCl, 10 mM Hepes, 0.5 mM CaCl2 (reduced from 2 mM) and 10 mM glucose (pH 7.4).

After the initial 1 hour loading period, the plates were washed 5 times with 100 µl per well of reduced calcium C1 buffer using an automated plate washer (BioTek) and after washing, the plate was further incubated for 30 minutes at room temperature in the dark to allow for complete de-esterification of the Fluo-4-AM. The buffer solutions were discarded, the plate was washed 5 times with 100 µl reduced calcium C1 wash buffer and finally the cells were reconstituted in 180 µl of reduced calcium C1 wash buffer.

For assay reading, the plate was placed in a FLIPR (fluorescence imaging plate reader (FLIPR-Tetra, Molecular Devices)), and receptor activation was initiated following addition of 20 µl of a 10× concentrated ligand stock solution, which were prepared in reduced calcium C1 buffer.

Fluorescence was continuously monitored for 15 seconds prior to ligand addition and for 105 seconds after ligand addition (45-105 sec may be sufficient).

Receptor activation is given in relative fluorescence units (RFU) and is defined by the following equation:

> Fluorescence Increase=Maximum Fluorescence−baseline fluorescence, wherein the baseline fluorescence represents the mean fluorescence calculated for the first 10 to 15 seconds prior to ligand addition.

As a negative control, mock transfected cells were exposed to the same concentration of ligand and the concentration of calcium traces not corresponding to a signal was determined. Cells with an activated receptor were identified by the signal (RFU) being significantly above the negative control.

Example 2a

Preparation of CSR::T1R2-a Vector Construct

The CSR::T1R2-a chimeric cDNA vector construct was generated by joining two DNA fragments generated by PCR via a common restriction enzyme site in both PCR products, namely of a PCR product representing the extracellular amino terminal domain (ATD) of hCaSR (1–$Phe^{539}$) to a PCR product representing an "-a" fragment of T1R2 containing the cysteine-rich domain (CRD), transmembrane (TMD) and C-terminus beginning at $Ser^{493}$ (T1R2-a, SEQ ID No: 1 (nucleic acid) and 2 (protein)).

To facilitate the making of the CSR::T1R2-a chimeric DNA, a Sac II site was introduced to the primers that were used to form the two fragments described hereinabove. Using these introduced sites and the appropriate restriction enzyme in buffers and under conditions well known in the art, the fragments were joined by enzymatic ligation.

These Sac II sites in the formed PCR-products/fragments are located at the C-terminal end of the hCaSR ATD fragment and the N-terminal end of the T1R2-a fragment, respectively, allowing for ligation of the two PCR-products/fragments of the chimeric DNA. Incorporation of this Sac II site converts $Phe^{539}$ in the hCaSR into an arginine residue. PCR using Platinum Taq High Fidelity Polymerase was used to amplify the fragments that comprise the CSR:T1R2-a chimeric cDNA fragment using the specific primers of SEQ ID 13-16 which are given below. F designates the forward primer, R the reverse primer.

The underligned letters designate restriction sites located within the primers for subsequent subcloning of the PCR products.

```
hCaSR-ATD primer F (Seq ID NO: 13):
CACCAAGCTTATGGCATTTTATAGCTGC hCaSR-ATD primer R (Seq ID NO: 14):
ATATCCGCGGCACCTCCCTGGAGAACCC T1R2-fragment primer F (Seq ID NO: 15):
ATATCCGCGGTCCATGTGTTCCAAGAGG T1R2-fragment primer R (Seq ID NO: 16):
ATATGCGGCCGCAGTCCCTCCTCATGGT
```

The template for the PCR amplification was a full length cDNA for either the human CaSR (commercially available from Origene Inc., USA), or the human T1R2, which was isolated from a cDNA library generated from human fungiform papillae taste tissue. PCR reaction parameters were: 94° C. for 5 min followed by 35 cycles of 94° C. for 45 seconds, 54° C. for 15 seconds and 72° C. for 2 minutes, followed by a final extension cycle of 72° C. for 10 minutes.

The resulting nucleic acid fragments were separated by gel electrophoresis, purified and subcloned into the pCR-Topo-II vector (Invitrogen) and the resulting clones were verified by DNA sequencing to ensure absence of mutations arising from the PCR amplification.

After sequencing, the inserts were subcloned into an expression cassette vector construct based on the pcDNA4-TO vector (purchased from Invitrogen, USA) via 3-piece ligation, allowing for assembly of the CSR::T1R2-a chimeric cDNA fragment in the vector construct.

The C-terminus of the formed vector construct encodes the herpes simplex virus (HSV) glycoprotein D epitope, which can be used for immunocytochemistry studies using a specific antibody that binds to this epitope. The resulting CSR:

T1R2-a vector construct with CSR:T1R2-a cDNA allows for expression of the CSR:T1R2-a:HSV protein of joined amino acid sequences of Seq ID NO:2 (CSR:T1R2-a) followed by Seq ID NO:6 (HSV epitope) (in amino terminus to C terminus direction).

Example 2b

Preparation of CSR::T1R2-b Vector Construct

The CSR::T1R2-b chimeric cDNA vector construct was generated by joining two DNA fragments generated by PCR via a common restriction enzyme site in both PCR products, namely of a PCR product representing the extracellular amino terminal domain (ATD) and cysteine-rich domain (CRD) of hCaSR (1–Ile$^{603}$) to a PCR product representing a "-b" fragment of T1R2 containing the transmembrane (TMD) and C-terminus beginning at Val$^{557}$ (T1R2-b, SEQ ID No: 19 (nucleic acid) and 20 (protein)).

To facilitate the making of the CSR:T1R2-b chimeric DNA, a BsiW I site was introduced to the primers that were used to form the two fragments described hereinabove. Using these introduced sites and the appropriate restriction enzyme in buffers and under conditions well known in the art, the fragments were joined by enzymatic ligation.

These BsiW I sites in the formed PCR-products/fragments are located at the C-terminal end of the hCaSR ATD fragment and the N-terminal end of the T1R2-b fragment, respectively, allowing for ligation of the two PCR-products/fragments of the chimeric DNA. Incorporation of this BsiW I site converts Glu$^{602}$/Ile$^{603}$ in the hCaSR into an Arg/Thr residues. PCR using Platinum Taq High Fidelity Polymerase was used to amplify the fragments that comprise the CSR:T1R2-b chimeric cDNA fragment using the specific primers of SEQ ID 13, 16, 23 and 24 which are given below. F designates the forward primer, R the reverse primer.

The underligned letters designate restriction sites located within the primers for subsequent subcloning of the PCR products.

```
hCaSR-ATD primer F (Seq ID NO: 13):
CACCAAGCTTATGGCATTTTATAGCTGC hCaSR-ATD primer R (Seq ID NO: 23):
ATA TCG TAC GCT TGG CAA TGC AGG AGG T T1R2-fragment primer F (Seq ID NO: 24):
ATA TCG TAC GGT CTT CCT GGA ATG GCA T T1R2-fragment primer R (Seq ID NO: 16):
ATATGCGGCCGCAGTCCCTCCTCATGGT
```

The template for the PCR amplification was a full length cDNA for either the human CaSR (commercially available from Origene Inc., USA), or the human T1R2, which was isolated from a cDNA library generated from human fungiform papillae taste tissue. PCR reaction parameters were: 94° C. for 5 min followed by 35 cycles of 94° C. for 45 seconds, 54° C. for 15 seconds and 72° C. for 2 minutes, followed by a final extension cycle of 72° C. for 10 minutes.

The resulting nucleic acid fragments were separated by gel electrophoresis, purified and subcloned into the pCR-Topo-II vector (Invitrogen) and the resulting clones were verified by DNA sequencing to ensure absence of mutations arising from the PCR amplification.

After sequencing, the inserts were subcloned into an expression cassette vector construct based on the pcDNA4-TO vector (purchased from Invitrogen, USA) via 3-piece ligation, allowing for assembly of the CSR::T1R2-b chimeric cDNA fragment in the vector construct.

The C-terminus of the formed vector construct encodes the herpes simplex virus (HSV) glycoprotein D epitope, which can be used for immunocytochemistry studies using a specific antibody that binds to this epitope. The resulting CSR:T1R2-b vector construct with CSR:T1R2-b cDNA allows for expression of the CSR:T1R2-b:HSV protein of joined amino acid sequences of Seq ID NO:20 (CSR:T1R2-b) followed by Seq ID NO:6 (HSV epitope) (in amino terminus to C terminus direction).

Example 3a

Preparation of the CSR::T1R3-a Vector Construct

The CSR::T1R3-a chimeric cDNA vector construct was generated by joining two DNA fragments generated by PCR via a common restriction enzyme site in both PCR products, namely the joining of a PCR product representing the extracellular amino terminal domain (ATD) of hCaSR (1–Phe$^{539}$) to a fragment of T1R3 containing the cysteine-rich domain (CRD), transmembrane (TMD) and C-terminus beginning at Ser$^{497}$.

To facilitate the making of the CSR::T1R3-a chimeric cDNA vector construct, a Sac II site was introduced into the primers which were used to make the above-described two fragments.

These Sac II sites in the formed PCR-products/fragments are located at the C-terminal end of the hCaSR-ATD fragment and the N-terminal end of the T1R3-a fragment, respectively, allowing for ligation of the two fragments. Incorporation of this Sac II site results in a vector construct that comprises a sequence wherein the Phe$^{539}$ of the previous hCaSR is converted into an arginine residue. Using the introduced ligation sites and the appropriate restriction enzyme in buffers and under conditions well known in the art, the fragments were joined by enzymatic ligation.

PCR using Platinum Taq High Fidelity Polymerase was used to amplify the fragments that comprise the CSR::T1R3-a chimeric cDNA fragment using the specific primers of Seq ID NO: 17 and Seq ID NO:18 listed below. Afterwards, the amplified PCR-products of T1R3-a and the amplified PCR products of hCaSR (the latter formed as described in example 2 above) were ligated via the restriction sites indicated in the primer listed below. F designates the forward primer, R the reverse primer. The underlined letters designate restriction sites located within the primers for subsequent ligation and subcloning of the amplified PCR products. hCaSR-ATD F and hCaSR-ATD R:

Seq ID NO: 13 and Seq ID NO: 14 as indicated in example 2a above.

```
TAS1R3-a-fragment primer F (Seq ID NO: 17):
ATATCCGCGGTCCCGGTGCTCGCGGCAG

TAS1R3-fragment primer R (Seq ID NO: 18):
ATATGCGGCCGCACTCATGTTTCCCCTGATT
```

The template for the PCR amplification was a full length cDNA for either the hCaSR (purchased from Origene Inc., USA), or the hT1R3, which was isolated from a cDNA library generated from human fungiform papillae taste tissue.

PCR reaction parameters were: 94° C. for 5 min followed by 35 cycles of 94° C. for 45 seconds, 54° C. for 15 seconds and 72° C. for 2 minutes, followed by a final extension cycle of 72° C. for 10 minutes.

The resulting nucleic acid fragments (ligation is performed later after the fragments are verified) were separated by gel electrophoresis, purified and subcloned into the pCR-Topo-II vector (Invitrogen, USA). The resulting clones were verified by DNA sequencing to ensure absence of mutations arising from the PCR amplification.

After sequencing, the inserts were subcloned into an expression cassette vector construct based on the pcDNA4-TO vector (purchased from Invitrogen, USA) via 3-piece ligation, forming the CSR::T1R3-a vector construct. The C-terminus of the formed vector construct encodes the herpes simplex virus (HSV) glycoprotein D epitope, which can be used for immunocytochemistry studies using a specific antibody that binds to this epitope. The resulting vector construct allows for expression of the CSR::T1R3-a::HSV protein of joined amino acid sequences of Seq ID NO:4 (CSR::T1R3-a) followed by Seq ID NO:6 (HSV epitope) (in amino terminus to C terminus direction).

Example 3b

Preparation of the CSR::T1R3-b Vector Construct

The CSR::T1R3-b chimeric cDNA vector construct was generated by joining two DNA fragments generated by PCR via a common restriction enzyme site in both PCR products, namely the joining of a PCR product representing the extracellular amino terminal domain (ATD) and cysteine-rich domain (CRD) of hCaSR (1–Ile$^{603}$) to a PCR product representing a fragment of T1R3 containing the transmembrane (TMD) and C-terminus beginning at Arg$^{560}$.

To facilitate the making of the CSR::T1R3-b chimeric cDNA vector construct, a BsiW I site was introduced into the primers which were used to make the above-described two fragments.

These BsiW I sites in the formed PCR-products/fragments are located at the C-terminal end of the hCaSR-ATD fragment and the N-terminal end of the T1R3-b fragment, respectively, allowing for ligation of the two fragments. Incorporation of this BsiW I site results in a vector construct that comprises a sequence wherein the Phe$^{539}$ of the previous hCaSR is converted into an arginine residue. Using the introduced ligation sites and the appropriate restriction enzyme in buffers and under conditions well known in the art, the fragments were joined by enzymatic ligation.

PCR using Platinum Taq High Fidelity Polymerase was used to amplify the fragments that comprise the CSR:: T1R3-b chimeric cDNA fragment using the specific primers of Seq ID NO: 25 and Seq ID NO:18 listed below. Afterwards, the amplified PCR-products of T1R3-b and the amplified PCR products of hCaSR (the latter formed as described in example 2b above) were ligated via the restriction sites indicated in the primer listed below. F designates the forward primer, R the reverse primer. The underligned letters designate restriction sites located within the primers for subsequent ligation and subcloning of the amplified PCR products. hCaSR-ATD F and hCaSR-ATD R:

Seq ID NO: 13 and Seq ID NO: 23 as indicated in example 2b above.

```
TAS1R3-fragment primer F-b (Seq ID NO: 25):
ATA TCG TAC GCG GTT CCT GGC ATG GGG C TAS1R3-fragment primer R (Seq ID NO: 18):
ATATGCGGCCGCACTCATGTTTCCCCTGATT
```

The template for the PCR amplification was a full length cDNA for either the hCaSR (purchased from Origene Inc., USA), or the hT1R3-b, which was isolated from a cDNA library generated from human fungiform papillae taste tissue.

PCR reaction parameters were: 94° C. for 5 min followed by 35 cycles of 94° C. for 45 seconds, 54° C. for 15 seconds and 72° C. for 2 minutes, followed by a final extension cycle of 72° C. for 10 minutes.

The resulting nucleic acid fragments (ligation is performed later after the fragments are verified) were separated by gel electrophoresis, purified and subcloned into the pCR-Topo-II vector (Invitrogen, USA). The resulting clones were verified by DNA sequencing to ensure absence of mutations arising from the PCR amplification.

After sequencing, the inserts were subcloned into an expression cassette vector construct based on the pcDNA4-TO vector (purchased from Invitrogen, USA) via 3-piece ligation, forming the CSR::T1R3-b vector construct. The C-terminus of the formed vector construct encodes the herpes simplex virus (HSV) glycoprotein D epitope, which can be used for immunocytochemistry studies using a specific antibody that binds to this epitope. The resulting vector construct allows for expression of the CSR::T1R3-b::HSV protein of joined amino acid sequences of Seq ID NO:22 (CSR::T1R3-b) followed by Seq ID NO:6 (HSV epitope) (in amino terminus to C terminus direction).

Example 4

Preparation of the T1R2, T1R3 Vector Constructs

Wildtype Receptors for Comparison

To form The T1R2 and T1R3 Vector Construct, cDNA fragments containing the entire protein coding sequences for human T1R2 and T1R3 were isolated from a human fungiform cDNA library, fully sequenced and then subcloned into pcDNA3.1 (Invitrogen).

Example 5

Transfections of CSR::T1R2/CSR::T1R3, and T1R2/T1R3 Heterologous Expression

Transfected vector constructs used were those described in examples 2a and 3a, or 2b and 3b, and 4, formed as described above. For hCaSR, a commercially available pCMV-based vector construct which is based on the full length cDNA was used (TRUECLONE collection, Origene inc., USA).

HEK293T cells that stably express Gα16-gustducin 44 (formed as described in WO 2004/055048) were transfected with the CSR::T1R2 and CSR::T1R3 vector constructs, or with T1R2 and T1R3, or hCaSR as follows:

On day 0, the HEK293T/Gα16-gustducin 44 cells were plated in 96-well black, clear-bottom plates at a density of 8500 cells per well and grown overnight in selective growth media. On day 1, the media was changed to an antibiotic-free and serum-free growth medium and the cells were transfected using 75 ng each of CSR:T1R2 (-a or -b) and CSR:T1R3 (total 150 ng) (-a or -b), T1R2 and T1R3 (total 150 ng), or 75 ng hCaSR vector construct DNA and 0.3 μl of Lipofectamine 2000 (Invitrogen).

The hCaSR vector is used as positive control for a GPCR that is sensitive to calcium, as it is sensitive to calcium and the calcium binding site lies in the VFT of this receptor, which is where the VFT for the chimera is derived from.

For transfection of either the CSR:T1R2/CSR:T1R3 (CSR: T1R2-a/CSR:T1R3-a or CSR:T1R2-b/CSR:T1R3-b) or T1R2/T1R3 heterodimers, 75 ng of each vector construct was combined for a total of 150 ng per pair and used together with 0.3 µl of Lipofectamine 2000. 75 ng of hCaSR vector DNA was used for this calcium-sensing monomeric GPCR.

The above-described lipofectamine/DNA mixtures were incubated on the cells for 3-4 hours and then replaced with an antibiotic-free, serum-containing growth medium. The cells were grown overnight and the Fluo-4 calcium assay was performed as described in example 1.

The cells transiently transfected with one of the above-described vector constructs were identified using a fluorescence imaging plate reader (FLIPR-Tetra, Molecular Devices) as described in example 1.

Example 5.2

Preparation of Stable Cell Lines Expressing the CSR::T1R2-a/CSR::T1R3-a Heterodimer A stable cell line was generated in which CSR::T1R3-a was constitutively over-expressed in the presence of a tetracycline-regulated CSR::T1R2-a to avoid possible cytotoxic effects of constitutive over-expression of both proteins. DNA encoding one subunit of the heterodimer (CSR::T1R2-a) was placed in a tetracycline-regulated vector to allow regulation of its expression level so that viability and functionality of the stable clonal lines can be optimised.

Human cell lines that stably express the chimeric human CSR::T1R2-a/CSR::T1R3-a heterodimer were generated sequentially by first transfecting a linearized pcDNA4-TO vector (Invitrogen) containing the human CSR::T1R2-a into a Gα16gust44 expressing cell line, which was prepared as described in WO 2004/055048. The Gα16gust44 expressing cell line shows enhanced coupling to taste receptors, is tetracycline inducible, stably expresses the Gα16gust44 promiscuous G-protein, and is based on the HEK-293-T-Rex cell line (commercially available from Invitrogen, USA). A clonal cell line expressing CSR:T1R2-a was identified and transfected with a linearized pcDNA3.1-Hygro vector (Invitrogen) containing human CSR::T1R3-a cDNA to obtain a double stable clonal cell line that expresses both CSR::T1R2-a and CSR::T1R3-a.

24 hours after transfection with 4 micrograms of the linearized CSR:T1R2-a/pcDNA4TO construct and 0.3 µl of Lipofectamine 2000 (Invitrogen), cells were re-plated at 10× dilutions up to 1:150,000 in selective medium containing DMEM (Invitrogen) supplemented with 10% FBS, 0.005 mg/ml blasticidin, 0.36 mg/ml G418, and 0.2 mg/ml Zeocin at 37° C. After 2-3 weeks, Zeocin-resistant colonies were individually expanded and stable clones were selected based on a functional response to 50 micromolar perillartine following a 4 hour induction with 10 µg/ml tetracycline to allow for expression of the CSR::T1R2-a cDNA. We identified an individual clone (#17) that exhibited minimal basal expression of the CSR::T1R2-a cDNA and used this as a recipient for the CSR:T1R3-a construct to generate a stable cell line for the heterodimeric receptor complex. Clone 17 containing the inducible CSR::T1R2-a was transfected with 4 µg of the linearized CSR::T1R3-a/pcDNA3.1-Hygro vector construct DNA and 0.3 µl of Lipofectamine 2000 (Invitrogen). The lipofectamine/DNA mixture was incubated on the cells for 3-4 hours and then replaced with an antibiotic-free, serum-containing growth medium. After 24 hours the cells were re-plated in selective medium containing DMEM supplemented with 10% FBS, 0.005 mg/ml blasticidin, 0.36 mg/ml G418, 0.2 mg/ml zeocin, and 0.2 mg/ml hygromycin at 37° C.

Resistant colonies were expanded, and identified as containing the CSR::T1R2-a/CSR::T1R3-a heterodimer on the basis of a response to both perillartine (contributed by binding/activation of CSR::T1R2-a) and to sodium cyclamate (contributed by binding/activation of CSR:T1R3-a), which was determined via automated fluorimetric imaging on the FLIPR-Tetra instrumentation (Molecular Devices) using the methods described in example 1. All potential clones were evaluated for a functional response to sweet tastants following induction with 10 µg/ml tetracycline (to induce over-expression of CSR::T1R2-a). Potential clones were also tested in the absence of tetracycline induction to identify any clones that basally express T1R2-a at a low level, but have sufficient expression of the CSR::T1R2-a receptor to allow for assembly with CSR::T1R3-a resulting in a functional heterodimer complex (the tetracycline-regulated systems such as the T-Rex HEK-293 (Invitrogen) are known to have a low-level basal expression of transgenes due to the inherent leakiness of the system). Stable clones expressing an inducible functional CSR::T1R2-a/CSR::T1R3-a heterodimer were identified on the basis of a response to both-50 microM perillartine and to 5 mM (milliM) sodium cyclamate. One clonal cell line exhibiting the greatest tetracycline-inducible response to multiple sweet tastants was propagated and used for subsequent comparisons. The results for tests with various ligands/sweet tastants are indicated in the table below.

TABLE 1

| Ligand | Ligand Concentration | CSR:T1R2-a/CSR:T1R3-a | | T1R2/T1R3 | | G16gust44 (NEG. CONTROL) | |
| --- | --- | --- | --- | --- | --- | --- | --- |
| | | AVG (dF/F) | S.D. (dF/F) | AVG (dF/F) | S.D. (dF/F) | AVG (dF/F) | S.D. (dF/F) |
| p-ETBZ | 100 microM | 1.11 | 0.05 | 1.029 | 0.1 | 0.16 | 0.01 |
| NDHC | 1 mM | 1.64 | 0.23 | 1.71 | 0.05 | 0.23 | 0.01 |
| NarDHC | 1 mM | 1.43 | 0.23 | 1.40 | 0.15 | 0.22 | 0.07 |
| Cyclamate | 5 mM | 1.28 | 0.063 | 1.60 | 0.08 | 0.17 | 0.06 |

The data indicates the normalized increase in fluorescence over baseline after stimulation ($\Delta F/F$) using the following equation: $\Delta F/F=(F-F_0)/F_0$, where F is the peak fluorescence signal and $F_0$ is the baseline fluorescence signal, which is determined from the average fluorescence signal measured prior to ligand addition. The AF/F value obtained corresponds to the calcium increase of the cell in response to a direct or indirect interaction with the transfected receptor ("signal") (the mean (AVG) and standard deviation (S.D.) of three replicate experiments is given).

The chemical structure of the ligands is shown below.

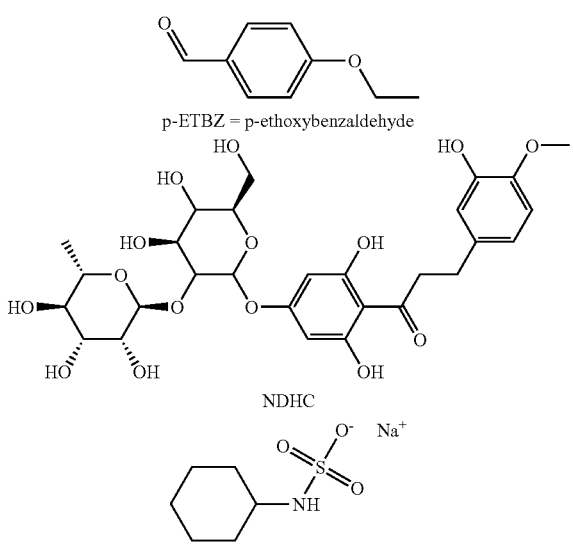

Calcium Chloride (2 mM), Sucralose (0.5 mM), aspartame (0.85 mM), perillartine (50 µM), cinnamonitrile (100 EM), cyclamate (1 mM), Neohesperidin Dihydrochalcone (NDHC) (0.33 mM).

The signals obtained are the fluorescence in RFU corresponding to the calcium increase of the cell in response to a direct or indirect interaction with the transfected receptor ("signal").

Mock transfected HEK293T/Gα16-gustducin 44 cells transfected without construct that do not express a sweet receptor were used as a negative control to determine signals corresponding merely to the background.

The transfected cells are exposed to the sweeteners as indicated and to a positive control (calcium) for the proteins containing Calcium-sensing domains, and to a negative control (C1 buffer).

The results are shown in the table below.

The AVG column gives the mean fluorescence, the STD column gives the standard deviation. The table below shows the average change in RFUs+/−STD for the 6 replicates for each of the various vector constructs tested.

TABLE 2a

| Results | | | | | | | | |
|---|---|---|---|---|---|---|---|---|
| | CSR::T1R2-a/ CSR::T1R3-a | | hCaSR | | T1R2/T1R3 | | Neg. control (mock transfection) | |
| | AVG | STD | AVG | STD | AVG | STD | AVG | STD |
| Positive control (Calcium) | 3912 | 295 | 7610 | 1776 | 1361 | 426 | 1570 | 509 |
| Aspartame | 72 | 78 | 41 | 97 | 531 | 154 | −125 | 116 |
| Sucralose | −75 | 130 | 22 | 92 | 601 | 173 | −186 | 36 |
| Perillartine | 2400 | 466 | 73 | 354 | 1840 | 333 | −379 | 327 |
| Cinnamonitrile | 1501 | 194 | 197 | 33 | 632 | 484 | −998 | 36 |
| Cyclamate | 370 | 213 | 196 | 79 | 341 | 132 | −324 | 297 |
| NDHC | 631 | 233 | −257 | 53 | 331 | 129 | −524 | 44 |
| Negative control (C1 buffer) | −115 | 70 | 57 | 101 | −63 | 131 | −217 | 204 |

Sodium Cyclamate (Cyclamate is a sweet tastant. The additional presence of sodium ions improves water solubility, but does not further contribute to sweet taste)

Example 6a

Activation of CSR::T1R2-a/CSR::T1R3-a

The intracellular calcium response following stimulation with various ligands was determined in HEK293T cells stably expressing Gα116-gustducin 44 and transfected with CSR::T1R2-a/CSR::T1R3-a chimeric heterodimer. The results were compared to results obtained in cells transfected with the both the T1R2 vector construct and the T1R3 vector construct which is described in example 4 (to form the wild-type T1R2/T1R3 sweet heterodimer) or the hCaSR vector construct described in example 5 (to form monomeric hCaSR).

The transfections were performed as described in example 4. Results were calculated as described in example 1 (data indicates the net increase in fluorescence over baseline after stimulation (Relative Fluorescent Units or RFU); the mean (AVG) and the ±Standard deviation (STD) of six replicate experiments is given). The following ligands were used for to stimulate the transfected cells in the concentrations as indicated in brackets:

The negative control/mock transfection shows the signal level corresponding to background signals.

As the positive control (calcium) shows, all transfected cells which have a calcium-sensing domain react to calcium (CSR::T1R2-a/CSR::T1R3-a heterodimer and hCaCSR)

The response of the chimeric heterodimer to calcium can not be compared to those obtained with the sweet heterodimer. Since calcium is not an agonist of the T1R2/T1R3 sweet heterodimer it did not give signals that were greater than mock transfected cells expressing only the Gα16-gustducin 44 g-protein.

For aspartame and sucralose, a signal is detected in the cells transfected with the T1R2/1R3 heterodimer only. Sucralose and aspartame are believed to bind in the VFT of T1R2, which is absent in the CSR:T1R chimera, which explains the lack of signal in the CSR::T1R2-a/CSR::T1R3-a heterodimer.

The hCaSR responded only to calcium chloride and could not be activated by any of the sweet tastants tested.

For calcium chloride, perillartine, cinnamonitrile, cyclamate and NDHC, a significant increase of the signal was observed in cells expressing the CSR::T1R2-a/CSR::T1R3-a chimeric heterodimer.

For perillartine, cinnamonitrile, cyclamate, and NDHC these signals were comparable in intensity to the signal detected for the T1R2/T1R3 heterodimer.

These signals detected in the cells transfected with the chimeric CSR::T1R2-a/CSR::T1R3-a heterodimer were significantly higher than both the signal in the T1R2/T1R3 heterodimer and the background signals obtained in the negative control (mock transfected HEK293T/Gα16-ducin 44 cells), and were approximately 50% of the magnitude of signals obtained in cells transfected with the hCaSR receptor.

The results demonstrate that CSR::T1R2-a/CSR::T1R3-a is activated by calcium, perillartine, cyclamate, cinnamonitrile, and neohesperidin dihydrochalcone (NDHC) but not by sucralose or aspartame.

Example 6b

Activation of CSR::T1R2-b/CSR::T1R3-b

The intracellular calcium response following stimulation with various ligands was determined in HEK293T cells stably expressing Gα16-gustducin 44 and transfected with CSR::T1R2-b/CSR::T1R3-b chimeric heterodimer. The results were compared to results obtained in cells transfected with the both the T1R2 vector construct and the T1R3 vector construct which is described in example 4 (to form the T1R2/T1R3 sweet heterodimer) or the hCaSR vector construct described in example 5 (to form monomeric hCaSR).

The transfections were performed as described in example 4. Results were calculated as described in example 1 (data indicates the normalized increase in fluorescence over baseline after stimulation (ΔF/F); the mean (AVG) and the Standard deviation (STD) of six replicate experiments is given). Calcium Chloride (2 mM), Sucralose (0.5 mM), perillartine (50 μM), were used as the test ligands.

The calcium mobilization signals obtained are increase in peak fluorescence (F) normalized to the baseline fluorescence ($F_0$). The data are normalized using the following equation: $\Delta F/F=(F-F_0)/F_0$, where F is the peak fluorescence signal and $F_0$ is the baseline fluorescence signal, which is determined from the average fluorescence signal measured prior to ligand addition. The ΔF/F value obtained corresponds to the calcium increase of the cell in response to a direct or indirect interaction with the transfected receptor ("signal").

Mock transfected HEK293T/Gα16-gustducin 44 cells transfected without construct that do not express a sweet receptor were used as a negative control to determine signals corresponding merely to the background.

The transfected cells are exposed to the sweeteners as indicated and to a positive control (calcium) for the proteins containing Calcium-sensing domains, and to a negative control (C1 buffer).

The results are shown in the table below.

The AVG column gives the mean ΔF/F, the STD column gives the standard deviation. The table below shows the average change in ΔF/F+/−STD for the 6 replicates for each of the various vector constructs tested.

The negative control/mock transfection shows the signal level corresponding to background signals.

As the positive control (calcium) shows, all transfected cells which have a calcium-sensing domain react to calcium (CSR::T1R2-b/CSR::T1R3-b heterodimer and hCaSR)

The response of the chimeric heterodimer to calcium can not be compared to those obtained with the sweet heterodimer. Since calcium is not an agonist of the T1R2/T1R3 sweet heterodimer it did not give signals that were greater than mock transfected cells expressing only the Gα16-gustducin 44 g-protein.

For sucralose, a signal is detected in the cells transfected with the T1R2/1R3 heterodimer (wildtype) only. Sucralose is believed to bind in the VFT of T1R2, which is absent in the CSR::T1R chimerae, which explains the lack of signal in the CSR::T1R2-b/CSR::T1R3-b heterodimer.

The hCaSR responded only to calcium chloride and could not be activated by any of the sweet tastants tested.

For calcium chloride, perillartine, a significant increase of the signal was observed in cells expressing the CSR::T1R2-b/CSR::T1R3-b chimeric heterodimer as well as the CSR::T1R2-b homomer expressed in the absence of any T1R3 construct or its variants.

These signals detected in the cells transfected with the chimeric CSR::T1R2-b/CSR::T1R3-b heterodimer were significantly higher than the background signals obtained in the negative control (mock transfected HEK293T/Gα16-gustducin 44 cells)

The results demonstrate that CSR::T1R2-b/CSR::T1R3-b is activated by calcium and perillartine, but not by sucralose.

While the receptors, nucleic acids, polypeptides, methods and kit have been described above in connection with certain illustrative embodiments, it is to be understood that other similar embodiments may be used or modifications and additions may be made to the described embodiments for performing the same function(s). Further, all embodiments disclosed are not necessarily in the alternative, as various embodiments may be combined to provide the desired characteristics. Variations can be made by one having ordinary skill in the art without departing from the spirit and scope of the disclosure. Therefore, the receptors, nucleic acids, polypeptides, methods and kit should not be limited to any single embodiment, but rather construed in breadth and scope in accordance with the recitation of the attached claims.

TABLE 2b

| | Results | | | | | | | |
|---|---|---|---|---|---|---|---|---|
| | CSR::T1R2-b/ CSR::T1R3-b | | CSR::R2-b alone | | T1R2/T1R3 | | Neg. control (mock transfection) | |
| | AVG | STD | AVG | STD | AVG | STD | AVG | STD |
| Positive control (Calcium) | 0.46 | 0.11 | 0.424 | 0.02 | 0.19 | 0.001 | 0.20 | 0.01 |
| Sucralose | 0.017 | 0.006 | 0.016 | 0.001 | 0.12 | 0.006 | 0.03 | 0.00 |
| Perillartine | 0.169 | 0.04 | 0.11 | 0.02 | 0.5 | 0.02 | 0.06 | 0.02 |
| Negative control (C1 buffer) | 0.017 | 0.001 | 0.036 | 0.008 | 0.03 | 0.01 | 0.03 | 0.002 |

The invention claimed is:

1. A CSR::T1R chimeric protein able to bind to at least one sweetener or sweetness enhancer, comprising one or more CSR::T1R polypeptides selected from the group consisting of
 a CSR::T1R2 polypeptide with a sequence identity of at least 90% to SEQ ID NO:2 or SEQ ID NO:20 and,
 a CSR::T1R3 polypeptide with a sequence identity of at least 90% to SEQ ID NO:4 or SEQ ID NO: 22.

2. A CSR::T1R chimeric protein according to claim 1 comprising two polypeptide subunits in form of a heterodimeric protein selected from the group consisting of
 a CSR::T1R2/CSR::T1R3 heterodimeric chimeric protein,
 a CSR::T1R2/T1R3 heterodimeric chimeric protein, and a T1R2/CSR::T1R3 heterodimeric chimeric protein,
 wherein the T1R2 subunit of the heterodimer comprises a polypeptide with a sequence identity of at least 90% to SEQ ID NO:8;
 and wherein the T1R3 subunit of the heterodimer comprises a polypeptide with a sequence identity of at least 90% to SEQ ID NO:10.

3. A CSR::T1R chimeric protein comprising two polypeptide subunits according to claim 2 which comprises a CSR::T1R2/CSR::T1R3 heterodimeric chimeric protein selected from the group consisting of a CSR::T1R2-a/CSR::T1R3-a heterodimeric protein, a CSR::T1R2-b/CSR::T1R3-b heterodimeric protein, a CSR::T1R2-a/CSR::T1R3-b heterodimeric protein, a CSR::T1R2-b/CSR::T1R3-a heterodimeric protein, or a heterodimeric protein with a sequence identity of at least 90%, wherein CSR::T1R2-a corresponds to SEQ ID NO: 2, CSR::T1R2-b corresponds to SEQ ID NO:20, CSR::T1R3-a corresponds to SEQ ID NO:4 and CSR::T1R3-b corresponds to SEQ ID NO:22.

4. A nucleic acid encoding a CSR::T1R chimeric protein of claim 1 that is able to bind at least one sweetener or sweetness enhancer comprising one or more of
 a nucleic acid with a sequence identity of at least 90% as determined by hybridization to a nucleotide sequence selected from the group consisting of SEQ ID NO:1 (CSR::T1R2-a), SEQ ID NO: 19 (CSR::T1R2-b); SEQ ID NO:3 (CSR::T1R3-a) and SEQ ID NO: 21 (CSR::T1R3-b) under stringent hybridization conditions at a temperature of 42° C. in a solution consisting of 50% formamide, 5×SSC, and 1% SDS, and washing at 65° C. in a solution consisting of 0.2×SSC and 0.1% SDS,
 a nucleic acid encoding a CSR::T1R2 polypeptide with a sequence identity of at least 90% to SEQ ID NO:2 or SEQ ID NO:20,
 a nucleic acid encoding a CSR::T1R3 polypeptide with a sequence identity of at least 90% to SEQ ID NO:4 or SEQ ID NO: 22, and
wherein the nucleic acid optionally comprises SEQ ID NO:6 (HSV tag) at or near its end to form the C-terminus in the corresponding protein.

5. An expression vector comprising the nucleic acid as defined in claim 4.

6. A host cell transfected with an expression vector as defined in claim 5.

7. A host cell stably expressing a CSR::T1R chimeric protein as defined in claim 1 and a G-Protein, optionally a G-Protein with a sequence identity of at least 90% to Gaq-Gustducin.

8. A host cell transiently expressing a CSR::T1R chimeric protein as defined in claim 1 and a G-Protein, optionally a G-Protein with a sequence identity of at least 90% to Gaq-Gustducin.

9. A method of producing a CSR::T1R chimeric protein as defined in claim 1, 2 or 3, comprising culturing host cells other than bacterial cells comprising an expression vector encoding for the CSR::T1R chimeric protein under conditions sufficient for expression, thereby forming the CSR::T1R chimeric protein and optionally recovering it from the cells.

10. A method to identify an agent that modulates sweet taste signaling in taste cells, the method comprising:
    (i) contacting cells that express a CSR::T1R chimeric protein that responds to stimuli selected from sweet taste stimuli and calcium stimuli with an agent thereby providing a functional response, optionally in presence of another agent; and
    (ii) determining whether at least one agent affects the functional response of said CSR::T1R chimeric protein in said cells by at least one functional response in said cells; wherein said CSR::T1R chimeric protein is as defined in claim 1, 2 or 3.

11. A method according to claim 10 wherein the cells also express a G-Protein.

12. A method according to claim 11 wherein the G-Protein is a chimeric G-protein with a sequence identity of at least 90% to Gaq-Gustducin.

13. A method according to claim 12 wherein the G-Protein is the chimeric G-protein G alpha 16-gustducin 44.

14. A method according to claim 10 wherein step (ii) is performed by measuring a change in or caused by intracellular messengers.

15. A method according to claim 11 wherein the functional response is determined by measuring a change in an intracellular messenger selected from IP3 and calcium$^{2+}$.

16. The method of claim 10 wherein said cells are selected from the group consisting of, eucaryotic cells, yeast cells, insect cells, mammalian cells, amphibian cells, and worm cells.

17. The method according to claim 16 wherein said cells are mammalian cells.

18. The method according to claim 17 wherein the mammalian cells are selected from the group consisting of CHO, COS, HeLa and HEK-293 cells.

19. The method according to claim 10 wherein step (i) further comprises contacting the CSR::T1R chimeric protein with a test agent in presence of calcium.

20. The method according to claim 19 wherein the calcium is provided in the form of calcium chloride.

21. A kit comprising:
    (i) recombinant cells that express a CSR::T1R chimeric protein as defined in claim 1, 2 or 3, and
    (ii) an agonist of the CSR::T1R chimeric protein, for combined use to identify test agents as modulators of the CSR::T1R chimeric protein.

22. A method of using the kit of claim 21, comprising:
    (i) growing said recombinant cells that express a CSR::T1R chimeric protein,
    (ii) adding test agents in the presence of the agonist in a suitable concentration, and
    (iii) determining a change in a functional response of the cells by comparing the response in presence and absence of the test agent, and the test agent is thereby identified as a modulator of the CSR::T1R chimeric protein as defined in claim 1, 2, or 3.

23. A method to identify an agent that modulates the CSR::T1R chimeric protein as defined in claim 1, 2, or 3, the method comprising:
    (i) measuring a parameter that changes in response to a ligand binding to the CSR::T1R chimeric protein, and
    (ii) determining a change of the parameter in response to a test agent, optionally in presence of a ligand, in comparison to a negative control and thereby identifying a modulator or ligand.

24. Method according to claim 23 wherein the ligand is selected from the group consisting of calcium, calcium ions and calcium chloride.

25. Method according to claim 23 wherein step (i) is performed by a method selected from the group consisting of fluorescence spectroscopy, NMR spectroscopy, measuring of one or more of absorbance, refractive index, hydrodynamic methods, chromatography, measuring solubility, biochemical methods, wherein the methods measure the properties of the CSR::T1R chimeric protein in a suitable environment selected form the group consisting of solution, bilayer membrane, attached to a solid phase, in a lipid monolayer, bound on a membrane, and in vesicles.

26. Method according to claim 24 wherein step (i) is performed by a method selected from the group consisting of fluorescence spectroscopy, NMR spectroscopy, measuring of one or more of absorbance, refractive index, hydrodynamic methods, chromatography, measuring solubility, biochemical methods, wherein the methods measure the properties of the CSR::T1R chimeric protein in a suitable environment selected form the group consisting of solution, bilayer membrane, attached to a solid phase, in a lipid monolayer, bound on a membrane, and in vesicles.

* * * * *